United States Patent
Seldon et al.

(10) Patent No.: US 10,781,255 B2
(45) Date of Patent: Sep. 22, 2020

(54) ANTI-CD83 ANTIBODIES AND USE THEREOF

(71) Applicants: DENDROCYTE BIOTECH PTY LTD, Balmain (AU); THE UNIVERSITY OF QUEENSLAND, Queensland (AU); THE REGENTS OF THE UNIVERSITY OF CALIFORNIA, Oakland, CA (US)

(72) Inventors: Therese Ann Seldon, Bundoora (AU); David John Munster, Holland Park (AU); Derek Nigel John Hart, Concord (AU); Martina Louise Jones, Narangba (AU); Trent Phillip Munro, Newbury Park, CA (US); Stephen Michael Mahler, Indooroopilly (AU); Yu Zhou, San Francisco, CA (US); James D. Marks, Kensington, CA (US)

(73) Assignees: DENDROCYTE BIOTECH PTY LTD, Balmain (AU); THE UNIVERSITY OF QUEENSLAND, Queensland (AU); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 52 days.

(21) Appl. No.: 15/808,423

(22) Filed: Nov. 9, 2017

(65) Prior Publication Data

US 2018/0201681 A1   Jul. 19, 2018

Related U.S. Application Data

(62) Division of application No. 14/765,236, filed as application No. PCT/AU2014/000066 on Jul. 31, 2015, now Pat. No. 9,840,559.

(60) Provisional application No. 61/759,780, filed on Feb. 1, 2013.

(51) Int. Cl.
  *C07K 16/28*   (2006.01)
  *A61K 39/00*   (2006.01)

(52) U.S. Cl.
  CPC .... *C07K 16/2803* (2013.01); *A61K 2039/505* (2013.01); *A61K 2039/545* (2013.01); *C07K 2317/21* (2013.01); *C07K 2317/32* (2013.01); *C07K 2317/34* (2013.01); *C07K 2317/41* (2013.01); *C07K 2317/55* (2013.01); *C07K 2317/56* (2013.01); *C07K 2317/622* (2013.01); *C07K 2317/626* (2013.01); *C07K 2317/72* (2013.01); *C07K 2317/732* (2013.01); *C07K 2317/92* (2013.01)

(58) Field of Classification Search
  CPC .................................................. C07K 16/2803
  USPC .................................................... 424/173.1
  See application file for complete search history.

(56) References Cited

U.S. PATENT DOCUMENTS

| | | |
|---|---|---|
| 4,554,101 A | 11/1985 | Hopp |
| 4,593,089 A | 6/1986 | Wang et al. |
| 4,676,980 A | 6/1987 | Segal et al. |
| 4,751,190 A | 6/1988 | Chiapetta et al. |
| 4,816,397 A | 3/1989 | Boss et al. |
| 4,816,567 A | 3/1989 | Cabilly et al. |
| 4,946,778 A | 8/1990 | Ladner et al. |
| 5,225,539 A | 7/1993 | Winter |
| 5,260,203 A | 11/1993 | Ladner et al. |
| 5,316,920 A | 5/1994 | Tedder et al. |
| 5,516,637 A | 5/1996 | Huang et al. |
| 5,565,332 A | 10/1996 | Hoogenboom et al. |
| 5,571,728 A | 11/1996 | Kraus |
| 5,585,089 A | 12/1996 | Queen et al. |
| 5,731,168 A | 3/1998 | Carter et al. |
| 5,807,715 A | 9/1998 | Morrison et al. |
| 5,837,821 A | 11/1998 | Wu |
| 5,844,094 A | 12/1998 | Hudson et al. |
| 5,885,793 A | 3/1999 | Griffiths et al. |
| 6,054,297 A | 4/2000 | Carter et al. |
| 6,113,898 A | 9/2000 | Anderson et al. |
| 6,204,023 B1 | 3/2001 | Robinson et al. |
| 6,248,516 B1 | 6/2001 | Winter et al. |
| 6,248,597 B1 | 6/2001 | Eda et al. |
| 6,291,158 B1 | 9/2001 | Winter et al. |
| 6,300,064 B1 | 10/2001 | Knappik et al. |
| 6,331,415 B1 | 12/2001 | Cabilly et al. |
| 6,423,538 B1 | 7/2002 | Wittrup et al. |
| 6,602,684 B1 | 8/2003 | Umana et al. |
| 6,737,056 B1 | 5/2004 | Presta |
| 7,083,784 B2 | 8/2006 | Dall'Acqua et al. |
| 7,205,159 B2 | 4/2007 | Cole et al. |
| 7,217,797 B2 | 5/2007 | Hinton et al. |
| 7,217,798 B2 | 5/2007 | Hinton et al. |
| 7,270,969 B2 | 9/2007 | Watt et al. |
| 7,271,007 B2 | 9/2007 | Weigl et al. |
| 7,317,091 B2 | 1/2008 | Lazar et al. |
| 7,355,008 B2 | 4/2008 | Stavenhagen et al. |

(Continued)

FOREIGN PATENT DOCUMENTS

| | | |
|---|---|---|
| EP | 19930302894 | 11/1993 |
| EP | 2258724 | 12/2010 |

(Continued)

OTHER PUBLICATIONS

Merrifield J., Am. Chem. Soc., 85: 2149-2154, 1963.

(Continued)

*Primary Examiner* — Yan Xiao

(74) *Attorney, Agent, or Firm* — Heslin Rothenberg Farley & Mesiti P.C.

(57) ABSTRACT

The present disclosure relates to proteins that bind to CD83 and uses thereof, for example, in therapy, prophylaxis, diagnosis or prognosis.

25 Claims, 12 Drawing Sheets

Specification includes a Sequence Listing.

(56) References Cited

U.S. PATENT DOCUMENTS

| | | |
|---|---|---|
| 7,563,442 B2 | 7/2009 | Bedian et al. |
| 7,566,771 B1 | 7/2009 | Adair et al. |
| 7,732,578 B2 | 6/2010 | Foote |
| 8,197,809 B2 | 6/2012 | Park et al. |
| 2004/0116338 A1 | 6/2004 | Steinkasserer et al. |
| 2004/0185040 A1 | 9/2004 | Garcia-Martinez et al. |
| 2004/0228761 A1 | 11/2004 | Owens et al. |
| 2004/0265926 A1 | 12/2004 | Ng |
| 2005/0123546 A1 | 6/2005 | Umana et al. |
| 2007/0135620 A1 | 6/2007 | Chamberlain et al. |
| 2007/0190051 A1 | 8/2007 | Bedian et al. |
| 2007/0292416 A1 | 12/2007 | Rother et al. |
| 2008/0095767 A1 | 4/2008 | Jennings et al. |
| 2008/0152586 A1 | 6/2008 | Hudson et al. |
| 2009/0041770 A1 | 2/2009 | Chamberlain et al. |
| 2009/0247455 A1 | 10/2009 | Fear |
| 2010/0062489 A1 | 3/2010 | Guehenneux et al. |
| 2010/0221262 A1 | 9/2010 | Koch et al. |
| 2010/0226912 A1 | 9/2010 | Mehtali |
| 2015/0376277 A1 | 12/2015 | Seldon et al. |

FOREIGN PATENT DOCUMENTS

| | | |
|---|---|---|
| EP | 2726509 | 1/2015 |
| WO | 1995029236 | 11/1995 |
| WO | 1997030087 | 8/1997 |
| WO | 1999022764 | 5/1999 |
| WO | 1999058661 | 11/1999 |
| WO | 2000034317 | 6/2000 |
| WO | 2003045318 | 6/2003 |
| WO | 2004016284 | 2/2004 |
| WO | 2007150020 A1 | 12/2007 |
| WO | 2012088290 | 6/2012 |
| WO | 2016061617 A1 | 4/2016 |

OTHER PUBLICATIONS

Needleman and Wunsch, Mol. Biol., 48, 443-453, 1970.
Sakakibara Biochem. Biophys. Res. Commun., 73: 336-342, 1976.
Kyte and Doolittle, J. Mol. Biol., 157: 105-132, 1982.
Orr-Weaver and Szostack, Molecular and Cellular Biology, pp. 747-749, Apr. 1983.
Bodanszky Int. J. Peptide Protein Res., 25: 449-474, 1985.
Hellstrom et al., Proc. Natl. Acad. Sci. USA, 83: 7059-7063, 1986.
Bruggemann et al., J. Exp. Med. 166: 1351-1361, 1987.
Chothia and Lesk, J. Mol. Biol. 196: 901-917, 1987.
Harlow, E. and Lane, D., "Antibodies: A laboratory Manual", (1988) Cold Spring Harbor Laboratory Press, Cold Spring Harbor, New York.
Chothia et al., Nature, 342: 877-883, 1989.
Geitz and Schiestl, Yeast, 7(3): 253-263, 1991.
Hoogenboom et al., Nucleic Acids Res., 19(15): 4133-7, 1991.
Shalaby et al., J. Exp. Med., 175: 217-225, 1992.
Stemmer, Nature 370: 389-91, 1994.
Kim et al., Eur. J. Immunol., 24: 2429, 1994.
Sakaguchi et al., Nature, 426: 454-460, 1995.
Padlan et al., FASEB J., 9: 133-139, 1995.
Zhou and Tedder, J. Immunol., 154(8): 3821-35, 1995.
Tsunoda and Fujinami, J Neuropathol. Exp. Neurol., 55: 673-686, 1996.
Gazzano-Santoro et al., J. Immunol. Methods, 202: 163, 1996.
Al-Lazikani et al., J. Mol. Biol., 273: 927-948, 1997.
Giudicelli et al., Nucleic Acids Res. 25: 206-211, 1997.
Serke S. et al., Cytometry, 33(2): 179-87, 1998.
Sheets et al., Proc. Natl. Acad. Sci. U.S.A., 95(11): 6157-62, 1998.
Umana et al., Nat. Biotechnol., 17: 176-180, 1999.
Marsh et al., Hum. Mol. Genet. 9: 13-25, 2000.
Honnegher and Plukthun, J. Mol. Biol., 309: 657-670, 2001.
Bendele J., Musculoskel. Neuron. Interact. 1: 377-385, 2001.
Hock et al., International Immunology, 13(7), pp. 959-967, 2001.
Munster et al., Blood, vol. 100(11), Abstract No. 3694, 2002.
Zinser et al., J. Exp. Med., vol. 200, No. 3, pp. 345-351, 2004.
Mori et al., Biotechnol. Bioengineer., 88: 901-908, 2004.
Jostock et al., J. Immunol. Methods, 289: 65-80, 2004.
Yumane-Ohnuki et al., Biotechnol. Bioengineer, 87: 614-622, 2004.
Benny K.C.L., "Antibody Engineering: Methods and Protocols", (2004) Humana Press, vol. 248.
Kopsidas et al., Immunol. Lett., 107: 163-168, 2006.
Kanai et al., Inflamm Bowel Dis. 12: 89-99, 2006.
Kopsidas et al., BMC Biotechnology, 7: 18, 2007.
Kanda et al., J. Biotechnol., 130: 300-310, 2007.
Genbank Accession No. ABI35683, Dec. 30, 2007.
Natsume et al., Cancer Res., 68: 3863-3872, 2008.
Harmsen and Haard (Appl Microbiol Biotechnol 2007, 77: 13-22).
Wilson et al., J. Exp. Med., 206(2): 387-98, 2009.
Thie et al., Methods Mol. Biol. 525: 309-322, 2009.
Wu et al., Endocrine Metabolic and Immune Disorders—Drug Targets, vol. 9, No. 2, pp. 145-150, 2009.
Hart et al., "Developing a Therapeutic Anti-Dentritic Cell Antibody to Prevent Graft Versus Host Disease", Blood 2009, vol. 114, Supplement 22, Abstract 3554.
Wilson et al., "Antibody to the dendritic cell surface activation antigen CD83 prevents acute graft-versus-host disease", the Journal of Experimental Medicine, vol. 206, No. 2, pp. 387-398, Jan. 26, 2009.
Genbank Accession No. ACF37389, Mar. 31, 2009.
Zhou et al., J. Mol. Biol., 404(1): 88-99, 2010.
Jones et al., J. Immunol. Methods, 354: 85-90, 2010.
Seldon et al., J. Biomol. Tech, 22: 50-2, 2011.
Chen et al., "Two Novel Monoclonal Antibodies Produced Against Human CD83 Molecule", Hybridoma, vol. 30, No. 3, pp. 297-302, Jun. 2011.
International Search Report dated Apr. 11, 2014 for corresponding Application PCT/AU2014/000066.
Seldon et al., "Immunosuppressive human anti-CD83 monoclonal antibody depletion of activated dendritic cells in transplantation", Leukemia, vol. 30, No. 3, pp. 692-700, Aug. 19, 2015.
Supplemental European Search Report Application No. EP 14745637 entitled "Anti_CD83 Antibodies and Use Thereof", dated Sep. 20, 2016.
Database Geneseq [online] "Human DP-46 heavy chain variable region", retrieved from EBI accession No. GSP:AAM51167.
Chang, C., et al., "High Levels of Regulatory T Cells in Blood are a Poor Prognostic Factor in Patients With Diffuse Large B-Cell Lymphoma", American Journal of Clinical Pathology, vol. 144, pp. 935-944 (2015).
de Haard, H.J., et al., "A Large Non-immunized Human Fab Fragment Phage Library That Permits Rapid Isolation and Kinetic Analysis of High Affinity Antibodies", the Journal of Biological Chemistry, vol. 274, No. 26, pp. 18218-18230 (1999).
Dudziak, D., et al., "Alternative Splicing Generates Putative Soluble CD83 Proteins That Inhibit T Cell Proliferation", the Journal of Immunology, vol. 174, No. 11, pp. 6672-6676 (2005).
Hart, D., et al., Abstract No. D2342 "The Monoclonal Antibody 3C12C Targeting CD83 is a T Cell Sparing Potential New Immunosuppresive Agent", the American Society of Transplant Surgeons, the Transplantation Society and the American Society of Transplantation, vol. 98, No. 1, p. 390 (2014).
Li, Z., et al., "CD83 is a new potential biomarker and therapeutic target for Hodgkin lymphoma", Haematologica, vol. 103, No. 4, pp. 655-665 (2018).
Munster, D.J., et al., "Human T lymphoblasts and activated dendritic cells in the allogeneic mixed leukocyte reaction are susceptible to NK cell-mediated anti-CD83-dependent cytotoxicity", International Immunology, vol. 16, No. 1, pp. 33-42 (2004).
Immunoglobulin heavy chain variable region, partial [*Homo sapiens*] (ABI356683.1).
Khader, M et al., "The utility of fascin and CD83 in the differential diagnosis of medistinal large B cell lymphoma" Virchows Archives, 469 suppl 1, Ph S111 abstract PS-11-002 (2016).
Kim, J.K. et al., "Identifying Amino Acid Residues that Influence Plasma Clearance of Murine IgG1 Fragments by Site-Directed Mutagenesis" Eur. J Immunol., vol. 24, No. 3, pp. 542-548 (1994).

(56) References Cited

OTHER PUBLICATIONS

Marks, J.D., et al., "By-Passing Immunization: Building High Affinity Antibodies by Chain Shuffling", Nature Biotech., vol. 10, No. 7, pp. 779-783 (1992).
Sarantakis, et al.; "A Novel Cyclic Undecapeptide, WY-40,770, with Proionged Growth Hormone Release Inhibiting Activity", Biochem. Biophys. Res. Commun., vol. 73, pp. 336-342 (1976).

ANTI-CD83 ANTIBODIES AND USE THEREOF

CROSS REFERENCE TO RELATED APPLICATIONS

This application is a divisional of copending U.S. patent application Ser. No. 14/765,236, which was filed on Jul. 31, 2015 as a National Phase filing under 35 U.S.C. § 371 of International Patent Application No. PCT/AU2014/000066 filed on Jan. 31, 2014, which claims priority to U.S. Provisional Application No. 61/759,780. The entire disclosures of each of the prior applications are hereby incorporated herein by reference.

REFERENCE TO A SEQUENCE LISTING

This application contains a sequence listing in computer readable form; the file, 3075017A_seqlisting.txt is 43.4 KB in size. The file is hereby incorporated by reference into the instant disclosure.

FIELD

The present disclosure relates to proteins that bind to CD83 and uses thereof, for example, in therapy, prophylaxis, diagnosis, or prognosis.

BACKGROUND

CD83

CD83 is a 45 kDa, type-I membrane glycoprotein belonging to the immunoglobulin superfamily. CD83 is a cell surface marker predominantly expressed on mature dendritic cells (DCs). CD83 is minimally expressed on immature blood DC (BDC) and monocyte derived DC (MoDC). Due to its preferential expression on mature DCs, CD83 is an attractive target for immunotherapy.

Dendritic Cells and the Control of Innate and Adaptive Immune Responses

DCs link the innate and cognate (adaptive) immune systems. Innate immunity is the primary driver of non-specific immune activation in response to foreign agents. Immature DCs specialize in the internalisation of antigens and are distributed throughout peripheral tissues allowing for continuous antigenic surveillance. Termed professional antigen presenting cells (APCs) for their capability to drive primary T cell responses, DCs only require minimal quantities of antigen to initiate immune activation.

Immature DCs are attuned to a variety of signals from infectious and foreign material, which trigger differentiation and maturation (also known as activation) of the DCs. Whilst mature DCs are capable of antigen capture, this activation process reduces the capacity of these cells to internalize antigen, instead up-regulating cytokine release, activation marker expression and processing of antigen for major histocompatibility complex (MHC) presentation. Mature DCs loaded with processed antigen can efficiently recruit T cells, B cells, granulocytes, natural killer (NK) cells, monocytes and other cells of the innate immune system to amplify the response to antigen.

The molecules which become expressed upon DC differentiation and activation aid in linking innate and adaptive immunity. Mature DCs up-regulate the expression of chemokine receptors and adhesion molecules such as CD54, facilitating DC migration to lymph nodes for increased interaction with lymphocytes. Expression of costimulatory molecules, such as CD80 and CD86, provides the requisite co-stimulatory signals for T cell activation and the initiation of an antigen-specific immune response. Ligation of CD40 enhances the expression of co-stimulatory molecules and induces the release of IL-12 to facilitate T cell activation; differentiated T cells then orchestrate the complex interactions of the adaptive immune response.

Since DCs exert control over immune responses, activated DCs can be viewed as a target for intervention across a number of immunological diseases including malignancy and autoimmune diseases.

It will be apparent to the skilled person from the foregoing that compounds that target DCs may modulate the immune response. Accordingly, compounds that bind DCs are desirable, for example, for their therapeutic, prophylactic, diagnostic and prognostic uses.

SUMMARY

The present disclosure is based on the inventors' production of a human antibody (3C12 mAb) that binds specifically to CD83. 3C12 mAb was derived from a phage display library of human scFv sequences; the obtained scFv phage clone reformatted as an IgG1 mAb.

The 3C12 mAb was shown to out compete its polyclonal equivalent, RA83, in competitive binding assays and delay onset of graft versus host disease (GVHD) in SCID mice transplanted with a xenogeneic graft of human PBMC.

To improve the therapeutic efficacy of the 3C12 mAb, the inventors performed affinity maturation of the light chain to improve the affinity of the 3C12 mAb for CD83. Four new 3C12 scFv variants (3C12.B, 3C12.C, 3C12.D and 3C12.E) with distinct light chain variable region ($V_L$) sequences and enhanced binding properties relative to the wild type scFv were obtained. The affinity matured antibodies included substitutions in the framework (FR) and complementarity determining regions (CDRs) of the $V_L$. The effect of these substitutions were not predictable.

The inventors also produced forms of 3C12 mAb capable of inducing enhanced levels of effector function, with defucosylated 3C12.C mAb having comparable potency to polyclonal antibody, RA83.

The present disclosure is broadly directed to a CD83 binding protein comprising an antigen binding domain which specifically binds to CD83.

In one example, the present disclosure provides a CD83 binding protein comprising an antigen binding domain which specifically binds to CD83, wherein the binding protein comprises a heavy chain variable region ($V_H$) which comprises a sequence which is at least 90% identical to the amino acid sequence shown in SEQ ID NO:1. In one example, the heavy chain variable region ($V_H$) comprises a sequence which is at least 90% identical to the frame work regions of the amino acid sequence shown in SEQ ID NO: 1.

The present disclosure additionally or alternatively provides a CD83 binding protein comprising an antigen binding domain which specifically binds to CD83, wherein the binding protein comprises a heavy chain variable region ($V_H$) which comprises three complementarity determining regions (CDRs) of the amino acid sequence shown in SEQ ID NO:1.

In one example, the $V_H$ CDR1 comprises amino acids 31 to 35 of SEQ ID NO: 1, the $V_H$ CDR2 comprises amino acids 50 to 59 of SEQ ID NO:1 and the $V_H$ CDR3 comprises amino acids 99 to 106 of SEQ ID NO: 1.

In one example, the $V_H$ CDR1 comprises the amino acid sequence shown in SEQ ID NO:2, the $V_H$ CDR2 comprises the amino acid sequence shown in SEQ ID NO:3 and the $V_H$ CDR3 comprises the amino acid sequence shown in SEQ ID NO:4.

The present disclosure additionally or alternatively provides a CD83 binding protein comprising an antigen binding domain which specifically binds to CD83, wherein the binding protein comprises a light chain variable region ($V_L$) which comprises:

(i) a sequence which is at least 90% identical to any one of the amino acid sequences shown in SEQ ID NO:5, 6, 7, 8, or 9; or (ii) three complementarity determining regions (CDRs) of any one of the amino acid sequences shown in SEQ ID NO:5, 6, 7, 8, or 9; or (iii) a consensus sequence as shown in SEQ ID NO:10; or (iv) three CDRs, wherein the amino acid sequence of CDR1, CDR2, or CDR3 is a consensus sequence shown in SEQ ID NO:26, 27, or 28.

In one example, the light chain variable region ($V_L$) comprises a sequence which is at least 90% identical to the frame work regions of any one of the amino acid sequences shown in SEQ ID NO:5, 6, 7, 8, or 9.

In one example, the $V_L$ CDR1 comprises amino acids 24 to 34 of SEQ ID NO:5, 6, 7, 8, or 9, the $V_L$ CDR2 comprises amino acids 50 to 56 of SEQ ID NO:5, 6, 7, 8, or 9 and the $V_L$ CDR3 comprises amino acids 89 to 97 of SEQ ID NO:5, 6, 7, 8, or 9.

In one example, the $V_L$ CDR1 comprises the amino acid sequence shown in SEQ ID NO:11, 14, 17, 20, or 23, the $V_L$ CDR2 comprises the amino acid sequence shown in SEQ ID NO:12, 15, 18, 21, or 24 and the $V_L$ CDR3 comprises the amino acid sequence shown in SEQ ID NO:13, 16, 19, 22, or 25.

In one example, the amino acid sequence of $V_L$ CDR1 comprises an Alanine (A) or Threonine (T) at position 2 and/or a Lysine (K) or Serine (S) or Arginine (R) at position 7 and/or an Asparagine (N) or Serine (S) at position 8 and/or a Tyrosine (Y) or Histidine (H) or Tryptophan (W) at position 9 and/or a Phenylalanine (F) or Leucine (L) at position 10.

In one example, the amino acid sequence of $V_L$ CDR2 comprises a Threonine (T) or Alanine (A) at position 2 and/or an Asparagine (N) or Serine (S) or Threonine (T) at position 4.

In one example, the amino acid sequence of $V_L$ CDR3 comprises a Glutamine (Q) or Lysine (K) at position 2 and/or a Leucine (L) or Valine (V) or Cysteine (C) at position 3 and/or a Glycine (G) or Asparagine (N) or Aspartic Acid (D) or Serine (S) at position 4 and/or an Alanine (A) or Serine (S) or Arginine (R) at position 5 and/or a Tyrosine (Y) or Phenylalanine (F) or Alanine (A) at position 6 and/or a Tyrosine (Y) or Leucine (L) at position 8.

In one example, the $V_H$ and the $V_L$ are in a single polypeptide chain. For example, the CD83 binding protein is:

(i) a single chain Fv fragment (scFv); or (ii) a dimeric scFv (di-scFv); or (iii) (i) or (ii) linked to a Fc or a heavy chain constant domain ($C_H$) 2 and/or $C_H$3; or (iv) (i) or (ii) linked to a protein that binds to an immune effector cell.

In another example, the $V_L$ and $V_H$ are in separate polypeptide chains. For example, the CD83 binding protein is:

(i) a diabody; or (ii) a triabody; or (iii) a tetrabody; or (iv) a Fab; or (v) a F(ab')$_2$; or (vi) a Fv; or (vii) one of (i) to (vi) linked to a Fc or a $C_H$2 and/or $C_H$3; or (viii) one of (i) to (vi) linked to a protein that binds to an immune effector cell.

In one example, a CD83 binding protein of the disclosure comprises an antigen binding domain that competitively inhibits the binding of an antibody to CD83, the antibody comprising a heavy chain sequence as shown in SEQ ID NO:29 and a light chain sequence as shown in SEQ ID NO:30.

Exemplary CD83 binding proteins of the present disclosure comprise a $V_H$ of the disclosure and a chimeric, de-immunized, humanized, human, synhumanized or primatized light chain or $V_L$.

In an exemplary form of the present disclosure, the CD83 binding protein is an antibody. The antibody may comprise:

(i) a $V_H$ sequence as shown in SEQ ID NO:1 and a $V_L$ sequence as shown in SEQ ID NO:5; or (ii) a $V_H$ sequence as shown in SEQ ID NO:1 and a $V_L$ sequence as shown in SEQ ID NO:6; or (iii) a $V_H$ sequence as shown in SEQ ID NO:1 and a $V_L$ sequence as shown in SEQ ID NO:7; or (iv) a $V_H$ sequence as shown in SEQ ID NO:1 and a $V_L$ sequence as shown in SEQ ID NO:8; or (v) a $V_H$ sequence as shown in SEQ ID NO:1 and a $V_L$ sequence as shown in SEQ ID NO:9; or (vi) a heavy chain sequence as shown in SEQ ID NO:29 and a light chain sequence as shown in SEQ ID NO:30; or (vii) a heavy chain sequence as shown in SEQ ID NO:29 and a light chain sequence as shown in SEQ ID NO:31; or (viii) a heavy chain sequence as shown in SEQ ID NO:29 and a light chain sequence as shown in SEQ ID NO:32; or (ix) a heavy chain sequence as shown in SEQ ID NO:29 and a light chain sequence as shown in SEQ ID NO:33; or (x) a heavy chain sequence as shown in SEQ ID NO:29 and a light chain sequence as shown in SEQ ID NO:34.

In one example, the antibody depletes cells to which it binds, for example, immune cells such as antigen presenting cells (APC) (e.g., dendritic cells (DCs)) and/or lymphocytes (e.g., T cells).

As will be apparent to the skilled artisan from the disclosure herein, exemplary CD83 binding proteins are capable of depleting cells to which they bind without being conjugated to a toxic compound.

In one example, the CD83 binding protein is capable of inducing an effector function, for example, an effector function that results in killing a cell to which antibody binds. Exemplary effector functions include antibody dependent cell-mediated cytotoxicity (ADCC), antibody-dependent cell-mediated phagocytosis (ADCP) and/or complement-dependent cytotoxicity (CDC).

In one example, the CD83 binding protein is capable of inducing ADCC.

In one example, the CD83 binding protein comprises an antibody Fc region capable of inducing an effector function. For example, the effector function is Fc-mediated effector function. In one example, the Fc region is an IgG1 Fc region or an IgG3 Fc region or a hybrid IgG1/IgG2 Fc region.

In one example, the CD83 binding protein is capable of inducing a similar (e.g., not significantly different or within about 10%) or the same level of effector function as a wild-type human IgG1 and/or human IgG3 Fc region.

In one example, the CD83 binding protein is capable of inducing an enhanced level of effector function.

In one example, the level of effector function induced by the CD83 binding protein is enhanced relative to that of the CD83 binding protein when it comprises a wild-type IgG1 Fc region.

In one example the CD83 binding protein is defucosylated or comprises a Fc region that is defucosylated.

In another example, the CD83 binding protein has a lower level of fucosylation compared to an antibody produced by a human or a CHO cell that has not been altered to reduce the level of fucosylation of proteins. In accordance with this example, a lower level of fucosylation will be understood to mean that in a composition comprising the CD83 binding protein, the percentage of fucosylated CD83 binding proteins (e.g., glycosyl groups attached to Asn297 of an antibody comprising fucose) is lower than produced by a human or a CHO cell that has not been altered to reduce the level of fucosylation of proteins.

For example, the CD83 binding protein is a defucosylated antibody comprising a $V_H$ comprising an amino acid sequence as shown in SEQ ID NO:1 (or encoded by a nucleotide sequence set forth in SEQ ID NO:35) and a $V_L$ comprising an amino acid sequence as shown in any one of SEQ ID NOs:5, 6, 7, 8, or 9 (or encoded by a nucleotide sequence as shown in any one of SEQ ID NOs:36, 37, 38, 39, or 40).

In one example, the CD83 binding protein comprises a $V_H$ comprising an amino acid sequence as shown in SEQ ID NO:1 (or encoded by a nucleotide sequence as shown in SEQ ID NO:35) and a $V_L$ comprising an amino acid sequence as shown in any one of SEQ ID NOs:5, 6, 7, 8, or 9 (or encoded by a nucleotide sequence as shown in any one of SEQ ID NO:36, 37, 38, 39, or 40) and is expressed by a mammalian cell (e.g., a CHO cell) that does not express detectable levels of (or expresses reduced levels of) α-1,6-fucosyltransferase (FUT8) or is treated with an inhibitor of N-glycan processing such as kifunensine.

In one example, the CD83 binding protein comprises an Fc region comprising one or more amino acid sequence substitutions that enhance the effector function induced by the antibody. For example, the one or more amino acid sequence substitutions increase the affinity of the Fc region for a Fcγ receptor (FcγR) compared to a Fc region not comprising the substitutions. For example, the one or more amino acid substitutions increase the affinity of the Fc region for a FcγR selected from the group consisting of FcγRI, FcγRIIa, FcγRIIc and FcγRIIIa compared to a Fc region not comprising the substitutions.

In one example, a CD83 binding protein of the present disclosure is a naked antibody or antigen binding fragment thereof.

In one example, a CD83 binding protein of the present disclosure is a full length antibody.

In one example, a CD83 binding protein of the present disclosure binds to CD83 with an equilibrium dissociation constant ($K_D$) of $5 \times 10^{-7}$ M or less, such as $4.5 \times 10^{-7}$ M or less, such as $4 \times 10^{-7}$ M or less, such as $3.5 \times 10^{-7}$ M or less, such as $3 \times 10^{-7}$ M or less, such as $2.5 \times 10^{-7}$ M or less, such as $2 \times 10^{-7}$ M or less, such as $1.5 \times 10^{-7}$ M or less, such as $1 \times 10^{-7}$ M or less, such as $9.5 \times 10^{-8}$ M or less, such as $9 \times 10^{-8}$ M or less, such as $8.5 \times 10^{-8}$ M or less, such as $8 \times 10^{-8}$ M or less, such as $7.5 \times 10^{-8}$ M or less, such as $7 \times 10^{-8}$ M or less, such as $6.5 \times 10^{-8}$ M or less, such as $6 \times 10^{-8}$ M or less, such as $5.5 \times 10^{-8}$ M or less, such as $5 \times 10^{-8}$ M or less, such as $4.5 \times 10^{-8}$ M or less, such as $4 \times 10^{-8}$ M or less, such as $3.5 \times 10^{-8}$ M or less, such as $3 \times 10^{-8}$ M or less, such as $2.5 \times 10^{-8}$ M or less, such as $2 \times 10^{-8}$ M or less, such as $1.5 \times 10^{-8}$ M or less, such as $1 \times 10^{-8}$ M or less, such as $9.5 \times 10^{-9}$ M or less, such as $9 \times 10^{-9}$ M or less, such as $8.5 \times 10^{-9}$ M or less, such as $8 \times 10^{-9}$ M or less, such as $7.5 \times 10^{-9}$ M or less, such as $7 \times 10^{-9}$ M or less, such as $6.5 \times 10^{-9}$ M or less, such as $6 \times 10^{-9}$ M or less, such as $5.5 \times 10^{-9}$ M or less, such as $5 \times 10^{-9}$ M.

In one example, a CD83 binding protein of the present disclosure binds to CD83 with a $K_D$ of about $6 \times 10^{-9}$ M or less, for example, $6.1 \times 10^{-9}$ M. In one example, the $K_D$ is between about $5.5 \times 10^{-9}$ M and about $6.5 \times 10^{-9}$ M, for example, is about $6 \times 10^{-9}$ M.

In one example, a CD83 binding protein of the present disclosure binds to CD83 with an on rate ($K_{on}$) of $5 \times 10^6$ $M^{-1}s^{-1}$ or less, such as $4.5 \times 10^6$ $M^{-1}s^{-1}$ or less, such as $4 \times 10^6$ $M^{-1}s^{-1}$ or less, such as $3.5 \times 10^6$ $M^{-1}s^{-1}$ or less, such as $3 \times 10^6$ $M^{-1}s^{-1}$ or less, such as $2.5 \times 10^6$ $M^{-1}s^{-1}$ or less, such as $2 \times 10^6$ $M^{-1}s^{-1}$ or less, such as $1.5 \times 10^6$ $M^{-1}s^{-1}$ or less, such as $1 \times 10^6$ $M^{-1}s^{-1}$ or less, such as $9.5 \times 10^5$ $M^{-1}s^{-1}$ or less, such as $9 \times 10^5$ $M^{-1}s^{-1}$ or less, such as $8.5 \times 10^5$ $M^{-1}s^{-1}$ or less, such as $8 \times 10^5$ $M^{-1}s^{-1}$ or less, such as $7.5 \times 10^5$ $M^{-1}s^{-1}$ or less, such as $7 \times 10^5$ $M^{-1}s^{-1}$ or less, such as $6.5 \times 10^5$ $M^{-1}s^{-1}$ or less, such as $6 \times 10^5$ $M^{-1}s^{-1}$ or less, such as $5.5 \times 10^5$ $M^{-1}s^{-1}$ or less, such as $5 \times 10^5$ $M^{-1}s^{-1}$ or less, such as $4.5 \times 10^5$ $M^{-1}s^{-1}$ or less, such as $4 \times 10^5$ $M^{-1}s^{-1}$ or less, such as $3.5 \times 10^5$ $M^{-1}s^{-1}$ or less, such as $3 \times 10^5$ $M^{-1}s^{-1}$ or less, such as $2.5 \times 10^5$ $M^{-1}s^{-1}$ or less, such as $2 \times 10^5$ $M^{-1}s^{-1}$ or less, such as $1.5 \times 10^5$ $M^{-1}s^{-1}$ or less, such as $1 \times 10^5$ $M^{-1}s^{-1}$.

In one example, a CD83 binding protein of the present disclosure binds to CD83 with a $K_{on}$ of about $1.5 \times 10^6$ $M^{-1}s^{-1}$ or less. In one example, the $K_D$ is between about $1.2 \times 10^6$ $M^{-1}s^{-1}$ and about $1.6 \times 10^6$ $M^{-1}s^{-1}$, for example, is about $1.3 \times 10^6$ $M^{-1}s^{-1}$.

In one example, a CD83 binding protein of the present disclosure dissociates from CD83 with an off rate of ($K_{off}$) of $1.5 \times 10^{-1}$ $s^{-1}$ or less, such as $1 \times 10^{-1}$ $s^{-1}$ or less, such as $9.5 \times 10^{-2}$ $s^{-1}$ or less, such as $9 \times 10^{-2}$ $s^{-1}$ or less, such as $8.5 \times 10^{-2}$ $s^{-1}$ or less, such as $8 \times 10^{-2}$ $s^{-1}$ or less, such as $7.5 \times 10^{-2}$ $s^{-1}$ or less, such as $7 \times 10^{-2}$ $s^{-1}$ or less, such as $6.5 \times 10^{-2} s^{-1}$ or less, such as $6 \times 10^{-2}$ $s^{-1}$ or less, such as $5.5 \times 10^{-2}$ $s^{-1}$ or less, such as $5 \times 10^{-2}$ $s^{-1}$ or less, such as $4.5 \times 10^{-2}$ $s^{-1}$ or less, such as $4 \times 10^{-2}$ $s^{-1}$ or less, such as $3.5 \times 10^{-2}$ $s^{-1}$ or less, such as $3 \times 10^{-2}$ $s^{-1}$ or less, such as $2.5 \times 10^{-2}$ $s^{-1}$ or less, such as $2 \times 10^{-2}$ $s^{-1}$ or less, such as $1.5 \times 10^{-2}$ $s^{-1}$ or less, such as $1 \times 10^{-2}$ $s^{-1}$ or less, such as $9.5 \times 10^{-3}$ $s^{-1}$ or less, such as $9 \times 10^{-3}$ $s^{-1}$ or less, such as $8.5 \times 10^{-3}$ $s^{-1}$ or less, such as $8 \times 10^{-3}$ $s^{-1}$ or less, such as $7.5 \times 10^{-3}$ $s^{-1}$ or less, such as $7 \times 10^{-3}$ $s^{-1}$ In one example, a CD83 binding protein of the present disclosure dissociates from CD83 with a $K_{off}$ of about $8 \times 10^{-3}$ $s^{-1}$ or less. In one example, the $K_D$ is between about $7 \times 10^{-3}$ $s^{-1}$ and about $9 \times 10^{-3}$ $s^{-1}$, for example, is about $8 \times 10^{-3}$ $s^{-1}$.

The disclosure also includes fragments, variants and derivatives of the antibody of the disclosure.

In one example, the disclosure provides a pharmaceutical composition comprising a CD83 binding protein according to the present disclosure and a suitable carrier, for example, a pharmaceutically acceptable carrier, diluent or excipient.

The present disclosure also provides an isolated or recombinant nucleic acid encoding a CD83 binding protein of the present disclosure.

Exemplary sequences of nucleic acids are discussed in the context of encoding CD83 binding proteins of the disclosure and are to be taken to apply mutatis mutandis to the present example of the disclosure.

In one example, the nucleic acid of the disclosure comprises a nucleotide sequence as shown in any one of SEQ ID NOs:35 to 46.

The present disclosure also provides a nucleic acid capable of hybridizing to a nucleic acid of the disclosure under moderate or high stringency hybridization conditions.

The disclosure also includes fragments, homologs and derivatives of an isolated nucleic acid of the disclosure.

The present disclosure also provides a genetic construct comprising an isolated or recombinant nucleic acid of the disclosure and one or more additional nucleotide sequences, such as a promoter operably linked to the nucleic acid.

In one example, the genetic construct is an expression construct comprising an expression vector and an isolated or recombinant nucleic acid of the disclosure, wherein said isolated or recombinant nucleic acid is operably linked to one or more regulatory nucleic acids in said expression vector.

In one example, the genetic construct of the disclosure comprises a nucleic acid encoding a polypeptide (e.g., comprising a $V_H$) operably linked to a promoter and a nucleic acid encoding another polypeptide (e.g., comprising a $V_L$) operably linked to a promoter.

In another example, the genetic construct is a bicistronic genetic construct, for example, comprising the following operably linked components in 5' to 3' order:
  (i) a promoter;
  (ii) a nucleic acid encoding a first polypeptide;
  (iii) an internal ribosome entry site; and
  (iv) a nucleic acid encoding a second polypeptide.

For example, the first polypeptide comprises a $V_H$ and the second polypeptide comprises a $V_L$, or the first polypeptide comprises a $V_L$ and the second polypeptide comprises a $V_H$.

The present disclosure also contemplates separate genetic constructs one of which encodes a first polypeptide (e.g., comprising a $V_H$) and another of which encodes a second polypeptide (e.g., comprising a $V_L$). For example, the present disclosure also provides a composition comprising:
  (i) a first genetic construct comprising a nucleic acid encoding a polypeptide (e.g., comprising a $V_H$) operably linked to a promoter; and
  (ii) a second genetic construct comprising a nucleic acid encoding a polypeptide (e.g., comprising a $V_L$) operably linked to a promoter.

The disclosure also provides a cell comprising a genetic construct according to the present disclosure.

In one example, the present disclosure provides an isolated cell expressing a CD83 binding protein of the disclosure or a recombinant cell genetically-modified to express the CD83 binding protein of the invention.

In one example, the cell comprises the genetic construct of the disclosure or:
  (i) a first genetic construct comprising a nucleic acid encoding a polypeptide (e.g., comprising a $V_H$) operably linked to a promoter; and
  (ii) a second genetic construct comprising a nucleic acid encoding a polypeptide (e.g., comprising a $V_L$) operably linked to a promoter,
wherein the first and second polypeptides form an antibody or an antigen binding fragment of the present disclosure.

The genetic construct can be integrated into the cell or remain episomal.

Examples of cells of the present disclosure include bacterial cells, yeast cells, insect cells or mammalian cells.

The present disclosure additionally provides a method for producing a CD83 binding protein of the disclosure, the method comprising maintaining the genetic construct(s) of the disclosure under conditions sufficient for the CD83 binding protein to be produced.

In one example, the method for producing a CD83 binding protein of the disclosure comprises culturing the cell of the disclosure under conditions sufficient for the CD83 binding protein to be produced and, optionally, secreted.

In one example, the method for producing a CD83 binding protein of the disclosure additionally comprises isolating the CD83 binding protein.

The present disclosure additionally provides a method of producing a recombinant CD83 binding protein, the method including the steps of:
  (i) culturing a cell containing an expression vector according to the disclosure such that the recombinant immunoglobulin or antibody is expressed in said host cell; and
  (ii) isolating the recombinant CD83 binding protein.

In one example, a method for producing a CD83 binding protein of the disclosure additionally comprises formulating the CD83 binding protein with a pharmaceutically acceptable carrier.

The present disclosure also provides a method of therapeutic or prophylactic treatment of a disease or condition in a subject, the method including the step of administering the CD83 binding protein of the disclosure to the subject to thereby treat or prevent the disease or condition.

In one example, the subject is a mammal.

In one example, the mammal is a human.

In one example, the mammal is in need of treatment or prophylaxis.

In one example, the mammal in need suffers from the disease or condition.

In one example, the mammal in need is at risk of developing the disease or condition or a relapse thereof.

The present disclosure also provides for use of a CD83 binding protein of the disclosure or a composition of the disclosure in medicine.

The present disclosure additionally or alternatively provides for use of a CD83 binding protein of the disclosure in the manufacture of a medicament for the treatment of a disease or condition in a subject.

The present disclosure also provides a CD83 binding protein of the disclosure for use in the treatment of a disease or condition in a subject.

In one example, the disease or condition is a CD83 mediated disease or condition.

In one example, the disease or condition is an autoimmune disease or condition, or an inflammatory disease or condition. For example, the disease or condition is myasthemia gravis, multiple sclerosis, vasculitis, chronic inflammatory bowel diseases such as Morbus Crohn or colitis ulcerosa, HLA B27-associated autoimmune disorders such as Morbus Bechterew, and systemic lupus erythematosis, skin diseases such as psoriasis, rheumatoid arthritis, and insulin-dependent diabetes mellitus.

In one example, the disease or condition is caused by the dysfunction or undesired function of the immune system or a cellular response involving antigen presenting cells (APC) (e.g., dendritic cells (DCs)) and/or lymphocytes (e.g., T cells) in a subject.

In another example, the disease or condition is rejection of a tissue or organ graft. For example, rejection of a tissue or organ transplant occurs as a result of graft versus host disease or host versus graft disease.

In another example, the disease or condition is rejection of a stem cell graft, for example, an hematopoietic stem cell transplantation (HSCT) or an umbilical cord blood transplantation (UCBT). For example, rejection of the stem cell transplant occurs as a result of graft versus host disease or host versus graft disease. The HSCT may be derived from, for example, the bone marrow directly or from the peripheral blood following mobilization of cells from the bone marrow (e.g. by administration of G-CSF).

In one example, the method comprises administering an effective amount of the CD83 binding protein, such as a therapeutically effective amount of the CD83 binding protein to the donor and/or recipient. The graft may be contacted with an effective amount of the CD83 binding protein ex vivo or in vivo prior to or after being transplanted.

The present disclosure also provides a method for down-regulating the immunoactivity of an allogeneic graft, the method comprising contacting the graft with a CD83 binding protein or a composition of the disclosure.

In one example, the allogeneic graft is an hematopoietic stem cell graft.

In one example, the graft is contacted with a CD83 binding protein or a composition of the disclosure ex vivo.

In another or additional example, the recipient of the graft is administered a CD83 binding protein or a composition of the disclosure prior to and/or simultaneously with and/or following transplant of the graft.

(A) Non-reduced (NR) and 2-mercaptoethanol reduced (R) samples of culture supernatants (i, iii) and 5 µg affinity purified material (ii, iv) were separated on 4-12% SDS-PAGE and stained with Coomassie Blue R250. (B) Analytical size exclusion chromatography (SEC) of protein-A purified recombinant 3C12 antibody at both 280 nm (top panel) and 215 nm (middle panel), and gel filtration standards at 215 nm (bottom panel). The sample shows no detectable aggregation and a predicted molecular weight of 145 kDa.

Figure 2:
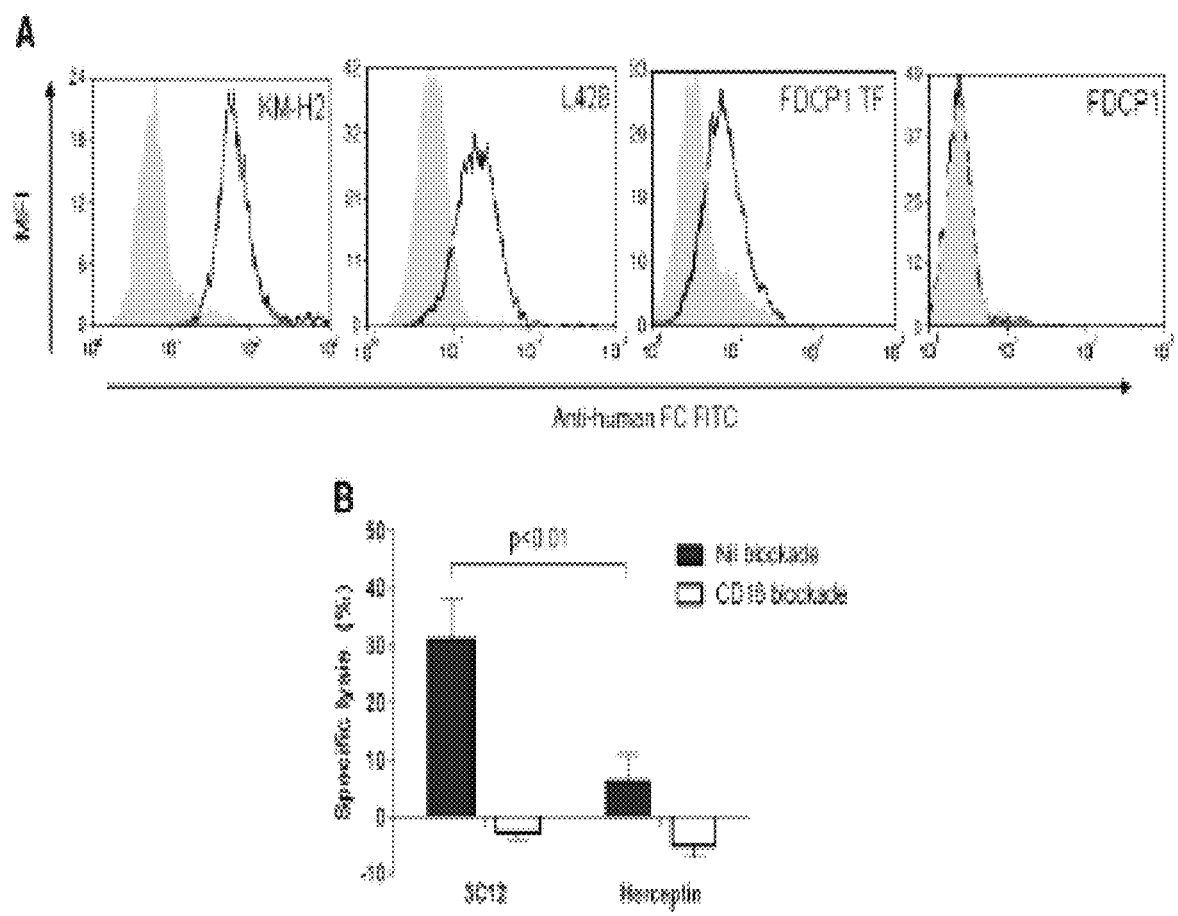

FIG. 2: Functional analysis of purified 3C12, an anti-human CD83 IgG (A) 25 µg·mL$^{-1}$ 3C12 IgG1 binds the CD83$^+$ cell lines KM-H2 and L428 and also FDCP1 cells transfected with human CD83 (FDCP1 TF). No difference between 3C12 and an isotype IgG1 control is seen on un-transfected FDCP1 cells (CD83−). MFI=mean fluorescence intensity. (B) 3C12 IgG1 induced significant lysis of the KM-H2 cell line relative to Herceptin (negative control) via a CD16-dependent mechanism at an effector to target cell ratio of 5:1. Statistical significance was determined by two-way ANOVA. Error bars represent standard error of the mean (SEM) of five replicates.

Figure 3:
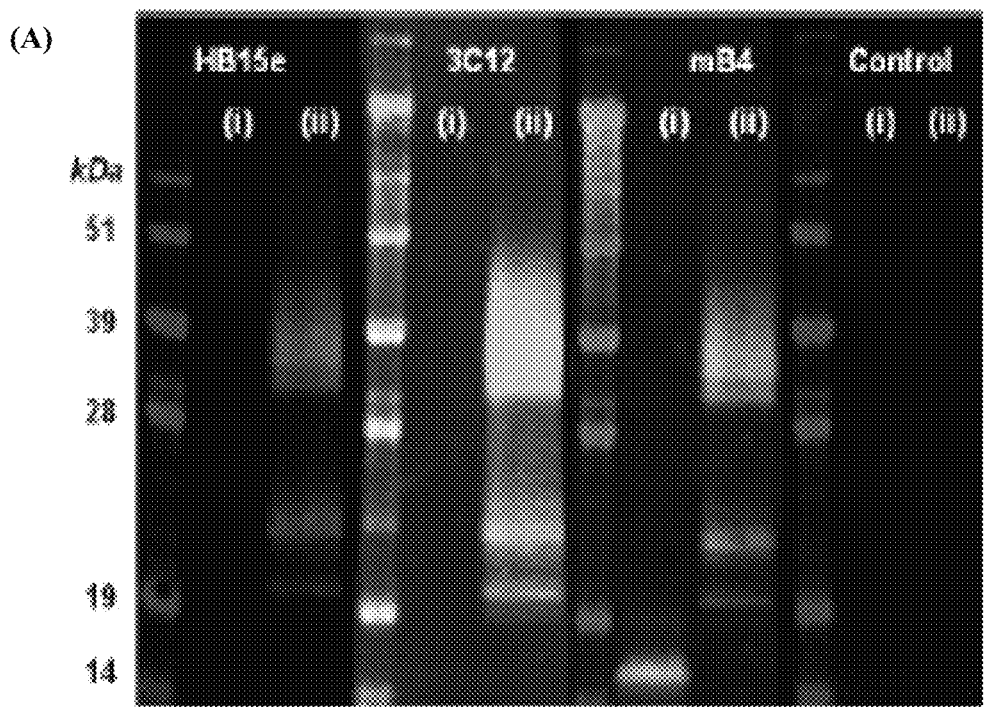

FIG. 3: 3C12 recognises a conformational epitope that overlaps with other CD83 antibodies (A) Western blot of CD83 antibodies used to detect 5 g of (i) denatured or (ii) native recombinant human CD83ECD-His. Non-denatured CD83 appears as three smeared bands (30 kDa, 22 kDa, 19 kDa) on 12% gel, the result of homo-dimerization and variability in glycosylation of the three potential N-linked glycosylation motifs. Anti-human IgG IRD800 secondary antibody alone was used as a negative control. (Inset table). Effect of simultaneous addition of CD83 antibodies to KM-H2 cells and the resulting change in mean fluorescence intensity for 3C12 and other antibodies reported as percent reduction.

Figure 4:
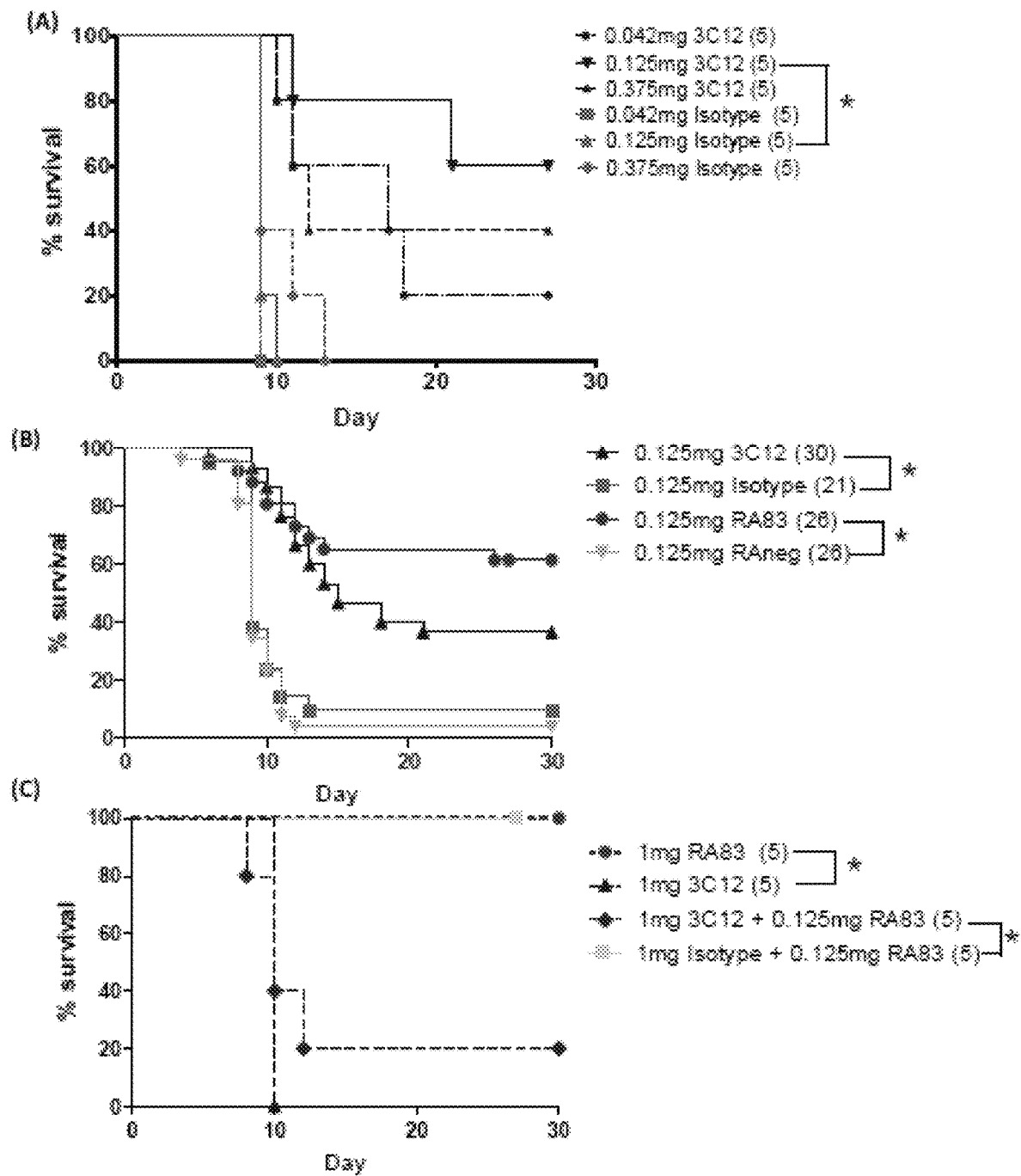

FIG. 4: 3C12 mAb improves in vivo survival of SCID mice in a xenogeneic GVHD model Survival of animals after administration on Day 0 of CD83 antibody or isotype matched control to SCID mice transplanted with human PBMC. The number of animals used per cohort is shown in brackets and significant differences ($p<0.05$) are asterisked. (A) Dose optimisation of 3C12 IgG in comparison to isotype control (anti-human Her2; Herceptin IgG). (B) Comparison of 0.125 mg dose of 3C12 IgG with rabbit polyclonal RA83 antibody or non-specific rabbit IgG (RAneg). Data displayed is pooled from 5 independent experiments each containing a minimum of five animals in each cohort. (C) Administration of a 1 mg dose of CD83 antibody and combined dose of 3C12 and RA83 treatments.

Figure 5:
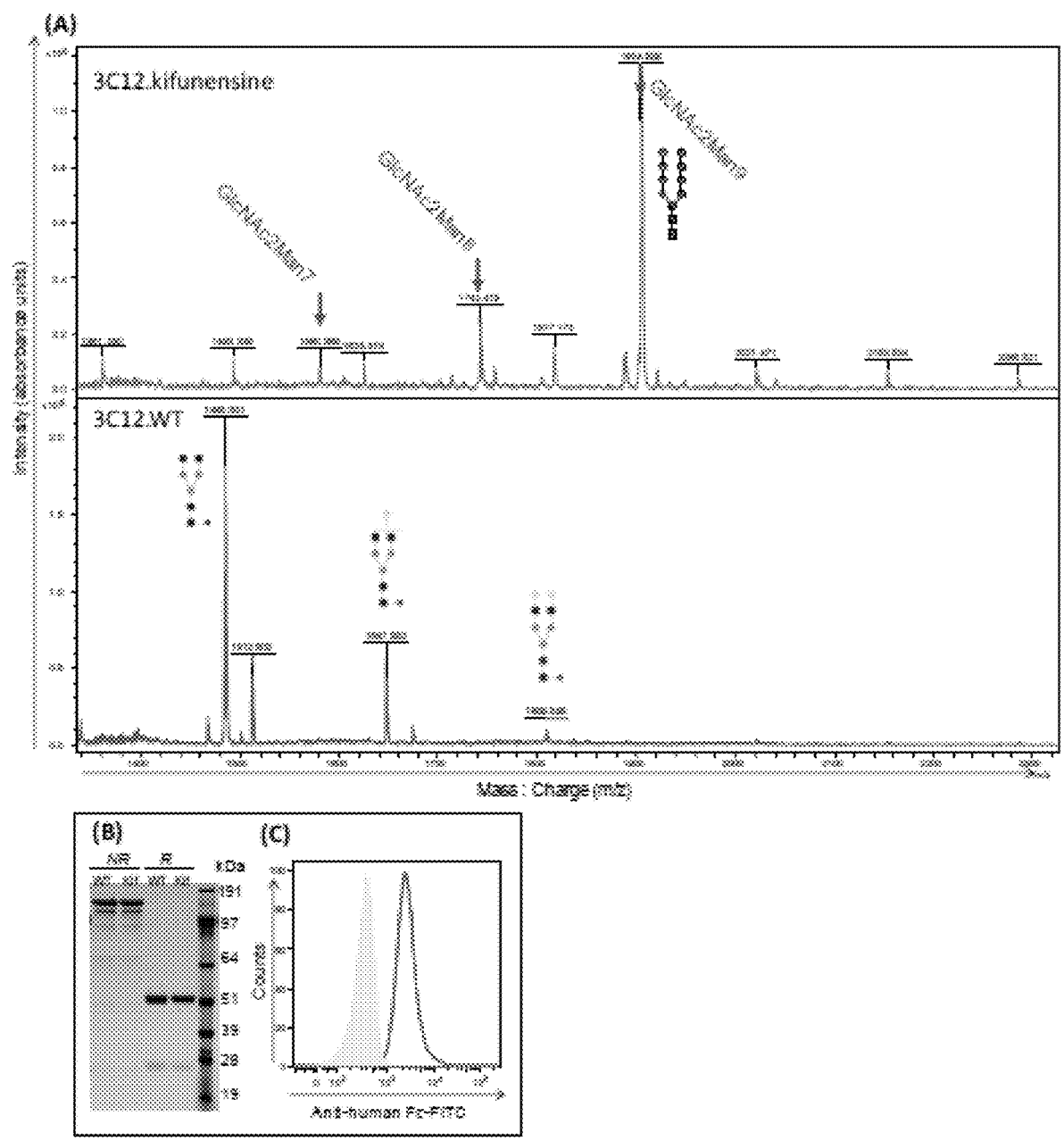

FIG. 5: Glycomodification of 3C12 with kifunesine results in low-fucose IgG (A) Production of 3C12 in the presence of 2 µg·mL$^{-1}$ kifunensine (3C12.kif, top panel) inhibits addition of fucose, whilst fucose is a large component of the sugars present within the control 3C12 transfection (3C12.WT; lower panel) as determined by MALDI TOF/TOF mass spectrometry. Structures typically produced at each predominant signal are annotated and schematically represented by fucose (triangles), GlcNAC (squares), mannose (dark grey circles), and galactose (light grey circles). (B) 3C12.WT and 3C12.Kif are of a standard IgG molecule weight (150 kDa non-reduced (NR), and 50 kDa, 25 kDa bands observed upon reduction (R)) and (C) kifunesine treatment does not alter binding activity of 3C12.kif IgG (MFI=2573, grey line) to CD83$^+$ cell line, KM-H2 in comparison to 3C12.WT (MFI=2581, black line superimposed on grey line) relative to isotype control (MFI=335, grey fill).

Figure 6:
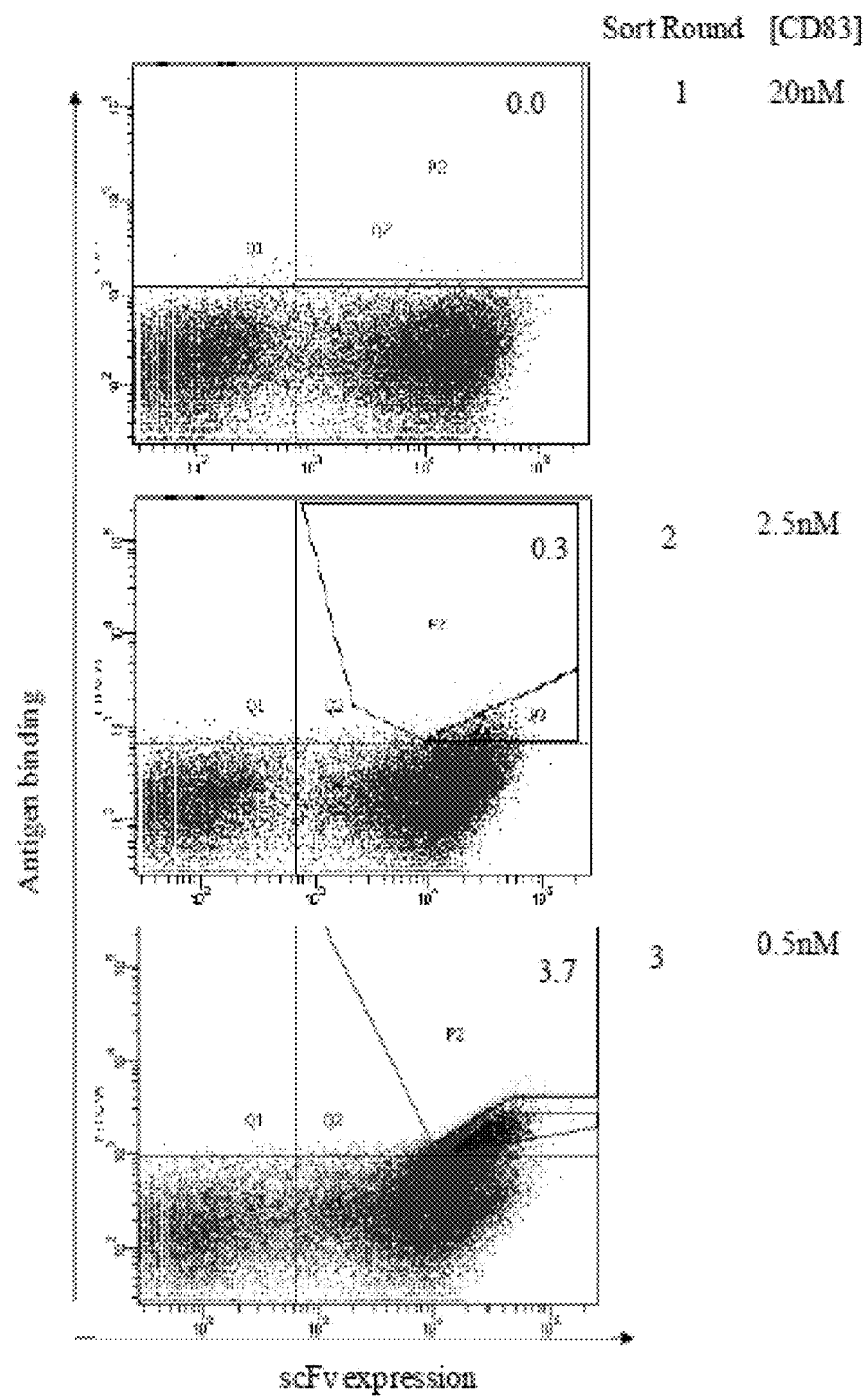
Figure 6:
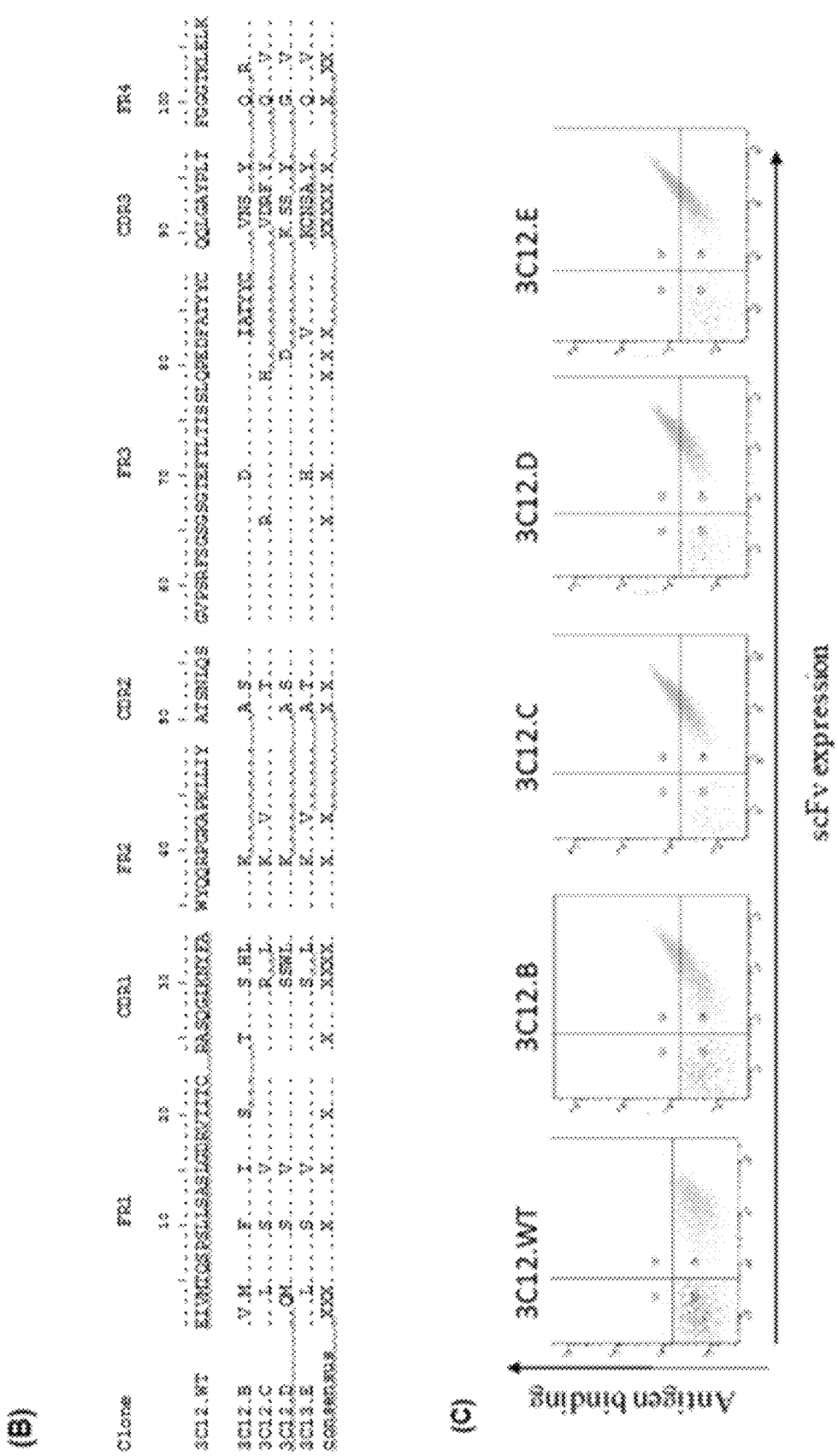

FIG. 6: Selection of scFv with improved affinity for human CD83 from a $V_L$ shuffled library (A) Yeast displaying $V_L$ shuffled 3C12 scFv were stained with hCD83$_{ECD}$-His at the concentrations indicated for each round and sorted into high affinity collection Gate P2 and less stringent Gate P3 for comparison. Percentage of total cells sorted into P2 and P3 are displayed within the gate. Sort Round 3 incorporates selection for clones with slower off-rate. (B) Deduced framework (FR) and complementarity determining regions (CDR) of $V_L$ amino acid sequence alignment of 3C12 and affinity-improved $V_L$ variants. (C) Comparison of monoclonal yeast expressing wildtype (3C12.WT) and affinity-improved 3C12 variants (3C12.B-E) binding to 0.2 nM hCD83$_{ECD}$-His.

Figure 7:
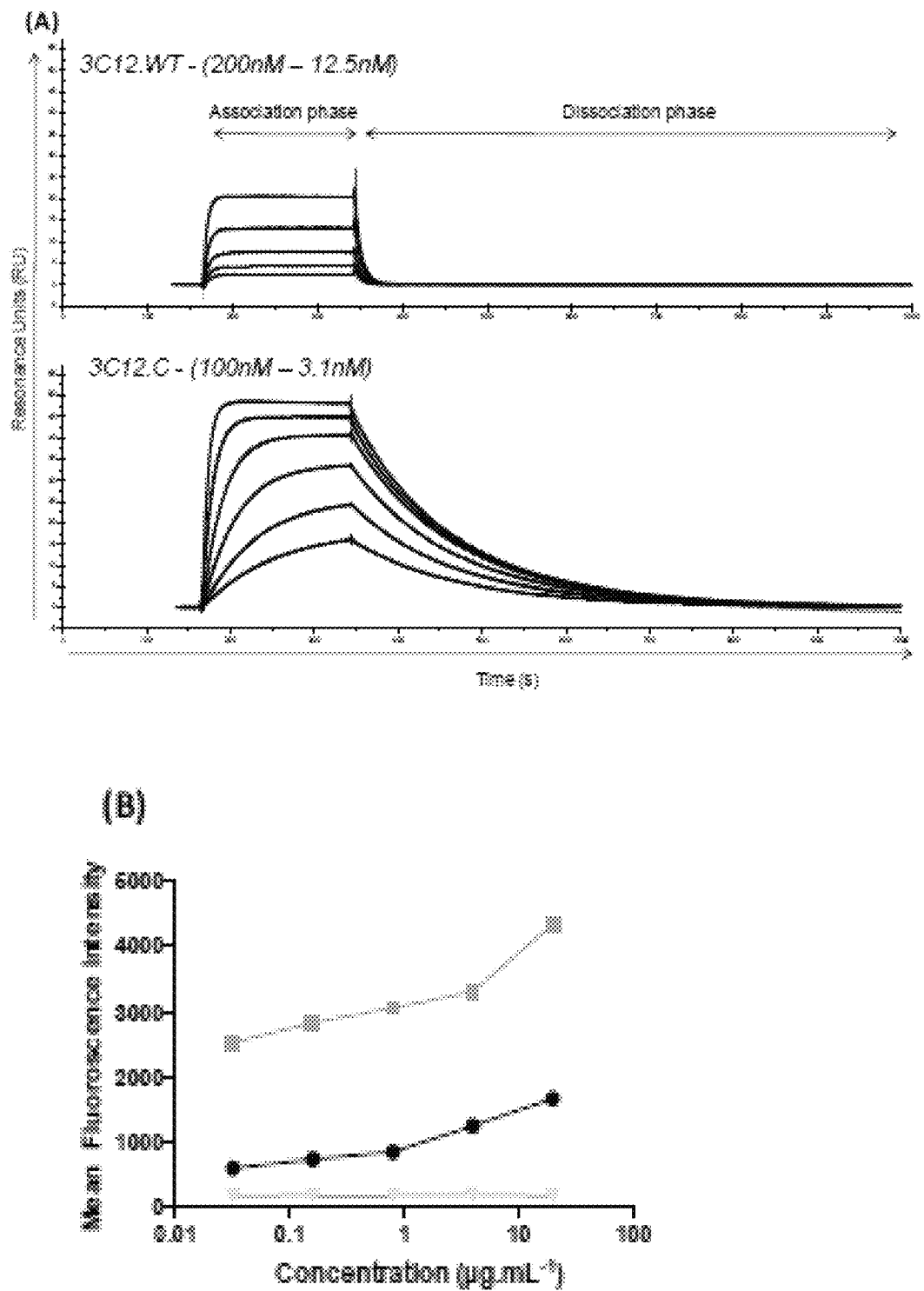

FIG. 7: Characterization of reformatted 3C12 $V_L$ shuffled variant Fabs (A) BiaCore traces show binding of 3C12.WT (upper panel) and 3C12.C (lower panel) Fab fragments to immobilised hCD83$_{ECD}$-Fc during the constant injection of Fab for 3 mins (180s; Association Phase) followed by injection of buffer for 10 mins (600s; Dissociation Phase). Two-fold dilutions of Fab were prepared over the concentration series specified. (B) Dilution series of 3C12.WT (circles), 3C12.C (squares) and IgG isotype control (triangles) binding to CD83$^+$ cell line, KM-H2.

Figure 8:
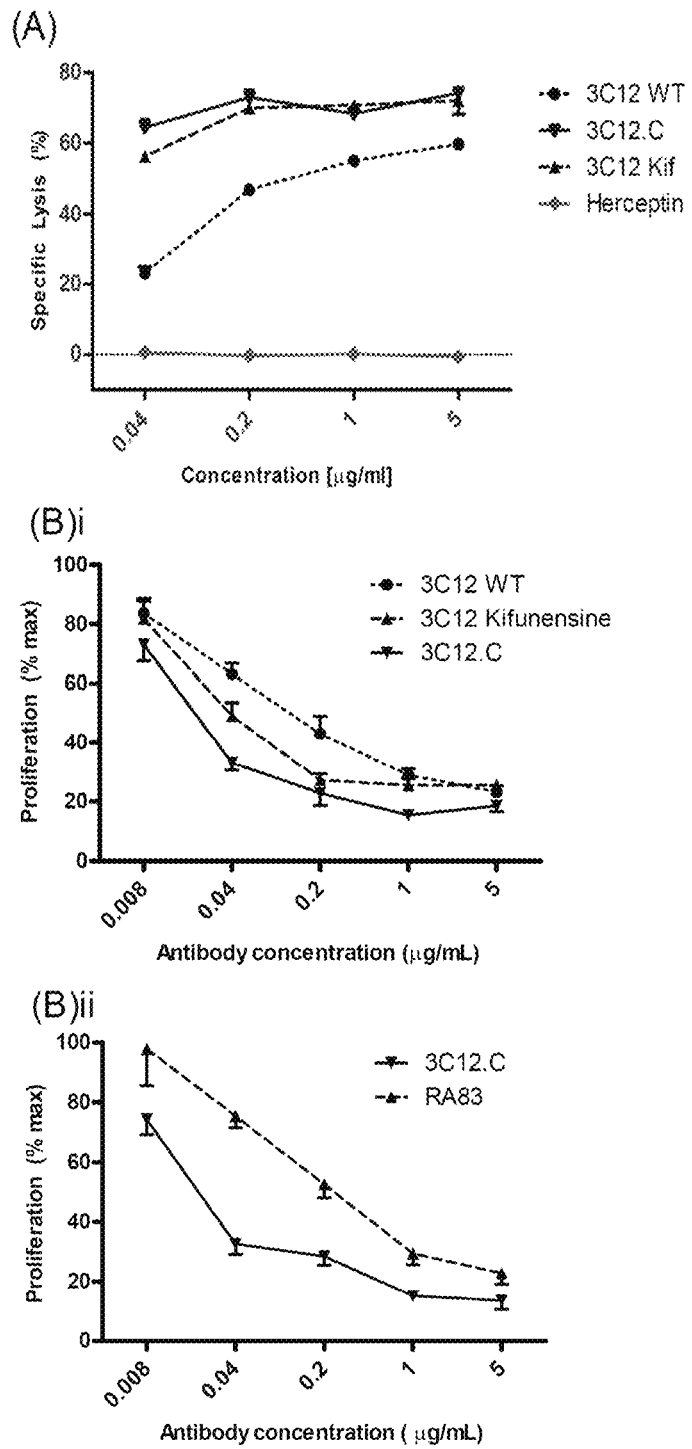

FIG. 8: Glycomodification and affinity maturation enhance in vitro activity of CD83mAb Comparative potency of 3C12.WT, 3C12.C, and 3C12.kif in vitro. (A) Specific lysis of CD83 transfected BB88 cells after 4 hours incubation at 37° C. with antibody and NK cells (5:1 effector to target cell ratio). Herceptin=human IgG1κ isotype control. (B) Anti-proliferative effects of (i) 3C12 variants and (ii) in comparison to RA83 in two-way MLR. Data shown is the average±SEM of five replicates, representative of 2-4 independent experiments.

Figure 9:
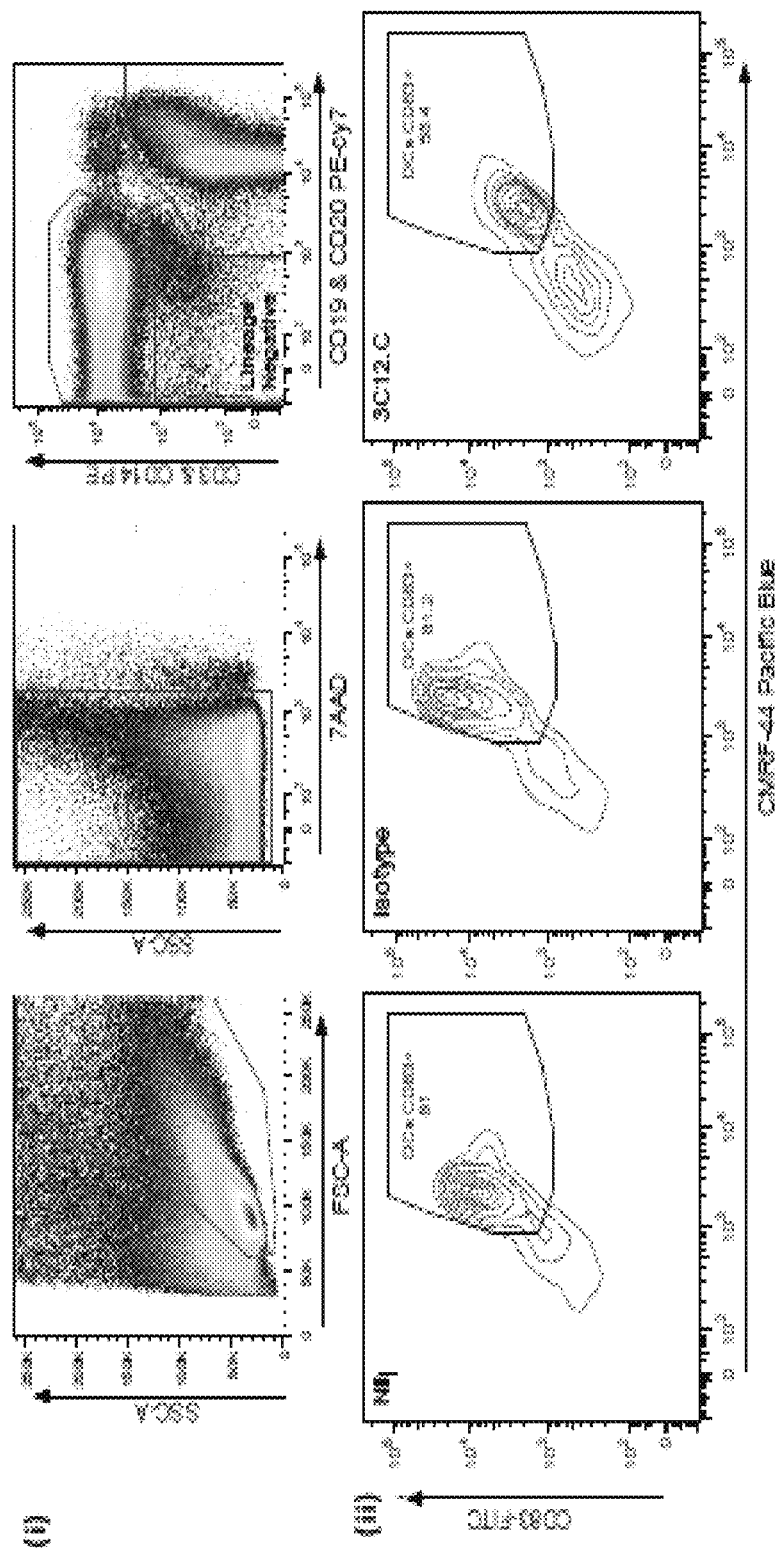

FIG. 9: CD83 bright blood dendritic cells are targeted by engineered anti-CD83 mAb in vitro Effect on blood DCs after culturing PBMC with 5 µg·mL$^{-1}$ 3C12.C, human IgG1K isotype control or nil antibody treatment over three days. (i) Live (7AAD), activated blood DCs are defined as Lineage$^-$ HLA-DR$^+$ (HLA-DR gating not shown) cells (=total DC) which co-express CMRF-44 and CD83. (ii) The number within the activated DC gate is the percentage of total DCs. Each experimental condition was performed in triplicate and the results presented are representative of 4 independent experiments.

Figure 10:
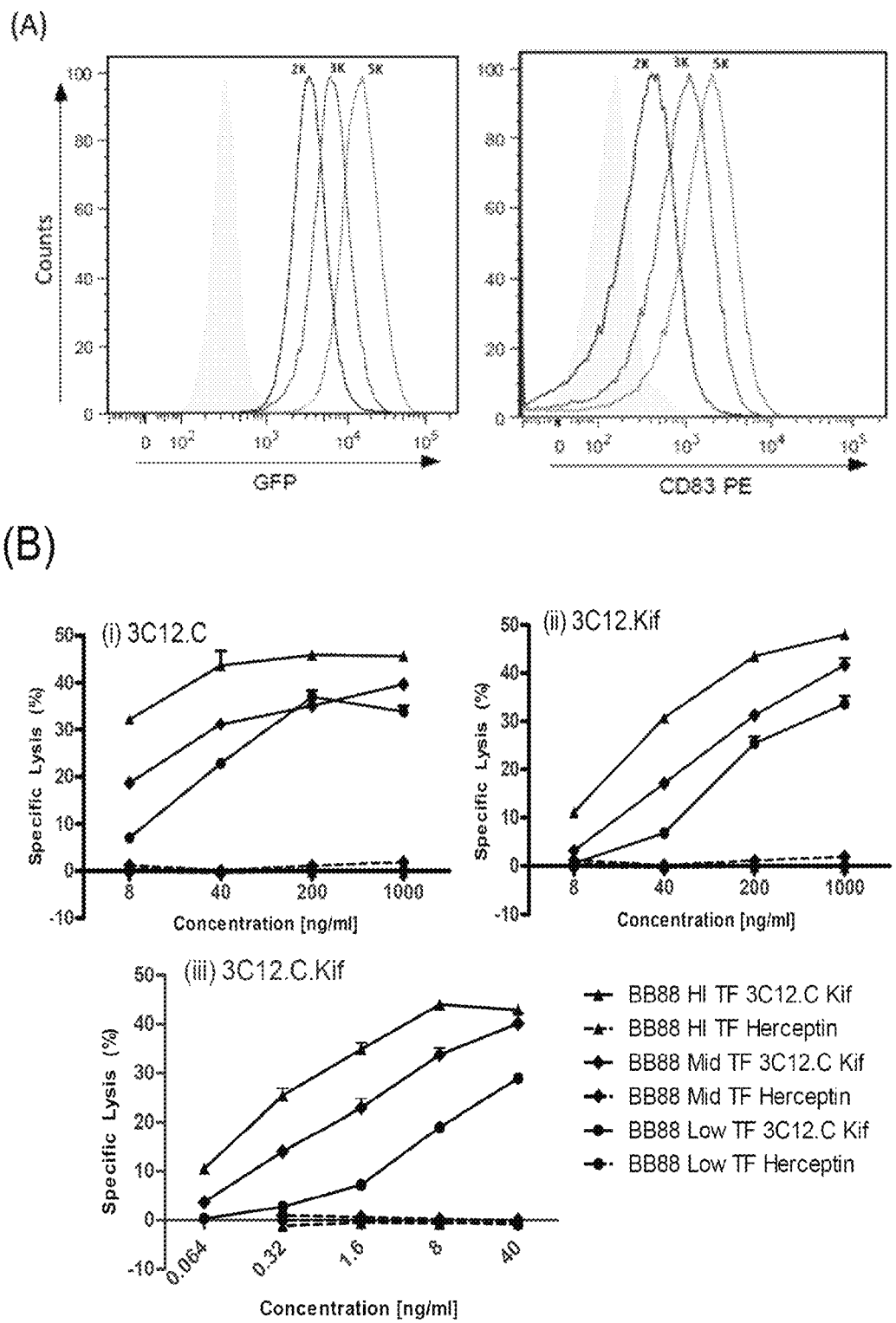

FIG. 10: Density of CD83 antigen correlates with GFP expression levels and in vitro ADCC potency Characterization of BB88 transfectants with varying levels of CD83 expression; BB88-CD83-TF.5K (5,400 MPC), BB88-CD83TF.3K (3,600 MPC), or BB88-CD83TF.2K (<2, 300 MPC). (A) Expression levels of GFP (left) and CD83 detected by HB15a on BB88 transfectants (right). (B) ADCC induced in a chromium release assay by (i) 3C12.C, (ii) 3C12.Kif or (iii) 3C12.C.Kif on BB88 transfectants at an effector to target cell ratio of 5:1. Data is displayed as the mean±SEM of five replicates and the results presented are representative of 2 independent experiments.

Figure 11:
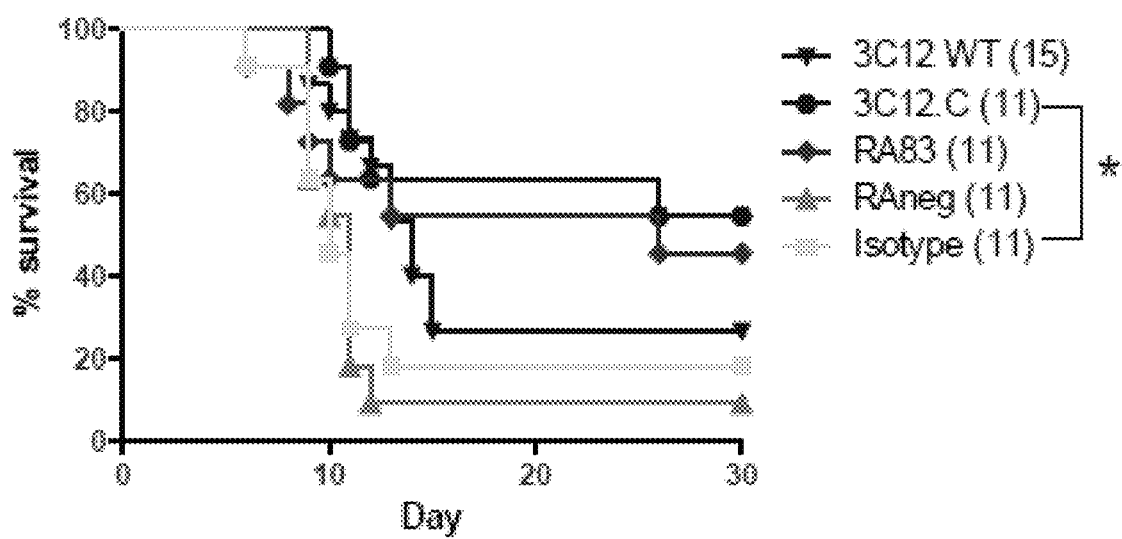

FIG. 11: 3C12.C has equivalent potency to RA83 in vivo

Survival of SCID mice after xenogeneic human PBMC transplant and administration of 0.125 mg CD83 antibody or isotype matched antibody controls at Day 0. Data displayed is pooled from two experiments that used different human PBMC donors (total number of animals used in each cohort is displayed in brackets following cohort descriptions). Significant differences (p<0.05) are asterisked.

SEQUENCE LISTING

| | |
|---|---|
| SEQ ID NO: 1 | amino acid sequence of 3C12 heavy chain variable region |
| SEQ ID NO: 2 | CDR1 of 3C12 heavy chain variable region |
| SEQ ID NO: 3 | CDR2 of 3C12 heavy chain variable region |
| SEQ ID NO: 4 | CDR3 of 3C12 heavy chain variable region |
| SEQ ID NO: 5 | amino acid sequence of 3C12 light chain variable region |
| SEQ ID NO: 6 | amino acid sequence of 3C12.B light chain variable region |
| SEQ ID NO: 7 | amino acid sequence of 3C12.C light chain variable region |
| SEQ ID NO: 8 | amino acid sequence of 3C12.D light chain variable region |
| SEQ ID NO: 9 | amino acid sequence of 3C12.E light chain variable region |
| SEQ ID NO: 10 | amino acid sequence of V$_L$ consensus sequence of 3C12 and derivatives |
| SEQ ID NO: 11 | CDR1 of 3C12 light chain variable region |
| SEQ ID NO: 12 | CDR2 of 3C12 light chain variable region |
| SEQ ID NO: 13 | CDR3 of 3C12 light chain variable region |
| SEQ ID NO: 14 | CDR1 of 3C12.B light chain variable region |
| SEQ ID NO: 15 | CDR2 of 3C12.B light chain variable region |
| SEQ ID NO: 16 | CDR3 of 3C12.B light chain variable region |
| SEQ ID NO: 17 | CDR1 of 3C12.C light chain variable region |
| SEQ ID NO: 18 | CDR2 of 3C12.C light chain variable region |
| SEQ ID NO: 19 | CDR3 of 3C12.C light chain variable region |
| SEQ ID NO: 20 | CDR1 of 3C12.D light chain variable region |
| SEQ ID NO: 21 | CDR2 of 3C12.D light chain variable region |
| SEQ ID NO: 22 | CDR3 of 3C12.D light chain variable region |
| SEQ ID NO: 23 | CDR1 of 3C12.E light chain variable region |
| SEQ ID NO: 24 | CDR2 of 3C12.E light chain variable region |
| SEQ ID NO: 25 | CDR3 of 3C12.E light chain variable region |
| SEQ ID NO: 26 | amino acid sequence of V$_L$ consensus sequence of CDR1 of 3C12 and derivatives |
| SEQ ID NO: 27 | amino acid sequence of V$_L$ consensus sequence of CDR2 of 3C12 and derivatives |
| SEQ ID NO: 28 | amino acid sequence of V$_L$ consensus sequence of CDR3 of 3C12 and derivatives |
| SEQ ID NO: 29 | amino acid sequence of 3C12 heavy chain |
| SEQ ID NO: 30 | amino acid sequence of 3C12 light chain |
| SEQ ID NO: 31 | amino acid sequence of 3C12.B light chain |
| SEQ ID NO: 32 | amino acid sequence of 3C12.C light chain |
| SEQ ID NO: 33 | amino acid sequence of 3C12.D light chain |
| SEQ ID NO: 34 | amino acid sequence of 3C12.E light chain |
| SEQ ID NO: 35 | Nucleotide sequence of 3C12 heavy chain variable region |
| SEQ ID NO: 36 | Nucleotide sequence of 3C12 light chain variable region |
| SEQ ID NO: 37 | Nucleotide sequence of 3C12.B light chain variable region |
| SEQ ID NO: 38 | Nucleotide sequence of 3C12.C light chain variable region |
| SEQ ID NO: 39 | Nucleotide sequence of 3C12.D light chain variable region |
| SEQ ID NO: 40 | Nucleotide sequence of 3C12.E light chain variable region |
| SEQ ID NO: 41 | Nucleotide sequence of 3C12 heavy chain |
| SEQ ID NO: 42 | Nucleotide sequence of 3C12 light chain |
| SEQ ID NO: 43 | Nucleotide sequence of 3C12.B light chain |
| SEQ ID NO: 44 | Nucleotide sequence of 3C12.C light chain |
| SEQ ID NO: 45 | Nucleotide sequence of 3C12.D light chain |
| SEQ ID NO: 46 | Nucleotide sequence of 3C12.E light chain |
| SEQ ID NO: 47 | amino acid sequence of human CD83 isoform a |
| SEQ ID NO: 48 | amino acid sequence of human CD83 isoform b |
| SEQ ID NO: 49 | amino acid sequence of human CD83 isoform c |
| SEQ ID NO: 50 | 3C12_VhFor primer |
| SEQ ID NO: 51 | 3C12_VhRev primer |
| SEQ ID NO: 52 | 3C12_VkFor primer |
| SEQ ID NO: 53 | 3C12_VkRev primer |
| SEQ ID NO: 54 | 3C12VH5' primer |
| SEQ ID NO: 55 | Mod3C12VH3' primer |

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al., pp 35-81; Sproat et al., pp 83-115; and Wu et al., pp 135-151; Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara Biochem. Biophys. Res. Commun. 73: 336-342, 1976; Merrifield J. Am. Chem. Soc. 85: 2149-2154, 1963; Barany and Merrifield (1979) in The Peptides (Gross, E. and Meienhofer, J. eds.), vol. 2, pp. 1-284, Academic Press, New York. 12. Wuinsch, E., ed. (1974) Synthese von Peptiden in Houben-Weyls Metoden der Organischen Chemie (Miler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky Int. J. Peptide Protein Res. 25: 449-474, 1985; Handbook of Experimental Immunology, Vols. I-IV (D. M. Weir and C. C. Blackwell, eds., 1986, Blackwell Scientific Publications); and Animal Cell Culture: Practical Approach, 3rd edn (John R. W. Masters, ed., 2000), ISBN 0199637970, whole of text.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

CD83 is a single-pass type I membrane protein and member of the immunoglobulin superfamily. Three human transcript variants encoding different isoforms have been found. For the purposes of nomenclature and not limitation, the amino acid sequences of the human CD83 (hCD83) isoforms are shown in SEQ ID NO:47 (NP_004224.1; isoform a), SEQ ID NO:48 (NP_001035370.1; isoform b) and SEQ ID NO:49 (NP_001238830.1; isoform c). Accordingly, in one example, the amino acid sequence of human CD83 comprises an amino acid sequence as shown in SEQ ID NO:47, 48, or 49. Homologs of CD83 can be found in *Pan troglodytes* (XP_518248.2), *Macaca mulatta* (XP_001093591.1), *Canis lupus familiaris* (XP_852647.1), *Bos Taurus* (NP_001040055.1), *Mus musculus* (NP_033986.1), *Rattus norvegicus* (NP_001101880.1) and *Gallus gallus* (XP_418929.1). Exemplary CD83 binding proteins of the disclosure bind to or bind specifically to hCD83, including recombinant forms thereof (rhCD83).

The term "isolated protein" or "isolated polypeptide" is intended to mean a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, for example, at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antigen binding domain, this term does not encompass an antibody naturally-occurring within a subject's body that is the product of natural recombination that occurs during B cell maturation. However, if such an antibody is isolated, it is to be considered an isolated protein comprising an antigen binding domain. Similarly, if nucleic acid encoding the protein is isolated and expressed using recombinant means, the resulting protein is a recombinant protein comprising an antigen binding domain. A recombinant protein also encompasses a protein expressed by artificial recombinant means when it is within a cell, tissue or subject, for example, in which it is expressed.

The term "CD83 binding protein" shall be taken to include a single polypeptide chain (i.e., a series of contiguous amino acids linked by peptide bonds), or a series of polypeptide chains covalently or non-covalently linked to one another (i.e., a polypeptide complex or protein) capable of binding to CD83 in the manner described and/or claimed herein. For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding domain" shall be taken to mean a region of an antibody that is capable of specifically binding to an antigen, that is, a $V_H$ or a $V_L$ or an Fv comprising both a $V_H$ and a $V_L$. The antigen binding domain need not be in the context of an entire antibody, for example, it can be in isolation (e.g., a domain antibody) or in another form (e.g., scFv).

For the purposes for the present disclosure, the term "antibody" includes a protein capable of specifically binding to one or a few closely related antigens (e.g., CD83) by virtue of an antigen binding domain contained within a Fv. This term includes four chain antibodies (e.g., two light (L) chains and two heavy (H) chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kDa each) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain (CL which is ~110 amino acids in length) is aligned with and disulfide bonded to the first constant domain of the heavy chain ($C_H1$ which is 330 to 440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., IgG1, IgG2, IgG3, IgG4, IgA1 and IgA2) or subclass. In one example, the antibody is a murine (mouse or rat) antibody or a primate (such as, human) antibody. In one example, the antibody is humanized, synhumanized, chimeric, CDR-grafted or deimmunized.

The term "naked antibody" refers to an antibody that is not conjugated to another compound, for example, a toxic compound or radiolabel.

As used herein, "variable region" refers to the portions of the light and/or heavy chains of an antibody as defined herein that is capable of specifically binding to an antigen and, includes amino acid sequences of complementarity determining regions (CDRs), that is, CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs, i.e., CDR1, CDR2, and CDR3) refers to the amino acid residues of an antibody variable region the presence of which are major contributors to specific antigen binding. Each variable region domain ($V_H$ or $V_L$) typically has three CDR regions identified as CDR1, CDR2 and CDR3. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). According to the numbering system of Kabat, $V_H$ FRs and CDRs are positioned as follows: residues 1 to 30 (FR1), 31 to 35 (CDR1), 36 to 49 (FR2), 50 to 65 (CDR2), 66 to 94 (FR3), 95 to 102 (CDR3) and 103 to 113 (FR4). According to the numbering system of Kabat, $V_L$ FRs and CDRs are positioned as follows: residues 1 to 23 (FR1), 24 to 34 (CDR1), 35 to 49 (FR2), 50 to 56 (CDR2), 57 to 88 (FR3), 89 to 97 (CDR3) and 98 to 107 (FR4). The present disclosure is not limited to FRs and CDRs as defined by the Kabat numbering system, but includes all numbering systems, including the canonical numbering system or of Chothia and Lesk J. Mol. Biol. 196: 901-917, 1987; Chothia et al., Nature 342: 877-883, 1989; and/or Al-Lazikani et al., J. Mol. Biol. 273: 927-948, 1997; the numbering system of Honnegher and Pltikthun J. Mol. Biol. 309: 657-670, 2001; or the IMGT system discussed in Giudicelli et al., Nucleic Acids Res. 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In an additional, or alternative, option, light chain CDR1 does not comprise the four N-terminal amino acids listed herein or any one or more of those amino acids are substituted with another naturally-occurring amino acid. In this regard, Padlan et al., FASEB J., 9: 133-139, 1995 established that the five C-terminal amino acids of heavy chain CDR2 and/or the four N-terminal amino acids of light chain CDR1 are not generally involved in antigen binding.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain that is capable of specifically binding to an antigen. The $V_H$ and the $V_L$ which form the antigen binding domain can be in a single polypeptide chain or in different polypeptide chains. Furthermore, a Fv of the disclosure (as well as any protein of the disclosure) may have multiple antigen binding domains which may or may not bind the same antigen. This term shall be understood to encompass fragments directly derived from an antibody as well as proteins corresponding to such a fragment produced using recombinant means.

In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, for example, $C_H2$ or $C_H3$ domain, for example, a minibody.

A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means.

A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means.

A "F(ab')$_2$ fragment" of an antibody consists of a dimer of two Fab' fragments held together by two disulfide bonds, and is obtained by treating a whole antibody molecule with the enzyme pepsin, without subsequent reduction.

A "Fab$_2$" fragment is a recombinant fragment comprising two Fab fragments linked using, for example, a leucine zipper or a $C_H3$ domain.

A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a CD83 binding protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the antibody, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein that specifically binds to an antigen binds that antigen with greater affinity, avidity, more readily, and/or with greater duration than it binds to other antigens. For example, a protein binds to CD83 (e.g., hCD83) with materially greater affinity than it does to other immunoglobulin superfamily ligands or to antigens commonly recognized by polyreactive natural antibodies (i.e., by naturally occurring antibodies known to bind a variety of antigens naturally found in humans). It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". In one example, "specific binding" of a CD83 binding protein of the disclosure to an antigen, means that the protein binds to the antigen with an equilibrium constant ($K_D$) of 100 nM or less, such as 50 nM or less, for example, 20 nM or less, such as, 15 nM or less or 10 nM or less or 5 nM or less or 1 nM or less or 500 pM or less or 400 pM or less or 300 pM or less or 200 pM or less or 100 pM or less.

As used herein, the term "epitope" (syn. "antigenic determinant") shall be understood to mean a region of CD83 to which a protein comprising an antigen binding domain of an antibody binds. This term is not necessarily limited to the specific residues or structure to which the protein makes contact. For example, this term includes the region spanning amino acids contacted by the protein and/or at least 5 to 10 or 2 to 5 or 1 to 3 amino acids outside of this region. In some examples, the epitope is a linear series amino acids. An epitope may also comprise a series of discontinuous amino acids that are positioned close to one another when CD83 is folded, that is, a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics. An epitope or peptide or polypeptide comprising same can be administered to an animal to generate antibodies against the epitope.

The term "competitively inhibits" shall be understood to mean that a CD83 binding protein of the disclosure reduces or prevents binding of a recited antibody to CD83, for example, to hCD83. This may be due to the protein (or antigen binding domain) binding to the same or an overlapping epitope as the antibody. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, the antibody is exposed to CD83 either in the presence or absence of the protein. If less antibody binds in the presence of the protein than in the absence of the protein, the protein is considered to competitively inhibit binding of the antibody. In one example, the competitive inhibition of binding is caused by the antigen binding domain of the protein on CD83 overlapping with the antigen binding domain of the antibody.

"Overlapping" in the context of two epitopes means that two epitopes share a sufficient number of amino acid residues to permit a binding protein of the disclosure that binds to one epitope to competitively inhibit the binding of a recited antibody to CD83 that binds to the other epitope. For example, the "overlapping" epitopes share at least 1 or 2 or 3 or 4 or 5 or 6 or 7 or 8 or 9 or 10 or 11 or 12 or 13 or 14 or 15 or 16 or 17 or 18 or 19 or 20 amino acids.

As used herein, a "CD83 associated condition or disease" refers to any condition or disease that is caused by or associated with CD83 or a cell expressing CD83. The skilled artisan will be readily able to determine such conditions or diseases based on the disclosure herein and/or by performing an assay to diagnose a CD83 associated condition or disease. In this regard, in some examples the condition or disease is an inflammatory condition or disease, or an autoimmune condition or disease. A description of exemplary conditions and diseases is included herein.

As used herein, the terms "preventing", "prevent" or "prevention" include administering a protein of the disclosure to thereby stop or hinder the development of at least one symptom of a condition or disease. This term also encompasses treatment of a subject in remission to prevent or hinder relapse. For example, a subject suffering from relapsing-remitting multiple sclerosis is treated during remission to thereby prevent a relapse.

As used herein, the terms "treating", "treat" or "treatment" include administering a protein described herein to thereby reduce or eliminate at least one symptom of a specified condition or disease.

As used herein, the term "subject" shall be taken to mean any animal, such as, a mammal. In one example, the mammal is a human or non-human primate. In one example, the mammal is a human.

Reference herein to a "sample" should be understood as a reference to any sample derived from a subject such as, but not limited to, a body fluid (e.g., blood or blood fraction such as serum or plasma, tears, urine, synovial fluid or cerebrospinal fluid), cellular material (e.g. tissue aspirate), tissue biopsy specimens or surgical specimens. In some examples, the "sample" is any one or more of serum, plasma, PBMCs, or a buffy coat fraction.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease, including the chance of recovery or recurrence or the outcome of treatment.

The term "expression construct" is to be taken in its broadest context and includes a nucleic acid comprising one or more promoter sequences operably linked with one or more nucleic acids as described herein.

The term "expression vector" refers to a nucleic acid comprising an expression construct that is additionally capable of maintaining and or replicating nucleic acid in an expressible format. For example, an expression vector may comprise a plasmid, bacteriophage, phagemid, cosmid, virus sub-genomic or genomic fragment. Selection of appropriate vectors is within the knowledge of those having skill in the art.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, for example, in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter. A promoter can be operably linked to numerous nucleic acids, for example, through an internal ribosome entry site.

Proteins Comprising Antigen Binding Domains
Antibodies
Library-Based Methods

The present disclosure also encompasses screening of libraries of antibodies or proteins comprising antigen binding domains thereof (e.g., comprising variable regions thereof) to identify a CD83 binding protein of the disclosure. For example, a library comprising a $V_H$ of the disclosure and a plurality of $V_L$ regions can be screened to identify a CD83 binding protein of the disclosure.

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG), U.S. Pat. Nos. 5,885,793, 6,204,023, 6,291,158, or U.S. Pat. No. 6,248,516.

The CD83 binding proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, for example, as described in U.S. Pat. Nos. 6,300,064, 5,885,793, 6,204,023, 6,291,158, or U.S. Pat. No. 6,248,516. Other phage display methods are known in the art and are contemplated by the present disclosure. Similarly, methods of cell display are contemplated by the disclosure, for example, bacterial display libraries, for example, as described in U.S. Pat. No. 5,516,637; yeast display libraries, for example, as described in U.S. Pat. No. 6,423,538; or a mammalian display library.

Methods for screening display libraries are known in the art. In one example, a display library of the present disclosure is screened using affinity purification, for example, as described in Scopes (In: Protein purification: principles and practice, Third Edition, Springer Verlag, 1994). Methods of affinity purification typically involve contacting proteins comprising antigen binding domains displayed by the library with a target antigen (e.g., CD83) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., J. Immunol. Methods 354: 85-90, 2010; or Jostock et al., J. Immunol. Methods, 289: 65-80, 2004. Alternatively, or additionally, standard cloning methods are used, e.g., as described in Ausubel et al., (In: Current Protocols in Molecular Biology. Wiley Interscience, ISBN 047 150338, 1987), and/or (Sambrook et al., (In: Molecular Cloning: Molecular Cloning: A Laboratory Manual, Cold Spring Harbor Laboratories, New York, Third Edition 2001).

In one example, the present disclosure provides a method of producing or isolating a CD83 binding protein of the disclosure by screening a display library, for example, a phage display library, for example, as described in U.S. Pat. No. 6,300,064 and/or U.S. Pat. No. 5,885,793. For example, the present inventors have isolated scFvs by biopanning a human scFv immunoglobulin gene library by three rounds of selection against recombinant extracellular domain of human CD83. Once isolated, a CD83 binding protein of the invention can be cloned and expressed and optionally reformatted as, for example, an IgG1 antibody using known methods in the art.

In one example, the present disclosure provides a method of producing a CD83 binding protein, the method comprising:
(i) screening a CD83 binding protein preparation or library for a binding protein that binds to the extracellular domain of CD83, for example, the extracellular domain of recombinant human CD83; and
(ii) isolating a CD83 binding protein having a desired binding affinity for the extracellular domain of CD83.

In one example, a CD83 binding protein preparation is screened. A CD83 preparation may be made by, for example, immunizing an animal with a CD83 antigen so as to produce antibodies that react with the extracellular domain of CD83.

In another example, a CD83 binding protein library is screened. The library may be a phage library, for example, a scFv phage library or a Fab phage library.

In one example, the method comprises producing a population of phage particles displaying at their surface a population of binding molecules having a range of binding specificities for a target CD83 epitope or antigen. Such phage particles comprise a phagemid genome comprising a nucleic acid encoding the binding protein. This nucleic acid can be isolated, cloned and expressed in a recombinant system to produce the CD83 binding protein of the invention.

Deimmunized, Chimeric, Humanized, Synhumanized, Primatized, Human and Composite CD83 Binding Proteins The CD83 binding proteins of the present disclosure may be CDR grafted proteins which include CDRs from an antibody from a non-human species (e.g., mouse or rat or non-human primate) grafted onto or inserted into FRs from a human antibody or which include CDRs from an antibody from one type of antibody (e.g., one type of human antibody) grafted onto or inserted into FRs from another type of antibody (e.g., another type of human antibody). This term also encompasses a composite protein comprising, for example, one or more CDR grafted variable regions and one or more, for example, human variable regions, chimeric variable regions, synhumanized variable regions, or primatized variable regions.

The CD83 binding proteins of the present disclosure may be humanized proteins.

The term "humanized protein" shall be understood to refer to a protein comprising a human-like variable region, which includes CDRs from an antibody from a human species (e.g., mouse or rat or non-human primate) grafted onto or inserted into FRs from a non-human antibody (this type of antibody is also referred to as a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, for example, as described in U.S. Pat. Nos. 5,225,539, 6,054,297, 7,566,771, or U.S. Pat. No. 5,585,089. The term "humanized protein" also encompasses a super-humanized protein, for example, as described in U.S. Pat. No. 7,732,578. This term also encompasses a composite protein comprising, for example, one or more humanized variable regions and one or more, for example, human variable regions, chimeric variable regions, synhumanized variable regions or primatized variable regions.

In one example, a humanized CD83 binding protein comprises the regions between 27d and 34, 50 and 55, and 89 and 96 in a light chain sequence disclosed herein; and 31 and 35b, 50 and 58, and 95 and 101 in a heavy chain sequence disclosed herein (numbering according to the Kabat numbering system). In this regard, Padlan et al., FASEB J., 9: 133-139, 1995 presents evidence that these regions are those most likely to bind or contact antigen.

The CD83 binding proteins of the present disclosure may be human proteins. The term "human protein" as used herein refers to proteins having variable and, optionally, constant antibody regions found in humans, for example, in the human germline or somatic cells or from libraries produced using such regions. The "human" antibodies can include amino acid residues not encoded by human sequences, for example, mutations introduced by random or site directed mutations in vitro (in particular mutations which involve conservative substitutions or mutations in a small number of residues of the protein, for example, in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, for example, as described in U.S. Pat. No. 6,300,064 and/or U.S. Pat. No. 6,248,516.

Exemplary human CD83 binding proteins are antibodies comprising the following pairs of variable regions:
 (i) a $V_H$ sequence as shown in SEQ ID NO:1 and a $V_L$ sequence as shown in SEQ ID NO:5; or
 (ii) a $V_H$ sequence as shown in SEQ ID NO:1 and a $V_L$ sequence as shown in SEQ ID NO:6;
 (iii) a $V_H$ sequence as shown in SEQ ID NO:1 and a $V_L$ sequence as shown in SEQ ID NO:7; or
 (iv) a $V_H$ sequence as shown in SEQ ID NO:1 and a $V_L$ sequence as shown in SEQ ID NO:8; or
 (v) a $V_H$ sequence as shown in SEQ ID NO:1 and a $V_L$ sequence as shown in SEQ ID NO:9.

In one example, the $V_L$ sequence lacks the c-terminal lysine residue. The C-terminal lysine of the $V_L$ sequence of a CD83 binding protein of the disclosure may be removed, for example, during production or purification of the CD83 binding protein, or by recombinantly engineering the nucleic acid encoding the $V_L$ of the CD83 binding protein. Accordingly, CD83 binding proteins may comprise populations with all C-terminal lysine residues of the $V_L$ removed, populations with no C-terminal lysine residues of the $V_L$ removed, or populations having a mixture of proteins with and without the $V_L$ C-terminal lysine residue. In some examples, the protein populations may additionally comprise proteins having two VLs in which the C-terminal lysine residue is removed in one of the VLs. Similarly, a composition of proteins may comprise the same or a similar mix of protein populations with or without the $V_L$ C-terminal lysine residue.

Optionally, the $V_H$ is linked to a heavy chain constant region, for example, an IgG1 heavy chain constant region. In one example, the heavy chain constant region lacks the c-terminal lysine residue.

Optionally, the $V_L$ is linked to a light chain constant region.

The CD83 binding proteins of the present disclosure may be synhumanized proteins. The term "synhumanized protein" refers to a protein prepared by a method described in US20080095767. A synhumanized CD83 binding protein includes a variable region of an antibody, wherein the variable region comprises FRs from a New World primate antibody variable region and CDRs from a non-New World primate antibody variable region. For example, a synhumanized CD83 binding protein includes a variable region of an antibody, wherein the variable region comprises FRs from a New World primate antibody variable region and CDRs from a mouse or rat antibody. In one example, the synhumanized CD83 binding protein is a CD83 binding antibody in which one or both of the variable regions are synhumanized. This term also encompasses a composite protein comprising, for example, one or more synhumanized variable regions and one or more, for example, human variable regions or humanized variable regions or chimeric variable regions.

The CD83 binding proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898. This term also encompasses a composite protein comprising, for example, one or more primatized variable regions and one or more, for example, human variable regions or humanized variable regions or chimeric variable regions.

In one example, a CD83 binding protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397). This term also encompasses a composite protein comprising, for example, one or more chimeric variable regions and one or more, e.g., human variable regions or humanized variable regions or chimeric variable regions.

The present disclosure also contemplates a deimmunized CD83 binding protein, for example, as described in WO2000/34317 and US20070292416. De-immunized antibodies and proteins have one or more epitopes, for example, B cell epitopes or T cell epitopes removed (i.e., mutated) to thereby reduce the likelihood that a subject will raise an immune response against the antibody or protein. For example, a CD83-binding protein of the disclosure is analyzed to identify one or more B or T cell epitopes and one or more amino acid residues within the epitope is mutated to thereby reduce the immunogenicity of the CD83 binding protein.

It will be apparent to the skilled artisan from the foregoing disclosure that a "composite" protein comprises one form of $V_H$ (e.g., human) and another form of $V_L$ (e.g., humanized). The present disclosure explicitly encompasses all combinations of forms of $V_H$ and $V_L$.

Other CD83 Binding Proteins Comprising an Antigen Binding Domain

The present disclosure also contemplates other CD83 binding proteins comprising a variable region or antigen binding domain of an antibody, such as:

(i) a single-domain antibody, which is a single polypeptide chain comprising all or a portion of the $V_H$ or a $V_L$ of an antibody, for example, as described in U.S. Pat. No. 6,248,516);

(ii) diabodies, triabodies and tetrabodies, for example, as described in U.S. Pat. No. 5,844,094 and/or US2008152586;

(iii) scFvs, for example, as described in U.S. Pat. No. 5,260,203;

(iv) minibodies, for example, as described in U.S. Pat. No. 5,837,821;

(v) "key and hole" bispecific proteins, for example, as described in U.S. Pat. No. 5,731,168;

(vi) heteroconjugate proteins, for example, as described in U.S. Pat. No. 4,676,980; (vii) heteroconjugate proteins produced using a chemical cross-linker, for example, as described in U.S. Pat. No. 4,676,980;

(viii) Fab'-SH fragments, for example, as described in Shalaby et al., J. Exp. Med., 175: 217-225, 1992; or (ix) Fab3, for example, as described in EP19930302894.

Constant Domain Fusions

The present disclosure encompasses CD83 binding proteins comprising an antigen binding domain of an antibody and a constant region or Fc or a domain thereof, for example, $C_H2$ and/or $C_H3$ domain. Suitable constant regions and/or domains will be apparent to the skilled artisan and/or the sequences of such polypeptides are readily available from publicly available databases. Kabat et al. also provide description of some suitable constant regions/domains.

Constant regions and/or domains thereof are useful for providing biological activities such as, dimerization, extended serum half life (e.g., by binding to FcRn), antibody-dependent cell cytotoxicity (ADCC), complement dependent cytotoxicity (CDC), antibody-dependent cell phagocytosis (ADCP).

The present disclosure also contemplates CD83 binding proteins comprising mutant constant regions or domains, for example, as described in U.S. Pat. Nos. 7,217,797; 7,217,798; or US20090041770 (having increased half-life) or U.S. Pat. No. 7,355,008 (increased ADCC).

The C-terminal lysine of the heavy chain constant region of a CD83 binding protein of the disclosure comprising a constant region or Fc may be removed, for example, during production or purification of the CD83 binding protein, or by recombinantly engineering the nucleic acid encoding a heavy chain of the CD83 binding protein. Accordingly, CD83 binding proteins may comprise populations with all C-terminal lysine residues of the heavy chain constant region removed, populations with no C-terminal lysine residues of the heavy chain constant region removed, or populations having a mixture of proteins with and without the heavy chain constant region C-terminal lysine residue. In some examples, the protein populations may additionally comprise proteins having two heavy chain constant regions in which the heavy chain constant region C-terminal lysine residue is removed in one of the heavy chain constant regions. Similarly, a composition of proteins may comprise the same or a similar mix of protein populations with or without the heavy chain constant region C-terminal lysine residue.

Enhancing Effector Function

In one example, a CD83 binding protein of the present disclosure may induce effector function or enhanced effector function.

In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies include: complement dependent cytotoxicity (CDC); antibody-dependent-cell-mediated cytotoxicity (ADCC); antibody-dependent-cell-phagocytosis (ADCP); and B-cell activation.

"Antibody-dependent-cell-mediated cytotoxicity" or "ADCC" refers to lysis of antibody coated target cells by effector cells (e.g., natural killer ("NK") cells, neutrophils and macrophages) having Fc receptors that recognize the Fc region of the bound antibody. To assess ADCC activity of a molecule of interest, an in vitro ADCC assay may be performed. Useful effector cells for such assays include peripheral blood mononuclear cells ("PBMC") and NK cells.

In one example, a CD83 binding protein of the present disclosure binds to CD83 on the surface of a cell in such a manner that it is capable of inducing an effector function, such as, ADCC and/or CDC.

For example, the CD83 binding protein remains bound to the CD83 on the surface of the cell for a time sufficient to induce an effector function, such as ADCC and/or CDC.

In one example, a CD83 binding protein of the present disclosure is capable of inducing enhanced effector function, for example, by virtue of a modified Fc region or by virtue of comprising a region capable of binding to an immune effector cell. For example, the level of effector function is increased compared to the level induced by a human IgG1 or IgG3 Fc region. Enhancing effector function induced by a CD83 binding protein of the disclosure may result in enhanced therapeutic or prophylactic effects, for example, by killing or depleting cells causing a condition, for example, antigen presenting cells (APC) (e.g., dendritic cells (DCs)) and/or lymphocytes (e.g., T cells) that modulate aberrant or unwanted immune responses in, for example, inflammatory and/or autoimmune conditions or diseases. In one example, enhancing effector function prevents allogeneic stimulation of T cells, by for example, killing or depleting CD83+ cells that stimulate allogeneic T cells.

In one example, the Fc region of a CD83 binding protein of the disclosure is modified to increase the level of effector function it is capable of inducing compared to the Fc region without the modification. Such modifications can be at the amino acid level and/or the secondary structural level and/or the tertiary structural level and/or to the glycosylation of the Fc region.

The skilled addressee will appreciate that greater effector function may be manifested in any of a number of ways, for example as a greater level of effect, a more sustained effect or a faster rate of effect.

In one example, the Fc region comprises one or more amino acid modifications that increase its ability to induce enhanced effector function. In one example, the Fc region binds with greater affinity to one or more FcγRs, such as FcγRIII. In one example, the Fc region comprise at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the Fc region comprises the following amino acid substitutions S239D/I332E, numbered according to the EU index of Kabat. This Fc region has about 14 fold increase in affinity for FcγRIIIa compared to a wild-type Fc region and about 3.3 increased ability to induce ADCC compared to a wild-type Fc region. In one example, the Fc region comprises the following amino acid substitutions S239D/A330L/I332E, numbered according to the EU index of Kabat. This Fc region has about 138 fold increase in affinity for FcγRIIIa compared to a wild-type Fc region and about 323 fold increased ability to induce ADCC compared to a wild-type Fc region.

Additional amino acid substitutions that increase ability of a Fc region to induce effector function are known in the art and/or described, for example, in U.S. Pat. Nos. 6,737,056 or 7,317,091.

In one example, the glycosylation of the Fc region is altered to increase its ability to induce enhanced effector function. In this regard, native antibodies produced by mammalian cells typically comprise a branched, biantennary oligosaccharide that is generally attached by an N-linkage to Asn297 of the $C_H2$ domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some examples, Fc regions according to the present disclosure comprise a carbohydrate structure that lacks fucose attached (directly or indirectly) to an Fc region, that is, the Fc region is "defucosylated" or "afucosylated". Such variants may have an improved ability to induce ADCC. Methods for producing defucosylated antibodies include, expressing the antibody or antigen binding fragment thereof in a cell line incapable of expressing α-1,6-fucosyltransferase (FUT8) (e.g., as described in Yumane-Ohnuki et al., Biotechnol. Bioengineer. 87: 614-622, 2004), expressing the antibody or antigen binding fragment thereof in cells expressing a small interfering RNA against FUT8 (e.g., as described in Mori et al., Biotechnol. Bioengineer., 88: 901-908, 2004), expressing the antibody or antigen binding fragment thereof in cells incapable of expressing guanosine diphosphate (GDP)-mannose 4,6-dehydratase (GMD) (e.g., as described in Kanda et al., J. Biotechnol., 130: 300-310, 2007). The present disclosure also contemplates the use of antibody or antigen binding fragment thereof having a reduced level of fucosylation, for example, produced using a cell line modified to express β-(1,4)-N-acetylglucosaminyltransferase III (GnT-III) (e.g., as described in Umãna et al., Nat. Biotechnol. 17: 176-180, 1999).

In one example, an antibody according to the present disclosure is defucosylated. For example, the antibody is produced in a cell (e.g., a mammalian cell, such as a CHO cell) that does not express FUT8 or is treated with an inhibitor of N-glycan processing such as kifunensine.

Other methods include the use of cell lines which inherently produce antibodies capable of inducing enhanced Fc-mediated effector function (e.g., duck embryonic derived stem cells for the production of viral vaccines, US20100062489; Recombinant protein production in avian EBX® cells, US20100226912).

CD83 binding proteins of the present disclosure also include those with bisected oligosaccharides, for example, in which a biantennary oligosaccharide attached to the Fc region is bisected by GlcNAc. Such immunoglobulins may have reduced fucosylation and/or improved ADCC function. Examples of such antibody or antigen binding fragment thereof are described, for example, in U.S. Pat. No. 6,602,684 and US20050123546.

CD83 binding proteins with at least one galactose residue in the oligosaccharide attached to the Fc region are also contemplated. Such immunoglobulins may have improved CDC function. Such immunoglobulins are described, for example, in WO1997/30087 and WO1999/22764.

CD83 binding proteins can also comprise a Fc region capable of inducing enhanced levels of CDC. For example, hybrids of IgG1 and IgG3 produce antibodies having enhanced CDC activity (Natsume et al., Cancer Res. 68: 3863-3872, 2008).

CD83 binding proteins can also or alternatively be fused to or conjugated to proteins (e.g., antibody variable regions) that bind to immune effector cells, for example, by virtue of binding to CD3 or CD16.

Methods for determining effector function are known in the art. In one example, the level of ADCC activity is assessed using a $^{51}Cr$ release assay, an europium release assay or a $^{35}S$ release assay. In each of these assays, cells expressing CD83 are cultured with one or more of the recited compounds for a time and under conditions sufficient for the compound to be taken up by the cell. In the case of a $^{35}S$ release assay, the cells can be cultured with $^{35}S$-labeled methionine and/or cysteine for a time sufficient for the labeled amino acids to be incorporated into newly synthesized proteins. Cells are then cultured in the presence or absence of the protein and in the presence of immune effector cells, for example, PBMCs and/or NK cells. The amount of $^{51}$Cr, europium and/or $^{35}$S in cell culture medium is then detected, and an increase in the presence of the protein compared to in the absence of immunoglobulin indicates that the binding molecule/agent has effector function. Exemplary publications disclosing assays for assessing the level of ADCC induced by an immunoglobulin include Hellstrom et al. Proc. Natl Acad. Sci. USA 83: 7059-7063, 1986 and Bruggemann et al., J. Exp. Med. 166: 1351-1361, 1987.

Other assays for assessing the level of ADCC induced by an immunoglobulin include ACTI™ nonradioactive cytotoxicity assay for flow cytometry (CellTechnology, Inc. CA, USA) or CytoTox 96® non-radioactive cytotoxicity assay (Promega, WI, USA).

Alternatively, or additionally, effector function of a CD83 binding protein is assessed by determining its affinity for one or more FcγRs, for example, as described in U.S. Pat. No. 7,317,091.

C1q binding assays may also be carried out to confirm that the CD83 binding protein is able to bind C1q and may induce CDC. To assess complement activation, a CDC assay may be performed (see, e.g., Gazzano-Santoro et al., J. Immunol. Methods 202: 163, 1996).

In another example, the CD83 binding protein comprises one or more amino acid substitutions that increase the half-life of the protein. For example, the CD83 binding protein comprises a constant region comprising one or more amino acid substitutions that increase the affinity of the constant region for the neonatal Fc region (FcRn). For example, the constant region has increased affinity for FcRn at lower pH, for example, about pH 6.0, to facilitate Fc/FcRn binding in an endosome. In one example, the constant region has increased affinity for FcRn at about pH 6 compared to its affinity at about pH 7.4, which facilitates the re-release of Fc into blood following cellular recycling. These amino acid substitutions are useful for extending the half life of a CD83 binding protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Mutant CD83 Binding Proteins

The present disclosure also provides a CD83 binding protein or a nucleic acid encoding same having at least 80% identity to a sequence disclosed herein. In one example, a CD83 binding protein or nucleic acid of the disclosure comprises sequence at least about 80% or 81% or 82% or 83% or 84% or 85% or 90% or 95% or 96% or 97% or 98% or 99% identical to a sequence disclosed herein, wherein the protein specifically binds to CD83.

Alternatively, or additionally, the CD83 binding protein comprises a CDR (e.g., three CDRs) at least about 30% or 35% or 40% or 45% or 50% or 55% or 60% or 65% or 70% or 75% or 80% or 85% or 90% or 95% or 97% or 98% or 99% identical to CDR(s) of a $V_H$ or $V_L$ as described herein according to any example, wherein the protein is capable of specifically binding to CD83. In this regard, the inventors have produced numerous antibodies having diverse sequences within their CDRs. Methods for determining binding of a protein CD83 are described herein.

For example, the inventors have identified a group of CD83 binding proteins sharing at least about 60% identity in their light chain CDR1, such as, for example, with at least about 65% or 70% or 75% or 80% or 85% or 90% or 95% or 96% or 97% or 98% or 99% identity in their light chain CDR1 according to the Kabat numbering system.

The inventors have also identified a group of CD83 binding proteins sharing 70% identity in their light chain CDR2, such as, for example, with at least about 75% or 80% or 85% or 90% or 95% or 96% or 97% or 98% or 99% identity in their light chain CDR2 according to the Kabat numbering system.

The inventors have also identified a group of CD83 binding proteins sharing 30% identity in their light chain CDR3, such as, for example, with at least about 35% or 40% or 45% or 50% or 55% or 60% or 65% or 70% or 75% or 80% or 85% or 90% or 95% or 96% or 97% or 98% or 99% identity in their light chain CDR3 according to the Kabat numbering system.

As discussed herein, the four N-terminal amino acids of a light chain CDR1 can be deleted or any one or more of those amino acids can be substituted with another naturally-occurring amino acid (Padlan et al., FASEB J., 9: 133-139, 1995). Thus, a CD83 binding protein of the disclosure can comprise a CDR1 having at least about 70% identity to a light chain CDR1 sequence disclosed herein.

In another example, a nucleic acid of the disclosure comprises a sequence at least about 80% or 85% or 90% or 95% or 97% or 98% or 99% identical to a sequence disclosed herein and encoding a CD83 binding protein which is capable of specifically binding to CD83. The present disclosure also encompasses nucleic acids encoding a CD83 binding protein of the disclosure, which differs from a sequence exemplified herein as a result of degeneracy of the genetic code.

The % identity of a nucleic acid or polypeptide is determined by GAP (Needleman and Wunsch. Mol. Biol. 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

As discussed above, the present disclosure also contemplates a nucleic acid that hybridizes under stringent hybridization conditions to a nucleic acid encoding a CD83 binding protein described herein, for example, nucleic acid encoding a $V_H$ or $V_L$ of antibody 3C12, 3C12.B, 3C12.C, 3C12.D, or 3C12.E. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency.

Medium stringency is to be considered to be within 10° C. to 20° C. or 10° C. to 15° C. of the calculated Tm of the nucleic acid.

The present disclosure also contemplates mutant forms of a CD83 binding protein of the disclosure comprising one or more conservative amino acid substitutions compared to a sequence set forth herein. In some examples, the CD83 binding protein comprises 10 or fewer, for example, 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), (3-branched side chains (e.g., threonine, valine, isoleucine) and aromatic side chains (e.g., tyrosine, phenylalanine, tryptophan, histidine). Hydropathic indices are described, for example, in Kyte and Doolittle J. Mol. Biol., 157: 105-132, 1982 and hydrophylic indices are described in, for example, U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the CD83 binding protein comprises 10 or fewer, for example, 9 or 8 or 7 or 6 or 5 or 4 or 3 or 2 or 1 non-conservative amino acid substitutions.

In one example, the mutation(s) occur within a FR of an antigen binding domain of a CD83 binding protein of the disclosure. In another example, the mutation(s) occur within a CDR of a CD83 binding protein of the disclosure.

Exemplary methods for producing mutant forms of a CD83 binding protein include:

mutagenesis of DNA (Thie et al., Methods Mol. Biol. 525: 309-322, 2009) or RNA (Kopsidas et al., Immunol. Lett. 107:163-168, 2006; Kopsidas et al. BMC Biotechnology, 7: 18, 2007; and WO1999/058661);

introducing a nucleic acid encoding the polypeptide into a mutator cell, for example, XL-1Red, XL-mutS and XL-mutS-Kanr bacterial cells (Stratagene);

DNA shuffling, for example, as disclosed in Stemmer, Nature 370: 389-91, 1994; and site directed mutagenesis, for example, as described in Dieffenbach (ed) and Dveksler (ed) (In: PCR Primer: A Laboratory Manual, Cold Spring Harbor Laboratories, N Y, 1995).

Exemplary methods for determining biological activity of the mutant CD83 binding proteins of the disclosure will be apparent to the skilled artisan and/or described herein, for example, antigen binding. For example, methods for determining antigen binding, competitive inhibition of binding, affinity, association, dissociation and therapeutic efficacy are described herein.

Exemplary CD83 Binding Proteins

Exemplary variable region containing CD83 binding proteins produced by the inventors and their encoding nucleic acids are described in Tables 1 and 2.

TABLE 1

Sequences of exemplary CD83 binding proteins and encoding nucleic acids

| | Antibody Name | $V_H$ amino acid SEQ ID NO | $V_H$ chain nucleotide SEQ ID NO | $V_L$ amino acid SEQ ID NO | $V_L$ chain nucleotide SEQ ID NO |
|---|---|---|---|---|---|
| 1 | 3C12 | 1 | 35 | 5 | 36 |
| 2 | 3C12.B | 1 | 35 | 6 | 37 |
| 3 | 3C12.C | 1 | 35 | 7 | 38 |
| 4 | 3C12.D | 1 | 35 | 8 | 39 |
| 5 | 3C12E | 1 | 35 | 9 | 40 |

TABLE 2

Amino acid substitutions in $V_L$ (relative to SEQ ID NO: 5) of exemplary CD83 binding proteins

| | Antibody name | $V_L$ substitution |
|---|---|---|
| 1 | 3C12.B | I2V; L10F, L15I; T20S; A25T; K30S; Y32H; F33L; R39K; T51A; N53S; E70D; F83I; L91V; G92N; A93S; L96Y; G100Q; K103R |
| 2 | 3C12.C | M4L; L10S; L15V; K30R; F33L; R39K; A43V; N53T; G66R; Q79H; L91V; G92D; A93R; Y94F; L96Y; G100Q; L104V |
| 3 | 3C12.D | V3Q; L10S; L15V; K30S; N31S; Y32W; F33L; R39K; T51A; N53S; E81D; Q90K; G92S; A93S; L96Y; L104V |
| 4 | 3C12E | M4L; L10S; L15V; K30S; F33L; R39K; A43V; T51A; N53T; E70H; F83V; Q90K; L91C; G92N; A93S; Y94A; L96Y; G100Q; L104V |

Methods for Producing Proteins
Recombinant Expression

As discussed herein, a nucleic acid encoding a CD83 binding protein of the disclosure and/or one or more polypeptides thereof is introduced into an expression construct, such that it is operably linked to a promoter to thereby facilitate its expression. Methods for producing expression constructs, for example, cloning into expression constructs/vectors are known in the art and/or described in Ausubel et al., (In: Current Protocols in Molecular Biology. Wiley Interscience, ISBN 047 150338, 1987), and (Sambrook et al., (In: Molecular Cloning: Molecular Cloning: A Laboratory Manual, Cold Spring Harbor Laboratories, New York, Third Edition 2001) and U.S. Pat. No. 7,270,969.

In one example, the CD83 binding protein of the disclosure is expressed in a bacterial cell. Typical promoters suitable for expression in bacterial cells such as, for example, a bacterial cell selected from the group comprising *E. coli, Staphylococcus* sp., *Corynebacterium* sp., *Salmonella* sp., *Bacillus* sp., and *Pseudomonas* sp., include, but are not limited to a promoter such as lacz, Ipp, a temperature-sensitive L or R promoters, T7, T3, SP6 or semi-artificial promoters such as the IPTG-inducible tac promoter or lacUV5 promoter.

In another example, the CD83 binding protein is expressed in a yeast cell. Typical promoters suitable for expression in yeast cells such as, *Pichia pastoris, Saccharomyces cerevisiae* and *S. pombe*, include, but are not limited to, promoters from the following genes ADH1, GAL1, GAL4, CUP1, PHO5, nmt, RPR1, or TEF1.

In a further example, the CD83 binding protein is expressed in an insect cell. Typical promoters suitable for expression in insect cells, or in insects, include, but are not limited to, the OPEI2 promoter, the insect actin promoter isolated from *Bombyx muri*, the *Drosophila* sp. dsh promoter (Marsh et al., Hum. Mol. Genet. 9: 13-25, 2000).

A CD83 binding protein of the disclosure can also be expressed in plant cells. Promoters for expressing peptides in plant cells are known in the art, and include, but are not limited to, the *Hordeum vulgare* amylase gene promoter, the cauliflower mosaic virus 35S promoter, the nopaline synthase (NOS) gene promoter, and the auxin inducible plant promoters P1 and P2.

In one example, a CD83 binding protein of the disclosure is expressed in a mammalian cell or in a mammal. Typical promoters suitable for expression in a mammalian cell include, for example a promoter selected from the group consisting of, retroviral LTR elements, the SV40 early promoter, the SV40 late promoter, the CMV IE (cytomegalovirus immediate early) promoter, the EF1 promoter (from human elongation factor 1), the EM7 promoter, the UbC promoter (from human ubiquitin C). Examples of useful mammalian host cell lines include monkey kidney CV1 line transformed by SV40 (COS-7); human embryonic kidney line (HEK-293 cells); baby hamster kidney cells (BHK); Chinese hamster ovary cells (CHO); African green monkey kidney cells (VERO-76); or myeloma cells (e.g., NS/0 cells).

Exemplary cells used for expressing a CD83 binding protein of the disclosure are CHO cells, myeloma cells or HEK cells. The cell may further comprise one or more genetic mutations and/or deletions that facilitate expression of a modified antibody. One non-limiting example is a deletion of a gene encoding an enzyme required for fucosylation of an expressed immunoglobulin or antibody. For example, the deleted gene encodes FUT8. A commercially available source of FUT8-deleted CHO cells is Biowa (Potelligent™ cells). For example, the cells used for expression of an defucosylated immunoglobulin or antibody are FUT8-deleted CHO cells, such as, Biowa's Potelligent™ cells.

Other elements of expression constructs/vectors are known in the art and include, for example, enhancers, transcriptional terminators, polyadenylation sequences, nucleic acids encoding selectable or detectable markers and origins of replication.

In one example, an expression construct is a bicistronic expression construct. By "bicistronic" is meant a single nucleic acid molecule that is capable of encoding two distinct polypeptides from different regions of the nucleic acid, for example, a single nucleic acid capable of encoding a $V_H$ containing polypeptide and a $V_L$ containing polypeptide as distinct polypeptides. Generally, the regions encoding each distinct polypeptide are separated by an internal ribosome entry site (IRES) and the region 5' of the IRES does not comprise a transcription termination sequence. Exemplary IRESs are described, for example, in US20090247455.

Following production of a suitable expression construct, it is introduced into a suitable cell using any method known in the art. Exemplary methods include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The cells used to produce the CD83 binding proteins of this disclosure are then cultured under conditions known in the art to produce the CD83 binding protein of the disclosure.

Cell free expression systems are also contemplated by the present disclosure, for example, the TNT T7 and TNT T3 systems (Promega), the pEXP1-DEST and pEXP2-DEST vectors (Invitrogen).

Protein Purification

Following production/expression, a CD83 binding protein of the disclosure is purified using a method known in the art. Such purification provides the protein of the disclosure substantially free of nonspecific protein, acids, lipids, carbohydrates, and the like. In one example, the protein will be in a preparation wherein more than about 90% (e.g., 95%, 98% or 99%) of the protein in the preparation is a CD83 binding protein of the disclosure.

Standard methods of peptide purification are employed to obtain an isolated CD83 binding protein of the disclosure, including but not limited to various high-pressure (or performance) liquid chromatography (HPLC) and non-HPLC polypeptide isolation protocols, such as size exclusion chromatography, ion exchange chromatography, hydrophobic interaction chromatography, mixed mode chromatography, phase separation methods, electrophoretic separations, precipitation methods, salting in/out methods, immunochromatography, and/or other methods.

In one example, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a CD83 binding protein comprising a Fc region of an antibody, protein A or protein G or modified forms thereof can be used for affinity purification. Protein A is useful for isolating purified proteins comprising a human γ1, γ2, or γ4 heavy chain Fc region. Protein G is recommended for all mouse Fc isotypes and for human γ3.

Conjugates

In one example, a CD83 binding protein of the present disclosure is conjugated to a compound. For example, the compound is selected from the group consisting of a radioisotope, a detectable label, a therapeutic compound, a colloid, a toxin, a nucleic acid, a peptide, a protein, a compound that increases the half life of the CD83 binding protein in a subject and mixtures thereof.

The compound can be directly or indirectly bound to the CD83 binding protein (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), a compound that increases the half life of the CD83 binding protein in a subject (e.g., polyethylene glycol or other water soluble polymer having this activity) and mixtures thereof. Exemplary compounds that can be conjugated to a CD83 binding protein of the disclosure and methods for such conjugation are known in the art and described, for example, in US2010221262.

Some exemplary compounds that can be conjugated to a CD83 binding protein of the present disclosure are listed in Table 3.

TABLE 3

Compounds useful in conjugation

| Group | Detail |
|---|---|
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Rc, $^{203}$Pb, $^{64}$Cu, $^{105}$Rh, $^{198}$Au, $^{199}$Ag or $^{177}$Lu |
| Half life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | fluorescent proteins such as *Renilla* luciferase, GFP<br>immune modulators, such as cytokines<br>toxins<br>an immunoglobulin or antibody or antibody variable region<br>half life extenders such as albumin or antibody variable regions or peptides that bind to albumin |
| Chemotherapeutics | Taxol<br>5-FU<br>Doxorubicin<br>Idarubicin |

Screening Assays

CD83 binding proteins of the present disclosure are readily screened for biological activity, for example, as described below.

Binding Assays

One form of assay is an antigen binding assay, for example, as described in Scopes (In: Protein purification: principles and practice, Third Edition, Springer Verlag, 1994). Such a method generally involves labeling the CD83 binding protein and contacting it with immobilized antigen. Following washing to remove non-specific bound protein, the amount of label and, as a consequence, bound protein is detected. Of course, the CD83 binding protein can be immobilized and the antigen labeled. Panning-type assays, for example, as described or exemplified herein can also be used. Alternatively, or additionally, surface plasmon resonance assays can be used.

In one example, a binding assay is performed with peptide comprising an epitope of CD83. In this way, CD83 binding proteins that bind to a specific region of CD83 are selected.

In Vivo Assays

CD83 binding proteins of the present disclosure can also be assessed for therapeutic efficacy in an animal model of a condition, for example, a CD83 mediated condition. For example, the CD83 binding protein is administered to a model of inflammatory bowel disease or colitis (e.g., dextran sodium sulphate (DSS)-induced colitis or CD45Rb adoptive transfer model of colitis (e.g., Kanai et al., Inflamm. Bowel Dis. 12: 89-99, 2006). In another example, a CD83 binding protein is administered to a model of multiple sclerosis, for example, EAE models in which a mouse or rat is immunized with a myelin sheath protein or peptide derived therefrom (e.g., MOG, MBP or PLP) and an immune response is generated against the protein thereby inducing a model of multiple sclerosis. Exemplary EAE models are reviewed in, for example Tsunoda and Fujinami, J. Neuropathol. Exp. Neurol. 55: 673-686, 1996. The CD83 binding protein can also or alternatively be tested in a model of arthritis, for example, a SKG strain of mouse (Sakaguchi et al., Nature 426: 454-460, 1995), rat type II collagen arthritis model, mouse type II collagen arthritis model or antigen induced arthritis models (Bendele J. Musculoskel. Neuron. Interact. 1: 377-385, 2001) and/or a model of inflammatory airway disease (for example, OVA challenge or cockroach antigen challenge).

The therapeutic efficacy of a CD83 binding protein of the present disclosure can also or alternatively be assessed in a model of graft-versus-host-response, for example, in which splenocytes from one animal are injected into a allogeneic animal (e.g., a MHC or HLA unmatched animal). In one example, human peripheral blood mononuclear cells (PBMCs) are transplanted into a xenogeneic SCID mouse model via, for example, intraperitoneal injection after sub lethal total body irradiation inducing a fatal human CD4$^+$ T cell mediated graft versus host response that requires human DCs. Treatment with a CD83 binding protein of the disclosure can be administered to mice, by, for example, intraperitoneal injection on the day of PBMC transplant (day 0) and mice scored for clinical manifestations of GVDH.

Competitive Binding Assays

Assays for determining a CD83 binding protein that competitively inhibits binding of an antibody of the disclosure will be apparent to the skilled artisan. For example, the antibody of the disclosure is conjugated to a detectable label, for example, a fluorescent label or a radioactive label. The labeled antibody and the test CD83 binding protein are then mixed and contacted with CD83 or a peptide comprising an epitope thereof. The level of labeled antibody is then determined and compared to the level determined when the labeled antibody is contacted with the CD83 or the peptide comprising an epitope thereof in the absence of the CD83 binding protein. If the level of labeled antibody is reduced in the presence of the CD83 binding protein compared to the absence of the CD83 binding protein, the CD83 binding protein competitively inhibits binding of the antibody.

Optionally, the CD83 binding protein is conjugated to a different label than the antibody. This permits detection of the level of binding of the CD83 binding protein to CD83 or epitope bearing peptide.

In another example, the CD83 binding protein is permitted to bind to CD83 or a peptide comprising an epitope thereof prior to contacting the CD83 or peptide with an antibody described herein. A reduction in the amount of bound antibody in the presence of the CD83 binding protein compared to in the absence of the CD83 binding protein indicates that the CD83 binding protein competitively inhibits binding of the antibody to CD83. A reciprocal assay can also be performed using labeled CD83 binding protein and first allowing the antibody to bind to CD83 or the peptide. In this case, a reduced amount of labeled CD83 binding protein bound to CD83 or the peptide in the presence of the antibody compared to in the absence of antibody indicates that the CD83 binding protein competitively inhibits binding of the antibody to CD83.

Epitope Mapping Assays

In another example, the epitope bound by a protein described herein is mapped. Epitope mapping methods will be apparent to the skilled artisan. For example, a series of overlapping peptides spanning the CD83 sequence or a region thereof comprising an epitope of interest, for example, peptides comprising 10 to 15 amino acids are produced. The CD83 binding protein is then contacted to each peptide or a combination thereof and the peptide(s) to which it binds determined. This permits determination of peptide(s) comprising the epitope to which the CD83 binding protein binds. If multiple non-contiguous peptides are bound by the protein, the protein may bind a conformational epitope.

Alternatively, or in addition, amino acid residues within CD83 are mutated, for example, by alanine scanning mutagenesis, and mutations that reduce or prevent protein binding are determined. Any mutation that reduces or prevents binding of the CD83 binding protein is likely to be within the epitope bound by the protein.

A further method involves binding CD83 or a region thereof to an immobilized CD83 binding protein of the present disclosure and digesting the resulting complex with proteases. Peptide that remains bound to the immobilized protein are then isolated and analyzed, for example, using mass spectrometry, to determine their sequence.

A further method involves converting hydrogens in CD83 or a region thereof to deuterium atoms and binding the resulting protein to an immobilized CD83 binding protein of the present disclosure. The deuterium atoms are then converted back to hydrogen, the CD83 or region thereof isolated, digested with enzymes and analyzed, for example, using mass spectrometry to identify those regions comprising deuterium, which would have been protected from conversion to hydrogen by the binding of a CD83 binding protein described herein.

Half Life Assays

Some CD83 binding proteins encompassed by the present disclosure have an improved half-life, for example, are modified to extend their half-life compared to CD83 binding proteins that are unmodified. Methods for determining a CD83 binding protein with an improved half-life will be apparent to the skilled person. For example, the ability of a CD83 binding protein to bind to a neonatal Fc receptor (FcRn) is assessed. In this regard, increased binding affinity for FcRn increased the serum half-life of the CD83 binding protein (see for example, Kim et al., Eur. J. Immunol., 24: 2429, 1994).

The half-life of a CD83 binding protein of the disclosure can also be measured by pharmacokinetic studies, for example, according to the method described by Kim et al, Eur. J. of Immunol. 24: 542, 1994. According to this method, radiolabeled CD83 binding protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the CD83 binding protein, the clearance rate in beta-phase is calculated and compared with that of the wild type or unmodified CD83 binding protein.

Stability Assays

Stability of a CD83 binding protein of the disclosure can be assessed by any of a variety of assays. For example, the CD83 binding protein is exposed to a condition, for example, heat or acid or stored for a period of time (e.g., 1 month) at room temperature. Aggregation of the CD83 binding protein can then be assessed by determining turbidity (with an increase in turbidity following exposure to the condition indicating instability), size exclusion chromatography, non-reducing gel electrophoresis or a binding or neutralization study described herein.

Pharmaceutical Compositions and Methods of Treatment

The CD83 binding protein of the present disclosure or nucleic acid encoding same or cell expressing same (syn. active ingredient) is useful for parenteral, topical, oral, or local administration, aerosol administration, or transdermal administration, for prophylactic or for therapeutic treatment.

Formulation of a CD83 binding protein or nucleic acid encoding same or cell expressing same to be administered will vary according to the route of administration and formulation (e.g., solution, emulsion, capsule) selected. An appropriate pharmaceutical composition comprising CD83 binding protein or nucleic acid encoding same or cell expressing same to be administered can be prepared in a physiologically acceptable carrier. A mixture of CD83 binding proteins can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The CD83 binding protein of this disclosure can be lyophilized for storage and reconstituted in a suitable carrier prior to use according to art-known lyophilization and reconstitution techniques.

The optimum concentration of the active ingredient(s) in the chosen medium can be determined empirically, according to procedures well known to the skilled artisan, and will depend on the ultimate pharmaceutical formulation desired.

The dosage ranges for the administration of the CD83 binding protein of the disclosure are those large enough to produce the desired effect. For example, the composition comprises a therapeutically or prophylactically effective amount of the CD83 binding protein or nucleic acid encoding same or cell expressing same.

As used herein, the term "effective amount" shall be taken to mean a sufficient quantity of the CD83 binding protein, nucleic acid, or cells to induce/increase or inhibit/reduce/prevent CD83 activity in a subject. The skilled artisan will be aware that such an amount will vary depending on, for example, the CD83 binding protein, nucleic acid, or cells and/or the particular subject and/or the type or severity of a condition being treated. Accordingly, this term is not to be construed to limit the disclosure to a specific quantity, for example, weight or number of CD83 binding proteins, nucleic acids, or cells.

As used herein, the term "therapeutically effective amount" shall be taken to mean a sufficient quantity of CD83 binding protein, nucleic acid, or cells to reduce or inhibit one or more symptoms of a condition.

As used herein, the term "prophylactically effective amount" shall be taken to mean a sufficient quantity of CD83 binding protein, nucleic acid or cells to prevent or inhibit or delay the onset of one or more detectable symptoms of a condition.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 300 mg/kg, for example, from about 0.2 mg/kg to about 200 mg/kg, such as, from about 0.5 mg/kg to about 20 mg/kg, in one or more dose administrations daily, for one or several days.

In one example, the CD83 binding protein is administered subcutaneously or intravenously.

In some examples, the CD83 binding protein or other active ingredient is administered at an initial (or loading) dose which is higher than subsequent (maintenance doses). For example, the binding molecule is administered at an initial dose of between about 1 mg/kg to about 30 mg/kg. The binding molecule is then administered at a maintenance dose of between about 0.0001 mg/kg to about 1 mg/kg. The maintenance doses may be administered every 7 to 35 days, such as, every 14 or 21 or 28 days.

In some examples, a dose escalation regime is used, in which a CD83 binding protein or other active ingredient is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

One or more CD83 binding proteins of the present disclosure can be administered to an individual by an appropriate route, either alone or in combination with (before, simultaneous with, or after) another drug or agent. For example, the CD83 binding protein of the present disclosure can also be used in combination with proteins, for example, a TNF antagonist, an anti-IL-12/23 antibody, an anti-inflammatory, a corticosteroid, methotrexate or a painkiller. The CD83 binding protein of the present disclosure can be used as separately administered compositions given in conjunction with antibiotics and/or antimicrobial agents.

It will be appreciated by those skilled in the art that the CD83 binding proteins of the present disclosure may be introduced into a subject by administering an expression construct of the disclosure or a cell expressing a CD83 binding protein of the disclosure. A variety of methods can be used for introducing a nucleic acid encoding the antibody into a target cell in vivo. For example, the naked nucleic acid may be injected at the target site, may be encapsulated into liposomes, or may be introduced by way of a viral vector.

CD83 Detection Assays

The following assays can be performed with a CD83 binding protein of the disclosure, for example, a CD83 binding protein conjugated to a detectable label as discussed herein. Detection of CD83 with an assay described herein is useful for diagnosing or prognosing a condition.

An immunoassay is an exemplary assay format for diagnosing a condition in a subject or detecting CD83 in a sample. The present disclosure contemplates any form of immunoassay, including Western blotting, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, and fluorescence activated cell sorting (FACS)-based assays.

One form of a suitable immunoassay is, for example, an ELISA or FLISA.

In one form, such an assay involves immobilizing a CD83 binding protein of the disclosure onto a solid matrix, such as, for example a polystyrene or polycarbonate microwell or dipstick, a membrane, or a glass support (e.g., a glass slide). A test sample is then brought into direct contact with the CD83 binding protein and CD83 in the sample is bound or captured. Following washing to remove any unbound protein in the sample, a protein that binds to CD83 at a distinct epitope is brought into direct contact with the captured CD83. This detector protein is generally labeled with a detectable reporter molecule, such as, for example, an enzyme (e.g. horseradish peroxidase (HRP)), alkaline phosphatase (AP) or β-galactosidase) in the case of an ELISA or a fluorophore in the case of a FLISA. Alternatively, a second labeled protein can be used that binds to the detector protein. Following washing to remove any unbound protein the detectable reporter molecule is detected by the addition of a substrate in the case of an ELISA, such as, for example, hydrogen peroxide, TMB, or toluidine, or 5-bromo-4-chloro-3-indol-beta-D-galactopyranoside (x-gal). Of course, the immobilized (capture) protein and the detector protein may be used in the opposite manner.

The level of the antigen in the sample is then determined using a standard curve that has been produced using known quantities of the marker or by comparison to a control sample.

The assays described above are readily modified to use chemiluminescence or electrochemiluminescence as the basis for detection.

As will be apparent to the skilled artisan, other detection methods based on an immunosorbent assay are useful in the performance of the present disclosure. For example, an immunosorbent method based on the description supra using a radiolabel for detection, or a gold label (e.g., colloidal gold) for detection, or a liposome, for example, encapsulating NAD+ for detection or an acridinium linked immunosorbent assay.

In some examples of the disclosure, the level of CD83 is determined using a surface plasmon resonance detector (e.g., BIAcore™, GE Healthcare, Piscataway, N.J.), a flow through device, for example, as described in U.S. Pat. No. 7,205,159, a micro- or nano-immunoassay device (e.g., as described in U.S. Pat. No. 7,271,007), a lateral flow device (e.g., as described in US20040228761 or US20040265926), a fluorescence polarization immunoassay (FPIA e.g., as described in U.S. Pat. Nos. 4,593,089 or 4,751,190), or an immunoturbidimetric assay (e.g., as described in U.S. Pat. Nos. 5,571,728 or 6,248,597).

Conditions or Disease

The CD83 binding proteins of the disclosure can be used for the treatment, prevention, diagnosis or prophylaxis of a CD83 associated condition or disease.

Exemplary conditions or disease that can be treated, prevented, diagnosed, or prognosed by performing a method of the disclosure include inflammatory or autoimmune conditions or diseases.

Exemplary conditions and diseases include allergies, asthma, graft rejection, autoimmune conditions such as myasthemia gravis, multiple sclerosis, vasculitis, cronic inflammatory bowl diseases such as Morbus Crohn or colitis ulcerosa, HLA B27-associated autoimmunopathis such as Morbus Bechterew, and systemic lupus erythematosis, skin diseases such as psoriasis, rheumatoid arthritis, insulin-dependent diabetes mellitus and AIDS.

In one example, the CD83 binding protein of the disclosure depletes immune cells such as antigen presenting cells (APC) (e.g., dendritic cells (DCs)) and/or lymphocytes (e.g., T cells) to modulate aberrant or unwanted immune responses in, for example, inflammatory and/or autoimmune conditions or diseases. In one example, the CD83 binding protein is an antibody which specifically binds to the surface of an APC and/or lymphocyte and depletes the APC and/or lymphocyte via antibody dependent mediated cytotoxicity (ADCC). In one example, ADCC is mediated by natural killer (NK) cells.

Graft Rejection

In one example, the CD83 binding proteins of the disclosure can be used to deplete immune cells such as APCs and/or lymphocytes to modulate immune responses associated with, for example, rejection of a graft by, for example, graft versus host disease or host versus graft disease. In one example, the graft is an organ or tissue or cell graft. In one example, the graft is an allograft. In one example, the graft is an hematopoietic stem cell graft.

Graft versus host disease may result where an immunocompetent graft, for example, an allogeneic hematopoietic stem cell graft, is administered with viable and functional immune cells to a recipient, for example, an histo-incompatible recipient, and the immune cells present in the graft, for example, T cells, attack tissues of the transplant recipient.

Host versus graft disease may result where antigens derived from the allogenic graft are presented by either donor or recipient APCs to immune cells of the recipient, for example, T cells, which are in turn activated to become effector immune cells, for example, cytotoxic T lymphoctes (CTLs) that then attack the transplant.

An "allogeneic graft" is a graft from a genetically non-identical donor (e.g., histo-incompatible donor) of the same species.

Hematopoietic Stem Cell Transplantation (HSCT)

An "hematopoietic stem cell transplantation (HSCT)" is a graft comprising multipotent hematopoietic stem cells which can be derived, for example, from bone marrow or peripheral blood. The transplant may include some non-stem cells, for example, APCs including DCs and/or lymphocytes.

"Hematopoietic stem cells" can self renew and differentiate to give rise to all the blood cell types including myeloid (monocytes and macrophages, neutrophils, basophils, eosinophils, dendritic cells), erythroid (erythrocytes), megakaryocytic (platelets) and lymphoid lineages (T-cells, B-cells, NK-cells). Throughout differentiation, the hematopoietic stem cell first loses its self-renewal capacity, then loses lineage potential step by step as it commits to becoming a mature effector cell. Typically a Lin−, CD34+, CD38−, CD90+, CD45RA− human cell is a hematopoietic stem cell. In one example, expression of CD34 is used to identify hematopoietic stem cells in peripheral blood isolated from human donors.

HSCT can be used in the treatment of diseases and conditions which require stem cell transplants. For example, the stem cells can be used for the treatment of failure or dysfunction of normal blood cell production and maturation, hematopoietic malignancy, autoimmune disease, liver disease, or immunodeficiency (by reason of for example, irradiation, chemotherapy or infection with a pathogen).

The stem cells may be expanded or differentiated ex vivo prior to administration to a subject.

Allogeneic hematopoietic stem-cell transplantation may be used to treat one or more of the following conditions: acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin lymphoma, Hodgkin disease, aplastic anemia, pure red cell aplasia, paroxysmal nocturnal hemoglobinuria, Fanconi anemia, Thalassemia maj or, sickle cell anemia, Severe combined immunodeficiency (SCID), Wiskott-Aldrich syndrome, hemophagocytic lymphohistiocytosis (HLH), inborn errors of metabolism (e.g., mucopolysaccharidosis, Gaucher disease, metachromatic leukodystrophies and adrenoleukodystrophies).

Kits

The present disclosure additionally comprises a kit comprising one or more of the following:

(i) a CD83 binding protein of the disclosure or expression construct(s) encoding same;

(ii) a cell of the disclosure; or (iii) a pharmaceutical composition of the disclosure.

In the case of a kit for detecting CD83, the kit can additionally comprise a detection means, for example, linked to a CD83 binding protein of the disclosure.

In the case of a kit for therapeutic/prophylactic use, the kit can additionally comprise a pharmaceutically acceptable carrier.

Optionally a kit of the disclosure is packaged with instructions for use in a method described herein according to any example.

The present disclosure includes the following non-limiting Examples.

EXAMPLES

Example 1 Materials and Methods

Expression Vector Design mAbXpress vectors were assembled using publicly available human constant region heavy chain (IgG1 and IgG4 subtypes) and κ light chain sequences. Required DNA was synthesized and codon-optimized for mammalian expression by Geneart AG (Germany). These cassettes were then placed into mammalian expression vectors containing sequences for expression, selection and amplification in mammalian cells (Acyte Biotech, Australia). A single SacI site was included in the expression vector to facilitate linearization and In Fusion™ (ClonTech) cloning of the variable region.

Phage Display Panning Against CD83 and Ligation-Independent, in Fusion™ Cloning of scFvs The extracellular domain of human CD83 was expressed in CHO cells and purified by IMAC. This preparation was used to isolate binders from a published human scFv phage display library (Sheets et al., Proc. Natl. Acad. Sci. U.S.A. 95(11): 6157-62, 1998). Several unique binders to recombinant CD83 were isolated and clone 3C12 was selected for cloning and expression. Variable regions for both the heavy and light chains were PCR amplified from the phagemid vectors using primers against the 5' and 3' framework regions of each chain. An additional 15 bp was included on each primer corresponding to upstream and downstream bases of the destination vector to enable ligation-independent In Fusion™ cloning (Clontech). Example primers for the heavy chain were:

```
3C12_VhFor
                                   (SEQ ID NO: 50)
5'-CAGGTGTCCACTCCGAGGTGCAGCTGCAGGAG-3'
and 3C12_VhRev
                                   (SEQ ID NO: 51)
5'-GCGGAGGACACGGTGAGCGTGGTCCCTTGGCCC-3',
``` and for the light chain the primers were:

```
3C12_VkFor
                                  (SEQ ID NO: 52)
5'-CCGGCGTGCACTCCGAGATCGTGATGACCCAG-3'
and 3C12_VkRev
                                  (SEQ ID NO: 53)
5'-GCCACGGTCCGCTTGAGTTCCAGCTTGGTCCC-3'.
```

Underlined regions represent the scFv-specific sequence, which varies from clone to clone. The unpurified PCR products were inserted into the mAbXpress IgG1 heavy and κ light chain vectors using the In Fusion™ system (Clontech), as per the manufacturer's instructions. Transfection and purification of antibodies was performed as described below.

Mammalian Cell Expression

For antibody expression, mAbXpress plasmids harbouring heavy chain and light chain sequences were co-transfected using Polyethylenimine (PEI)-Max prepared in water (Polysciences Inc). Transfection complexes were prepared at a ratio of PEI:DNA of 3.5:1. Transient transfections of suspension-adapted CHO were performed using a 0.75:0.25 v/v ratio of cells:transfection complex, meaning each 750 μL cells (at $1.5 \times 10^6$ cells·mL-1) in CD-CHO media is transfected with 1.6 μg DNA and 5.6 μg PEI in 250 μL of OptiPro SFM medium (Invitrogen). The complex was incubated for 15 mins at room temperature without disruption before addition to the cell suspension. At 4 hours post-transfection, cells were diluted by doubling the total volume with CD-CHO and Insulin-like Growth Factor 1 (IGF-1) at 0.1 mg·L$^{-1}$ before transferring cultures to humidified incubators at 32° C. and 7.5% $CO_2$ for 7-14 days with shaking (160-250 rpm, depending of the vessel and the shaker throw ratio). Expression studies were typically performed at small (2 mL), medium (30 mL) or large (400 mL) scale. Cellular debris was removed by centrifugation and secreted antibody purified with Protein-A chromatography.

Protein A Purification of Immunoglobulins and Ig-Fusion Proteins

A 1 mL Protein A HiTrap column (GE Healthcare) was pump washed with 20 Column Volumes (CV) of PBS. Supernatant containing human IgG1 or CD83-Fc fusion protein, ranging from volumes of 20 mL-1.2 L, were applied at a flow rate of 1 mL per minute. The column was washed with 20-50 CV PBS prior to applying 10 CV of Protein A Elution Buffer with each 1 mL fraction eluted into 40 μL Neutralization Buffer to restore the pH to 7.0.

Analytical Size Exclusion Chromatography (SEC) of Antibodies Expressed in mAbXpress For SEC, a TSK-GEL G3000SWxl 30 cm×7.8 mm column (Tosoh Bioscience) was used on an Agilent 1200 series LC with a mobile phase of 100 mM Phosphate pH 6.7, 200 mM NaCl, filtered through a 0.22 μm filter. Flow rate was 0.8 mL·min$^{-1}$. Calibration was performed using gel filtration standards (Bio-Rad). Typical yields from transient transfection experiments using this system ranged from 20-60 mg·L$^{-1}$.

CD83 Western Blot

To assess whether anti-CD83 mAbs recognise linear or conformational epitopes, recombinant hCD83$_{ECD}$-His protein was prepared for SDS-PAGE. Non-denatured samples (i.e., not denatured by boiling in mercaptoethanol) containing 5 μg hCD83$_{ECD}$-His were loaded directly to wells, whereas denatured samples included 2.5% 3-mercaptoethanol and were heated at 95° C. for 10 mins prior to loading. Proteins were separated on 12% NuPAGE gels (Invitrogen) by running at 200 volts for 50 mins prior to transfer to nitrocellulose membrane for 45 mins at 100 volts using the Transblot System (BioRad). Odyssey Blocking buffer (Li-Cor Biosciences) was applied for 1 hour prior to addition of primary antibody. Primary antibody was composed of either 5 μg·mL$^{-1}$ 3C12 IgG or a 1:2,000 dilution of anti-human CD83 reagent, HB15e-PE, each prepared in PBS with 0.5% Tween-20 (PBST) for 1 hour. After washing twice with PBST, an infrared IRD800 anti-human or mouse Fc antibody (Li-Cor) was applied at 1:10,000 dilution for 45 mins prior to washing and visualisation on Odyssey Infrared Imaging System (Li-Cor).

Quantification of Cell Membrane CD83

The number of cell surface CD83 molecules present on cell lines and blood DCs from human PBMC was estimated using standard QIFIKIT (Dako) protocol (Serke S et al., Cytometry 33(2): 179-87, 1998). In the case of cell lines and transfected cells, $0.5 \times 10^6$ cells were stained with 20 μg·mL$^{-1}$ of unconjugated anti-CD83 mAb, HB15a (Immunotech) for 45 mins at 4° C. and 1:50 dilution of either the kit provided anti-mouse IgG-FITC or anti-mouse IgG-PE (Chemicon). For the quantification of CD83 levels on activated DCs, $1 \times 10^6$ PBMC were cultured overnight to upregulate CD83 (Zhou et al., J. Immunol. 154(8): 3821-35, 1995). Cells were then stained with 20 μg·mL$^{-1}$ HB15a followed by detection as stated above. To block any remaining unbound anti-mouse FITC, 50 μL of 10% mouse serum was added and incubated at 4° C. for 20 mins. A lineage mix consisting of CD3, CD14, CD19, CD20 and CD56 antibodies conjugated to PE and applied at manufacturer's recommendation were added, along with HLA-DR-apc-Cy7 and 150 μg·mL$^{-1}$ biotinylated CMRF-44, subsequently detected with 1:50 dilution of Streptavidin-Pacific Blue. Cells were washed between each step with 2 mL MACS Buffer and centrifuged at 1000×g for 2 mins, as described below. Activated human DCs were gated as lineage-HLA-DR$^+$ CMRF-44$^+$HB15a$^+$. A standard curve was prepared to estimate CD83 surface densities as outlined in the QIFIKIT provided protocol.

Flow Cytometry

Cells for flow cytometric analysis were washed in cold Magnetic-Activated Cell Sorting (MACS) Buffer comprised of 0.5% bovine serum albumin (BSA; Invitrogen) with 2 mM EDTA in PBS pH7.2, or Fluorescence-Activated Cell Sorting (FACS) Buffer containing 0.5% FCS, 0.05% Sodium azide (Ajax Finechem) in PBS. Washed cells were counted and $2 \times 10^5$-$2 \times 10^6$ cells were distributed to 5 mL Polystyrene Round-bottom Tubes (BD Biosciences). All steps involving centrifugation of cell pellets were performed in a DiaCent-12 Benchtop centrifuge (DiaMed) at 1000×g for 2 mins. Cells were stained for 30-60 mins on ice unless otherwise stated in a 50 μL final volume with fluorescent primary or secondary antibody conjugates. Cells were washed with 3 mL FACS or MACS Buffer and pelleted. This step was repeated for multiple step-staining procedures. Cells were either analysed within 3 hours of stain completion or else were fixed by application of 200 μL 1% paraformaldehyde (PFA) for 30 mins, before washing and resuspending in 200 μL FACS Buffer. In cases where dead cells were assessed by 7-AAD staining, cells were left on ice a maximum of 2 hours prior to analysis. Cells were analysed using either FACS Calibur 4-colour flow cytometer using CellQuest software to acquire data, or an LSRII Flow Cytometer System using FACSDiva Version 6.1 software (all BD Biosciences). Data analysis was performed on FlowJo Version 8.8.6 or FCS Express 3 Software (DeNovo Software).

Chemical Conjugation of mAb to R-Phycoerythrin (RPE)

Purified 3C12 or human IgG1 isotype control mAb, Herceptin (60 g) in PBS were covalently coupled to 100 µg RPE with Lynx Rapid RPE Antibody Conjugation (AbD-Serotec) as per manufacturer's specifications. Prior to use in flow cytometry experiments, the antibody was titrated from 0.5-50 µg·mL$^{-1}$, with 5 µg·mL$^{-1}$ determined as an optimal working concentration for staining CD83 on KM-H2 cells.

Preparation of Defucosylated IgG

Non-fucosylated antibody was obtained by adding 2 µg·mL$^{-1}$ kifunensine (GlycoFineChem, New Zealand) to CHO cells transfected as per the standard protocol outlined above, approximately 4-6 hours after addition of the transformation complex. Cultures were harvested after 6-7 days of standard culture and purified using Protein-A affinity chromatography as described above. To validate the content of antibody-associated oligosaccharide, purified protein was concentrated to 2 mg·mL$^{-1}$ using Ultra-4 Centrifugal Filter Device (Amicon) in a fixed angle centrifuge as per manufacturer's instruction. A sample of 50 µL was reduced with 0.25% 2-mercaptoethanol in 50 mM ammonium bicarbonate, 0.25% SDS at 100° C. for 20 mins. Triton-X-100 was added to 0.5% to complex with SDS and subsequently 1 U of N-glycosidase F (Roche) was added. Samples were digested for 4 mins in an inverter microwave prior to dilution and acidification with 0.5% trifluoroacetic acid (TFA), and purified by graphitised carbon solid phase extraction (SPE) chromatography. Purified samples were freeze dried, resuspended in 50 mM NaCl and analysed in super-2,5-dihydroxybenzoic acid (sDHB; Sigma) MALDI-MS matrix on positive reflectron model in the Bruker Ultraflex. Validation of defucosylated IgG by mass spectrometry was subsequently performed.

Construction of V$_L$ Shuffled Library for Affinity Maturation

Heavy chain (V$_H$) DNA of 3C12 scFv was amplified from pHEN1 phagemid vector (Hoogenboom et al., Nucleic Acids Res. 19(15): 4133-7, 1991) with 2.5 U of high fidelity Pfu polymerase (Stratagene) using the kit provided protocol, and the primers with restriction sites (underlined) and the additional 5' sequences overlapping with the vector to allow Gap Repair cloning (Orr-Weaver and Szostack, 1983; Gietz and Schiestl 1991):

```
3C12VH5'
                                       (SEQ ID NO: 54)
5'-GACTATGCAGCTAGCGGTGCCATGGCAGAGGTGCAGCTGCAGGAGT

CGGG-3'

Mod3C12VH3'
                                       (SEQ ID NO: 55)
5'-GTTGAGCCTCCGGACTTAAGGTCGACTGAGGACACGGTGAGCGTGG

TCC-3'
``` at a final concentration of 0.5 µM. The 3C12-V$_L$ shuffled library was constructed using in vivo homologous recombination, based on a previously described method (Zhou et al., J. Mol. Biol. 404(1): 88-99, 2010) with modification as follows. Briefly, 10 µg of gel purified (GeneClean Turbo, Qbiogene) 3C12 V$_H$ fragment DNA was used in standard lithium acetate transformation of EBY100 yeast cells (Antibody Epitope Mapping using Yeast Display (Garcia-Rodriguez C, Zhou Y, Marks J D, eds, 2010), Springer) together with 50 µg of NcoI-SalI digested pYD4 vector containing a library of approximately 10$^7$ human V$_L$ gene sequences. The transformed yeast library was cultured in 500 mL yeast minimal media, Selective growth Dextrose Casamino Acid media (SD-CAA), as defined elsewhere (Antibody Epitope Mapping using Yeast Display (Garcia-Rodriguez C, Zhou Y, Marks J D, eds, 2010), Springer). Culture conditions were at 30° C. with 250 rpm shaking unless otherwise stated. The size of the library was estimated by plating serial dilutions of transformed yeast on SD-CAA plates. At 48 hours post-transformation, a sample representing a ten-fold excess of maximum library diversity (i.e., 10$^8$) was induced in Selective growth Galactose Casamino Acid media (SG-CAA) at 18° C. for 48 hours.

Sorting of V$_L$ Shuffled Library by Yeast Display Using FACS

The displayed 3C12 V$_L$ shuffled library was subjected to three rounds of cell sorting. Each round involved incubation with soluble hCD83ECD-His for 1 hour at 4° C.

The concentration of antigen used to bind to displayed antibody clones in the various rounds of selection was 20 nM, 2.5 nM and 0.5 nM of hCD83$_{ECD}$-His diluted in FACS buffer, for the first through to the third rounds, respectively. The third and final round of sorting also incorporated an overnight wash step in FACS buffer after staining with hCD83ECD-His antigen in order to select clones with slower off rates. Antigen binding was detected in each selection step using an anti-CD83 antibody (either 100 µg·mL$^-$ mouse monoclonal antibody, mB4 or 1 µg·mL$^{-1}$ polyclonal antibody, RA83) captured by 1:500 dilution of respectively, anti-mouse IgG1 Fc specific-FITC or anti-rabbit Fc specific-FITC (both Jackson Immunoresearch). The expression of scFv on the surface of the yeast was assessed during each round using an anti-SV5-Alexa 647. Cells diluted to 1-5×10$^7$ cells·mL$^-$ in cold FACS buffer were analysed on a FACSAriaII instrument (BD Biosciences) and sorted into P2 and P3 collection gates, shown in FIG. 6A. The outputs from the collection gates were cultured at 1×10$^4$-1×10$^5$ cells·mL-1 in SD-CAA liquid media (Antibody Epitope Mapping using Yeast Display (Garcia-Rodriguez C, Zhou Y, Marks J D, eds, 2010), Springer) for 48 hours prior to inducing surface display with galactose-containing SG-CAA liquid media (Antibody Epitope Mapping using Yeast Display (Garcia-Rodriguez C, Zhou Y, Marks J D, eds, 2010), Springer) for the next round of sorting. The output of third round sorted cells was plated on SD-CAA. A total of 90 individual clones were cultured in SD-CAA overnight prior to induction in SG-CAA media for a further 18 hours. Amplified yeast displaying scFv were stained with 0.2 nM hCD83$_{ECD}$-His and compared to yeast-displayed wildtype 3C12 scFv. From this FACS analysis, 20 individual clones with apparent increases in antigen binding intensity were selected for sequencing. DNA sequencing revealed four dominant V$_L$ chain sequences (3C12.B, 3C12.C. 3C12.D and 3C12.E), which were reformatted as human IgG1K (mAbXpress vectors, ACYTE Biotech) as described above.

Generation of Stable Transfectants with Varving Levels of CD83 Expression

Full length cDNA (Genbank accession NM_004233.3) was cloned into a bicistronic Internal Ribosome Entry Site (IRES)-Green Fluorescent Protein (GFP) expression vector, pMXIE.2. Plasmid DNA (10 µg) was used to transfect confluent GP+E86 retroviral packaging cells in a T25 flask using lipofectamine (Invitrogen) as per manufacturer's protocol. When stably transfected GP+E86 packaging cells had reached 80% confluence, the packaging cells were irradiated with 2000 cGy to inhibit expansion, and 5×10$^5$ cells·mL$^{-1}$ of BB88 suspension cell line were added for co-culture, along with 2-4 µg·mL$^{-1}$ hexadimethrine bromide (Sigma) as an enhancer of viral infection. After 48 hours culture at 37° C., 5% CO$_2$, BB88 suspension cells were removed and were sorted for GFP expression using a FACSAriaII instrument. Subsequent sorting rounds were conducted, selecting for transformants with enhanced GFP/CD83 expression. CD83 expression was confirmed by flow cytometric staining of sorted cells. Monoclonal cultures of cells were cloned by limiting dilution.

Depletion of Activated Dendritic Cells with CD83 mAb

Cryopreserved PBMC were thawed and cultured overnight in RPMI-10 to induce up-regulation of CD83 (Zhou and Tedder, J. Immunol. 154(8): 3821-35, 1995). Cells at 2×10$^6$ cells·mL$^{-1}$ were cultured in a final volume of 1 mL in sterile capped 5 mL FACS tubes (BD Biosciences) in the presence of 6,000 IU·mL$^{-1}$ recombinant IL-2 (Boehringer Mannheim) to activate NK cells and either 5 µg·mL$^{-1}$ 3C12.C IgG or human IgG1K isotype control. Cells were incubated for 3-4 days prior to flow cytometric staining and analysis to assess the activated DC population.

Xenogeneic SCID Mouse, Model of GVHD

All animal work was approved by the University of Queensland Animal Ethics Committee. Five-week old SCID mice were obtained from the Animal Resources Centre (Western Australia) and were housed in pathogen-free conditions for a week prior to experimental work. The xenogeneic model used has been previously described (Wilson et al., J. Exp. Med. 206(2): 387-98, 2009). Briefly, mice conditioned on Day −1 with 325 cGy radiation were dosed with antibody against asialoGM1 (ASGM-1), which depletes NK cells and other leukocytes to facilitate engraftment of an intraperitoneal injection of 50×10$^6$ human PBMC on Day 0. Antibody treatments were administered to mice, also via intraperitoneal injection, on the day of PBMC transplant (Day 0) at the dose specified in figure legends. Mice were given scores daily on a metric range from 0.0 (healthy) to 2.0 (poor condition) with 0.5 minimal increments for each clinical manifestation of GVHD for 30 days post-transplant without knowledge of the treatment group to eliminate bias. Scoring criteria were weight loss, posture, activity, fur texture, skin and eye integrity and diarrhoea. Animals scoring 2.0 for any one criteria or possessing a cumulative score >5.0 were sacrificed by cervical dislocation. Animals surviving past Day 20 had spleen, bone marrow and peritoneal cavity washouts collected and assessed for flow cytometric staining with anti-human and anti-mouse CD45 antibodies to confirm the presence of engrafted human cells. Survival curve comparisons were performed in GraphPad Prism Version 5.01 using the Log-rank (Mantel-Cox) test.

Fab Preparation and Affinity Analysis

Fab fragments were generated by papain digestion with Pierce Fab MicroFab Preparation Kit, as per the manufacturer's instructions except that the kit-provided Protein A resin was replaced with MAbSelect SuRE resin (Seldon et al., J. Biomol. Tech. 22: 50-2, 2011). Fab were diluted in HBS-EP buffer consisting of 10 mM Hepes, 150 mM Sodium Chloride, 3 mM EDTA, and 0.005% Polysorbate 20 (GE Healthcare). Diluted Fab were assessed for affinity using a BiaCore3000 (GE Healthcare) instrument equipped with a CM5 chip coupled with 100 Resonance Units (RU) of hCD83ECD-His protein, using the Kinetic Analysis wizard protocol. Kinetic rates were estimated using BiaEvaluation Software (GE Healthcare) using the inbuilt 1:1 binding model with mass transfer limitations.

Cells

Lymphoma cell lines, KM-H2 and L428, and cell lines amenable to transfection including suspension Chinese Hamster Ovary (CHO-S) and mouse cell lines BB88 and FDCP1 were obtained from the Mater Medical Research Institute stocks. Human peripheral blood mononuclear cells (PBMC) were obtained from healthy volunteers donating blood or aphaeresis product, as recruited in accordance with the Mater Health Services Human Research Ethics Committee. All human healthy donor samples were screened for Human Immunodeficiency Virus, Hepatitis B and C, Human T-lymphotropic Virus and Syphilis.

Cell Culture Media and Solutions

Human cell lines and human PBMC were cultured in Roswell Part Memorial Institute (RPMI) medium supplemented with 1× Penicillin-Streptomycin, 2 mM GlutaMAX, 25 mM HEPES and 10% Foetal Calf Serum (FCS) that had been heat-inactivated at 56° C. for 30 minutes prior to use (RPMI-10, all components from Invitrogen). Mouse cell lines BB88 and FDCP1 cells were cultured in Dulbecco's Modified Eagle Medium (Invitrogen) supplemented with Penicillin-Streptomycin, GlutaMAX, HEPES and 10% FCS (DMEM-10). FDCP1 cells transfected with full length human CD83 were additionally cultured in the presence of 100 µg·mL$^{-1}$ G418 Geneticin selective antibiotic. All cells were cultured in a humidified 37° C., 5% CO$_2$ incubator and passaged as appropriate.

Ficoll Preparation of PBMC from Peripheral Blood and Apheresis Products

Density gradient centrifugation was utilized in the purification of PBMC from blood products. Briefly, a 400 mL sample of peripheral blood was diluted 1:1 with sterile room temperature PBS, whilst concentrated aphaeresis products were diluted 1:20 with PBS. In sterile 50 mL tubes, 35 mL of diluted blood product was under-layed with 15 mL of Ficoll-Paque PLUS (GE Healthcare) prior to centrifugation at 600×g for 20 mins with the centrifuge brake switched off. Using a Pasteur pipette, cells at the Ficoll interface were collected and washed 3-5 times with PBS to remove contaminating platelets. Cells were counted using a haemocytometer and either cultured, cryopreserved or used in functional assays.

Cryopreservation and Reviving of Mammalian Cells

PBMC were prepared for cryopreservation by centrifugation at 300×g for 5 mins and resuspending at a final density of 50×10$^6$ cells·mL$^{-1}$ in a solution comprised of 10% dimethyl sulfoxide (DMSO; Sigma) and 90% FCS. All other cells were typically resuspended in a solution containing 8% DMSO, 50% conditioned media and 42% fresh media. Cells were aliquoted into 1 mL sterile cryovials, placed in Cryo 1° C. Freezing Containers (Nalgene) and immediately transferred into temporary storage at −80° C. with relocation into liquid nitrogen storage (−196° C.) occurring within 24-48 hours. As required, cells were thawed in 37° C. water bath and immediately diluted in 15 mL pre-warmed media. Cells were centrifuged at 300×g for 5 mins and resuspended in 10 mL media for further use or culture.

Generation of Lymphokine Activated Killer (LAK) Cells

Fresh or thawed PBMC (<2×10$^9$ cells) were washed and resuspended in cold MACS Buffer comprised of 0.5% bovine serum albumin (BSA; Invitrogen) with 2 mM EDTA in PBS pH7.2. Human CD56 MicroBeads were added as per manufacturer's recommendations and cells were positively selected on a VarioMACS Separator equipped with an LS column (all Miltenyi). To confirm the purity of the NK cells, both positive and negative fractions were stained with a CD56 fluorescent antibody conjugate (BD Biosciences) and analysed by flow cytometry. LAK cells were cultured in the presence of 6000 IU·mL$^{-1}$ human IL-2 (Boehringer Mannheim) at 37° C., 5% $CO_2$ for 2-7 days. Cells were harvested by incubation for 30 mins on ice before supernatant removal, followed by 30 mins on ice in cold PBS containing 2% EDTA; all harvested cells were washed twice before addition before resuspending in RPMI-10.

Chromium Release Assay

To determine the ability of mAbs to elicit ADCC with LAK effector cells, chromium release assays were performed using KM-H2 cell line or BB88 cell lines stably transfected with human CD83 as the chromium-labelled targets. A maximum of 1×10$^6$ cells mL$^{-1}$ were labelled with 100 µCi 51Cr in TD Buffer for 45 mins at 37° C., 5% $CO_2$ with gentle agitation every 10 mins. Cells were washed twice with RPMI-10. LAK effector cells and 1-5× 10$^{-3}$ $^{51}$Cr-labelled target cells were plated in V-bottom 96 well plates (Nunc) at the Effector:Target (E:T) ratio specified in Figure legends. Antibody treatments were added as specified. For blocking experiments, 15 µg·mL$^{-1}$ unconjugated anti-human CD16 clone 3G8 or mouse IgG1k isotype control were added to a final volume of 150 µL. Additional wells containing target cells in either RPMI-10 (i.e. spontaneous release) or 1.67% Triton-X-100 (total release) were prepared. Each condition was run with five replicates. Plated cells were incubated for 4 hours prior to centrifugation at 300×g for 5 mins at room temperature. Supernatant (50 µL) from each well was mixed with 150 µL OptiPhase "Super-Mix" and assayed for $^{51}$Cr counts per minute (cpm) with a Trilux 1450-MicroBeta scintillation counter (both from Wallac). Specific cell lysis was calculated using the standard formula: % lysis=[(test sample cpm−spontaneous cpm)/(total cpm−spontaneous cpm)*100]. GraphPad Prism Version 5.01 software was used to graph data and standard error of the mean.

Mixed Lymphocyte Reaction (MLR)

Cyropreserved PBMC from two human donors were thawed and 20 µg·mL$^{-1}$ DNAaseI (Roche) was added to prevent cellular aggregation. For a one-way MLR, cells from one donor selected to serve as the MLR "stimulator" were irradiated with 3000 cGy. Stimulator cells (1×10$^5$ cells) were added to an equivalent number of the non-irradiated "responder" cells in 96-well U-bottom plates (Nunc), along with the antibody to be tested in a final volume of 180 µL with five replicates per condition. For a two-way MLR, cells from both donors are non-irradiated and participate in allogeneic activation. Following four days incubation at 37° C., 5% $CO_2$, 1 µCi of tritiated thymidine (Perkin Elmer) in a volume of 20 µL was added. The cells were incubated a further 16 hours and then transferred to a filtermat using FilterMate Harvester (PerkinElmer). Filtermats were dried completely before applying 5 mL Betaplate Scint (Wallac) and reading with Trilux 1450 Microbeta counter. Raw data was standardized against the nil antibody control wells and reported as the percentage of maximal proliferation.

Example 2 Generation and Characterization of 3C12 mAb

Figure 1:
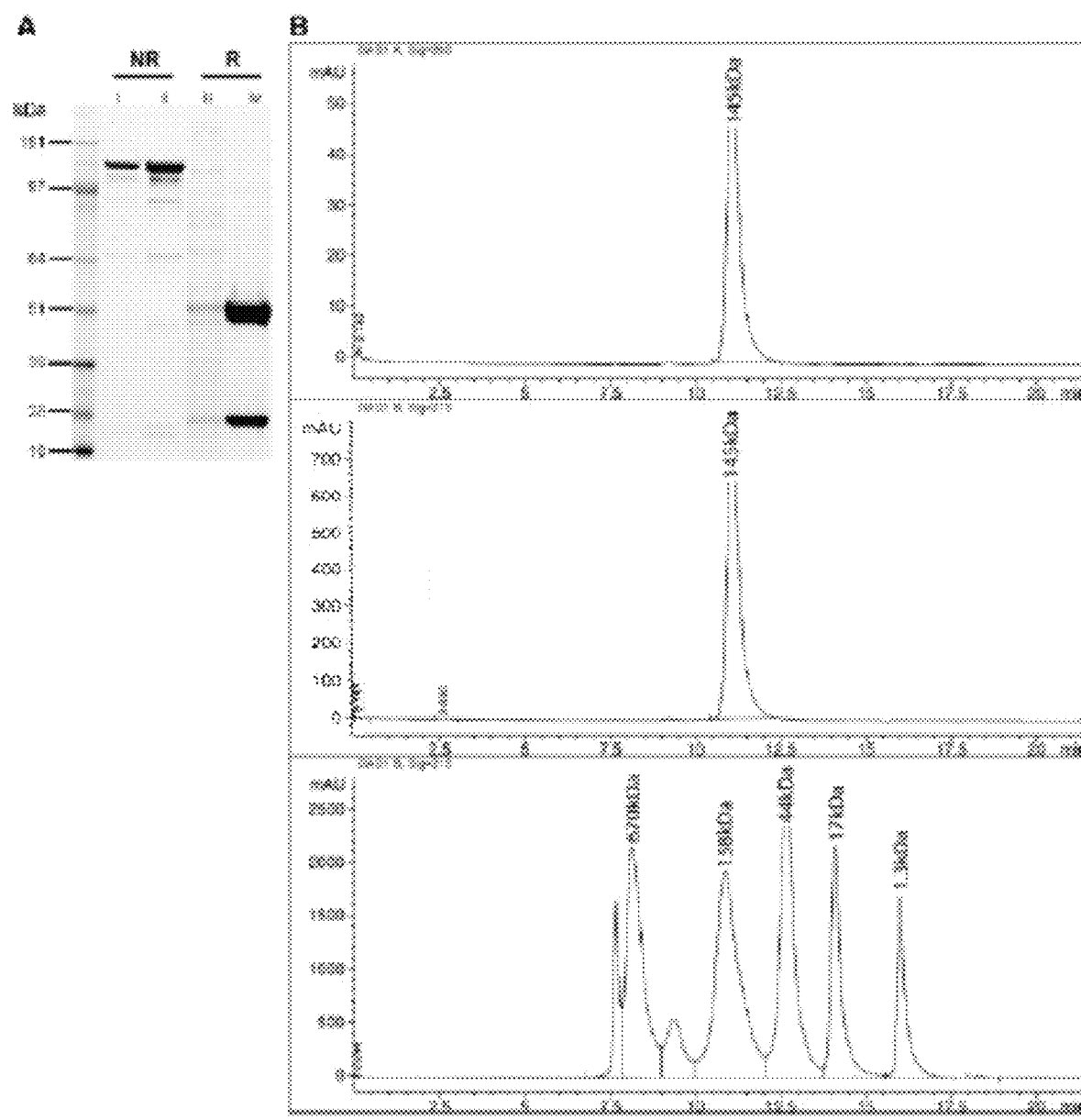
FIG. 1: Analysis of the expression and purification of 3C12 IgG1

An scFv phage clone was obtained by biopanning a large human naïve scFv immunoglobulin gene library (Sheets et al., Proc. Natl. Acad. Sci. U.S.A. 95(11): 6157-62, 1998) by three rounds of selection against recombinant hCD83$_{ECD}$-His. Using primers that bind the semi-conserved flanking framework region for each variable region, and which also contain the required vector overlap, this clone was amplified by PCR and cloned into the mAbXpress vectors using the In Fusion™ system. The reformatted IgG1 mAb was expressed in CHO cells, followed by protein-A based purification. Analysis by SDS-PAGE and SEC (FIG. 1) showed that the molecule was expressed well in this transient expression system, with no observable degradation or aggregation. The reformatted antibody demonstrated specific binding to cell surface CD83 expressed by the human Hodgkin's Lymphoma derived cell line, KM-H2 (FIG. 2).

The anti-CD83 scFv was reformatted as an IgG1 κ specifically to provide an ADCC response. In order to show the resulting antibody was functional, purified recombinant anti-CD83 antibody (i.e., 3C12 mAb) was used in flow cytometry to demonstrate binding to CD83$^+$ human cell lines and hCD83-transfected cells (FIG. 2A). Additionally, in a chromium release functional assay, 3C12 mAb induced significant cytolysis of KM-H2 cells in the presence of activated natural killer (NK) effector cells (FIG. 2B). This antibody-induced lysis, however, was abrogated upon blockade of FcγIIIRa (CD16) with anti-CD16 mAb, 3G8, demonstrating the necessity for CD16 in the in vitro mechanism of action of 3C12 in the chromium release assay.

Example 3 Characterization of Anti-CD83 mAb, 3C12

Anti-human CD83 mAb, 3C12, was characterized to assess binding affinity and specificity (Table 4). 3C12 bound to CD83$^+$ cell line, KM-H2 and suppressed allogeneic T cell stimulation in an MLR.

TABLE 4

| Binding affinity and specificity for 3C12 | |
|---|---|
| Parent scFv library origin | Naïve human |
| hCD83 Peptide$_{A461-78}$ reactivity | — |
| BiaCore Fab Affinity | |
| $K_{on}$ (M$^{-1}$s$^{-1}$) | 9.5 × 10$^5$ |
| $K_{off}$ (s$^{-1}$) | 1.2 × 10$^{-1}$ |
| $K_D$ (M) | 1.3 × 10$^{-7}$ |

Under non-reducing conditions, 3C12 detects recombinant human CD83$_{ECD}$-His on a western blot, yet 3C12 binding is abolished when CD83 has been denatured by heat and disulphide bond reduction. This observation also holds for commercial antibody HB15e (FIG. 3A). Consequently, both 3C12 and HB15e appear to bind to conformational epitopes which are destroyed by heat and disulphide reduction. To determine whether CD83 mAbs bound competitively or independently of other anti-CD83 reagents, 3C12 IgG was conjugated to RPE and competitively assayed with FITC-conjugated commercial antibodies HB15a and HB15e, and RA83 polyclonal antibody detected with anti-rabbit-Ig. Competitive blocking with 3C12 was evident upon simultaneous addition of the antibodies, as full inhibition of HB15e, and partial inhibition of HB15a and RA83 binding was observed in the presence of 3C12 (FIG. 3 inset table). This indicates the 3C12 epitope is shared or overlapping with that of other antibodies. Under the conditions examined, 3C12 binding was minimally altered by addition of any of the anti-CD83 reagents, with only a marginal decrease in 3C12 signal observed in competition with RA83. This finding demonstrates that 3C12 antibody competes with other anti-CD83 reagents for antigen binding and that the 3C12 epitope is similar to that of antibodies derived from traditional approaches to antibody generation.

Example 4 In Vivo Evaluation of 3C12 mAb

To assess the ability of the 3C12 mAb to prevent GVHD in vivo, the antibody was administered to SCID mice receiving a xenogeneic transplant of human PBMC. Dosing of the 3C12 antibody was varied three-fold above and below the optimal dose of 0.125 mg previously determined for the rabbit polyclonal antibody RA83 (Wilson et al., Med. 206 (2): 387-98, 2009). As observed for RA83, administration of 0.125 mg 3C12 significantly improves survival in the xenogeneic GVHD model, relative to its isotype control (FIG. 4A). Increasing the dose of 3C12 IgG to 0.375 mg resulted in decreased treatment efficacy, although this trend was not significant. In comparison to the standard 0.125 mg dose of rabbit polyclonal RA83 antibody, which produced 61% survival, 3C12 IgG at the equivalent dose was less potent, protecting 39% of mice from succumbing to GVHD (FIG. 4B). Increasing the dose of RA83 to 1 mg resulted in 100% survival, yet the same increase to 3C12 antibody abolished efficacy of the monoclonal antibody (FIG. 4C). Co-treatment of animals with the standard dose (0.125 mg) of RA83 with 1 mg of 3C12 IgG was also ineffective. This indicates the effect of RA83 was inhibited by the presence of a high dose of 3C12. As the standard and lower doses of 3C12 were effective, but less potent than RA83 in vivo, the 3C12 antibody was subjected to further antibody engineering designed to improve mAb potency.

Example 5 Glyco-Engineering of a CD83 mAb

To produce an afucosylated antibody for the purpose of improving the potential for ADCC, kifunensine, a potent glycosidase inhibitor, was added during CHO cell transfection with 3C12-encoding cDNA. FIG. 5 demonstrates that the presence of kifunensine during the transfection effectively blocks fucose addition of the 3C12 antibody (i.e., 3C12.Kif), as assessed by mass spectrometry. Glycans released from the 3C12.Kif sample by N-glycosidase F digestion produced a predominant signal at approximately 1905 m/z, corresponding to GlcNAc2Man9, as expected if there is no processing of high mannose glycans. There were also smaller signals at 1742 m/z and 1580 m/z corresponding to GlcNAc2Man8 and GlcNAc2Man7 respectively. In comparison, wildtype 3C12 produces a dominant signal at 1485 m/z, corresponding to fucose-containing carbohydrate. The glyco-modification was made without discernibly altering molecular weight, specificity and functional affinity of wildtype 3C12 (FIG. 5B, C).

Example 6 Affinity-Engineering of a CD83 mAb by Light Chain Shuffling

Affinity maturation by light chain shuffling was utilized to improve the strength of the antigen-antibody interaction as a strategy for enhancing functionality. Here, the 3C12 $V_H$ DNA sequence was cloned into a cDNA library of human $V_L$ sequences, and the resulting library of approximately $10^7$ unique $V_H$-$V_L$ pairings displayed on the surface of yeast cells to allow affinity driven selections. At the protein level, many of these pairings are detrimental to the ability of 3C12 to bind to CD83 antigen, as <1% of displayed scFv remained positive for antigen binding in the first round of yeast sorting (FIG. 6A). Clones with improved affinity for recombinant CD83 antigen were selected by enriching for yeast, displaying scFv that strongly bound hCD83$_{ECD}$-His relative to the level of scFv expression on the surface of the yeast, determined by detecting the fluorescence intensity of an SV5 tag expressed at the C-terminal of each scFv. Selection of scFv clones by this method produced four new 3C12 scFv variants with distinct $V_L$ sequences and enhanced binding properties relative to the wildtype scFv (FIG. 6B, C).

Whole human IgG1 reformatted affinity matured 3C12 mAbs, when prepared as Fab binders using papain digestion were estimated to have 3-20 fold affinity improvements relative to the wildtype (3C12.WT), as determined by Biacore SPR (Table 5). The greatest improvements to antibody binding are attributable to slower kinetic off-rates, with clones demonstrating 8 to 15-fold improvements to the observed koff Antibody on-rate remained similar to that of 3C12 wildtype ($K_{on}$=9.0×10$^5$M$^{-1}$s$^{-1}$), with most clones exhibiting <1.4-fold improvements and one clone (3C12.B) had approximately 3-fold reduction in on-rate ($K_{on}$=3.2×10$^5$ M$^{-1}$s$^{-1}$). In terms of overall affinity improvement, variant 3C12.C had the highest observed affinity for CD83 (KD=6.1×10$^{-9}$M) including the best (i.e., slowest) off-rate (Koff=7.8×10$^{-3}$ s$^{-1}$) and was further characterized. FIG. 7A graphically highlights these improvements of 3C12.C binding relative to 3C12.WT, as higher binding signal intensity (i.e., RU) is achieved using reduced concentrations of the $V_L$ shuffled variant during the $K_{off}$ and $K_{on}$-dependent Association Phase. Similarly, a slower off-rate is observed for 3C12.C Fab during the $K_{off}$-dependent dissociation phase. As a whole IgG molecule, the affinity improved 3C12.C IgG also demonstrated superior binding to KM-H2 cells relative to 3C12.WT IgG (FIG. 7B).

TABLE 5

Affinity of wildtype 3C12 (3C12.WT) and $V_L$ shuffled variant Fab fragments

| Clone | Fab $K_{on}$ (1/Ms) | Fab $K_{off}$ (1/s) | Fab $K_D$ (M) |
| --- | --- | --- | --- |
| 3C12.WT | 9.0 × 10$^5$ | 1.2 × 10$^{-1}$ | 1.3 × 10$^{-7}$ |
| 3C12.B | 3.2 × 10$^5$ | 1.4 × 10$^{-2}$ | 4.3 × 10$^{-8}$ |
| 3C12.C | 1.3 × 10$^6$ | 7.8 × 10$^{-3}$ | 6.1 × 10$^{-9}$ |
| 3C12.D | 1.1 × 10$^6$ | 2.7 × 10$^{-2}$ | 2.5 × 10$^{-8}$ |
| 3C12.E | 1.2 × 10$^6$ | 5.0 × 10$^{-2}$ | 4.2 × 10$^{-8}$ |

Example 7: Glyco- and Affinity Engineered 3C12 Variants Improve In Vitro Efficacy Improvements to functional activity of glyco-engineered 3C12.kif and affinity enhanced 3C12.C antibodies were assessed by ADCC assay and within a MLR. Both 3C12.C and 3C12.Kif produce >10% increased maximal NK-mediated ADCC in a chromium release assay, and had >25-fold potency than 3C12.WT (FIG. 8A). Likewise, cellular proliferation as a result of allogeneic stimulation within an MLR was inhibited by 3C12.C and 3C12.Kif IgG with >5-fold increased potency than 3C12.WT (FIG. 8B). Superior activity was observed for 3C12.C, which demonstrated comparable potency to polyclonal antibody, RA83.

Example 8: In Vitro Mechanisms of Action of an Engineered Anti-CD83 mAb

To determine the effect of anti-CD83 mAb on primary blood DCs, 3C12.C antibody was applied to cultured PBMC in the presence of IL-2 to activate NK cells. Cells cultured in the presence of 3C12.C IgG had reduced percentages of activated DCs (58%) as opposed to nil or isotype control treated cells (>80%), as assessed by activation markers CMRF-44 and CD83 (detected by unconjugated 3C12.C and 10 secondary anti-human Fc-FITC, rather than FITC-conjugated 3C12.C, so as to remove the potential for any reduction in detection signal intensity due to competition with the treatment antibody; FIG. 9). Also, the population of CD83$^{bright}$ expressing DCs present in both nil and isotype-treated controls was absent after 3C12.C treatment, whereas only CD83dim populations of DCs were observed. To determine whether the level of cell surface CD83 expression is a contributing factor to the ability of 3C12.C to induce ADCC, stably transfected BB88 cells with varying levels of CD83 expression were used. The number of CD83 molecules on these cells, and other CD83-expressing cell lines was quantified using an indirect immunofluorescence flow cytometry assay, which showed that the BB88 transfectants express from 5,400 molecules per cell (MPC) to <2,300 MPC of CD83 antigen (Table 6). Thus, the transfectants possess much lower levels of CD83 in comparison to expression levels on immortalized cell lines and primary blood DCs (10,000-50,000 MPC). Each of the BB88 CD83 transfected cell lines were specifically lysed by engineered 3C12 variants, demonstrating only low levels of cell surface CD83 are required to trigger ADCC. Furthermore, the extent of lysis induced by 3C12 mAb variants is sensitive to the number of the CD83 molecules expressed on the cell surface. This is exemplified in FIG. 10, where increasing antigen density from <2,300 to 3,600 and 5,400 correlated with increased 5-25-fold increased specific lysis.

TABLE 6

QIFIKit quantification of CD83 antigen density

| Cell Type | CD83 Molecules per cell (MPC) | Independent Replicates |
| --- | --- | --- |
| BB88-CD83-TF.5K | 5,400 | 2 |
| BB88-CD83-TF.3K | 3,600 | 1 |
| BB88-CD83-TF.2K | <2,300* | 2 |
| KM-H2 | 55,000 | 6 |
| Raji | 49,000 | 1 |
| L428 | 11,000 | 1 |
| Activated blood DC$^{bright}$** | 49,000 | 2 |
| Activated blood DC$^{mid}$** | 20,000 | 1 |
| Activated blood DC$^{dim}$** | <2,300 | 1 |

*Below limits of QIFI kit standards
**See Appendix 6 for gating
TF = transfected cells Example 9 Affinity Matured Anti-CD83 mAb, 3C12.C is Efficacious in a Xenogeneic GVHD Model To assess the affinity enhanced 3C12.C mAb to prevent GVHD in vivo, the $V_L$ shuffled 3C12 variant was administered at the standard 0.125 mg dose to conditioned SCID mice transplanted with human PBMC. In comparison to the polyclonal reagent, RA83 which protected 45% (5/11) of mice, 3C12.C IgG demonstrated equivalent potency, preventing GVHD in 54% (6/11) of mice, and higher potency than 3C12.WT which had 27% (4/15) survival (FIG. 11). The efficacy of all cohorts appeared reduced in comparison to previous findings (Wilson et al., J. Exp. Med. 206(2): 387-98, 2009) as RA83 and 3C12.WT typically provide >60% and 40% survival respectively. Under these experimental conditions only 3C12.C was significantly different to the isotype control.

The invention claimed is:

1. A method for treating or preventing a CD83-associated disease or condition in a subject comprising administering to the subject a CD83 binding protein comprising an antigen binding domain which specifically binds to CD83, wherein the CD83 binding protein comprises:
  (a) a heavy chain variable region ($V_H$) which comprises:
    (i) a sequence which is the amino acid sequence shown in SEQ ID NO: 1; or
    (ii) three complementarity determining regions (CDRs) of the amino acid sequence shown in SEQ ID NO: 1; and
  (b) a light chain variable region ($V_L$) which comprises:
    (i) a sequence which is any one of the amino acid sequences shown in SEQ ID NO: 5, 6, 7, 8, or 9; or
    (ii) three complementarity determining regions (CDRs) of any one of the amino acid sequence shown in SEQ ID NO: 5, 6, 7, 8, or 9; or
    (iii) a consensus sequence as shown in SEQ ID NO: 10; or
    (iv) three CDRs, wherein the amino acid sequence of CDR1, CDR2, or CDR3 is a consensus sequence shown in SEQ ID NO: 26, 27 or 28.

2. The method of claim 1, wherein the CD83 binding protein comprises a $V_L$ sequence as shown in SEQ ID NO:7.

3. The method of claim 1, wherein the CD83 binding protein comprises: (a) a heavy chain variable region (VH) which comprises the amino acid sequence of SEQ ID NO: 1 and comprises: (i) a CDR1 which comprises the amino acid sequence shown in SEQ ID NO: 2; (ii) a CDR2 which comprises the amino acid sequence shown in SEQ ID NO: 3; and (iii) a CDR3 which comprises the amino acid sequence shown in SEQ ID NO: 4; and (b) a light chain variable region (VL) which comprises: (i) a CDR1 as shown in SEQ ID NO: 26; (ii) a CDR2 as shown in SEQ ID NO: 27, and (iii) a CDR3 as shown in SEQ ID NO: 28.

4. The method of claim 3, wherein the $V_L$ sequence comprises SEQ ID NO: 7.

5. The method of claim 1, wherein the $V_L$ and $V_H$ of the CD83 binding protein are in a single polypeptide chain.

6. The method of claim 5, wherein the CD83 binding protein is:
  (i) a single chain FIT fragment (scFv); or
  (ii) a dimeric scFv (di-scFv); or
  (iii) (i) or (ii) linked to a Fc or a heavy chain constant domain ($C_H$) 2 and/or $C_H$3; or
  (iv) (i) or (ii) linked to a protein that binds to an immune effector cell.

7. The method of claim 1, wherein the $V_L$ and $V_H$ of the CD83 binding protein are in separate polypeptide chains.

8. The method of claim 7, wherein the CD83 binding protein is:
  (i) a diabody; or
  (ii) a triabody; or
  (iii) a tetrabody; or
  (iv) a Fab; or (v) a F(ab')2; or
(vi) a Fv; or
(vii) one of (i) to (vi) linked to a Fc or a $C_H2$ and/or $C_H3$; or
(viii) one of (i) to (vi) linked to a protein that binds to an immune effector cell.

9. The method of claim 1, wherein the CD83 binding protein is an antibody.

10. The method of claim 9, wherein the antibody comprises:
(i) a $V_H$ sequence as shown in SEQ ID NO:1 and a $V_L$ sequence as shown in SEQ ID NO:5; or
(ii) a $V_H$ sequence as shown in SEQ ID NO:1 and a $V_L$ sequence as shown in SEQ ID NO:6;
(iii) a $V_H$ sequence as shown in SEQ ID NO:1 and a $V_L$ sequence as shown in SEQ ID NO:7; or
(iv) a $V_H$ sequence as shown in SEQ ID NO:1 and a $V_L$ sequence as shown in SEQ ID NO:8; or
(v) a $V_H$ sequence as shown in SEQ ID NO:1 and a $V_L$ sequence as shown in SEQ ID NO:9; or
(vi) a heavy chain sequence as shown in SEQ ID NO:29 and a light chain sequence as shown in SEQ ID NO:30; or
(vii) a heavy chain sequence as shown in SEQ ID NO:29 and a light chain sequence as shown in SEQ ID NO:31; or
(viii) a heavy chain sequence as shown in SEQ ID NO:29 and a light chain sequence as shown in SEQ ID NO:32; or
(ix) a heavy chain sequence as shown in SEQ ID NO:29 and a light chain sequence as shown in SEQ ID NO:33; or
(x) a heavy chain sequence as shown in SEQ ID NO:29 and a light chain sequence as shown in SEQ ID NO:34.

11. The method of claim 1, wherein the CD83 binding protein is chimeric, de-immunized, humanized, synhumanized, human, primatized, or a composite protein.

12. The method of claim 1, wherein the CD83 binding protein comprises an Fc region capable of inducing an enhanced level of effector function compared to a human IgG1 Fc region and/or conferring an extended half-life compared to a human IgG1 Fc region.

13. The method of claim 1, wherein the CD83 binding protein competitively inhibits binding of an antibody comprising a heavy chain sequence as shown in SEQ ID NO:29 and a light chain sequence as shown in SEQ ID NO:30 to CD83 or which binds to the same epitope in CD83 as said antibody.

14. The method of claim 1, wherein the CD83 binding protein is conjugated to a compound.

15. The method of claim 1, wherein the CD83 binding protein is a naked binding protein.

16. The method of claim 1, wherein the disease or condition is an inflammatory or autoimmune disease or condition.

17. The method of claim 1, wherein the disease or condition is caused by the dysfunction or undesired function of a cellular immune response involving T cells and/or dendritic cells in a subject.

18. The method of claim 1, wherein the disease or condition is selected from the group consisting of allergy, asthma, rejection of a tissue or organ graft, rejection of a transplanted organ, an autoimmune condition, chronic inflammatory bowel diseases, HLA B27-associated autoimmunopathis, skin diseases, rheumatoid arthritis, insulin-dependent diabetes mellitus and AIDS.

19. The method of claim 18, wherein the rejection of a tissue or organ graft occurs as a result of graft versus host disease.

20. The method of claim 18, wherein the rejection of a transplanted organ (e.g. heart, kidney, liver) as a result of host rejection.

21. The method of claim 18, wherein the disease or condition is graft versus host disease and administration of the CD83 binding protein downregulates the immunoactivity of an allogeneic graft.

22. The method of claim 18, wherein the autoimmune condition is selected from the group consisting of myasthemia gravis, multiple sclerosis, and vasculitis.

23. The method of claim 18, wherein the chronic inflammatory bowel disease is Crohn's disease or ulcerative colitis.

24. The method of claim 18, wherein the HLA-B27 associated autoimmunopathies is selected from the group consisting of Bechterew's disease (Ankylosing Spondylitis) and systemic lupus erythematosus.

25. The method of claim 18, wherein the skin disease is psoriasis.

* * * * *

UNITED STATES PATENT AND TRADEMARK OFFICE
CERTIFICATE OF CORRECTION

PATENT NO. : 10,781,255 B2
APPLICATION NO. : 15/808423
DATED : September 22, 2020
INVENTOR(S) : Seldon et al.

Page 1 of 1

It is certified that error appears in the above-identified patent and that said Letters Patent is hereby corrected as shown below:

In the Claims

Column 91, Line 66: Claim 3, Delete "(VH)" and insert -- ($V_H$) --

Column 92, Line 45: Claim 3, Delete "(VL)" and insert -- ($V_L$) --

Column 92, Line 54: Claim 6, Delete "FIT" and insert -- $F_v$ --

Signed and Sealed this
Tenth Day of November, 2020

Andrei Iancu
*Director of the United States Patent and Trademark Office*

SEQUENCE LISTING

<160> NUMBER OF SEQ ID NOS: 55

<210> SEQ ID NO 1
<211> LENGTH: 117
<212> TYPE: PRT
<213> ORGANISM: Artificial Sequence
<220> FEATURE:
<223> OTHER INFORMATION: heavy chain variable region

<400> SEQUENCE: 1

```
Glu Val Gln Leu Gln Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
            85                  90                  95

Ala Arg His Tyr Tyr Tyr Gly Met Asp Val Trp Gly Gln Gly Thr Thr
        100                 105                 110

Leu Thr Val Ser Ser
    115
```

<210> SEQ ID NO 2
<211> LENGTH: 5
<212> TYPE: PRT
<213> ORGANISM: Artificial Sequence
<220> FEATURE:
<223> OTHER INFORMATION: CDR sequence

<400> SEQUENCE: 2

Ser Tyr Ala Met His
1               5

<210> SEQ ID NO 3
<211> LENGTH: 10
<212> TYPE: PRT
<213> ORGANISM: Artificial Sequence
<220> FEATURE:
<223> OTHER INFORMATION: CDR sequence

<400> SEQUENCE: 3

Val Ile Ser Tyr Asp Gly Ser Asn Lys Tyr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: CDR sequence

<400> SEQUENCE: 4

His Tyr Tyr Tyr Gly Met Asp Val
1               5

<210> SEQ ID NO 5
<211> LENGTH: 107
<212> TYPE: PRT
<213> ORGANISM: Artificial Sequence
<220> FEATURE:
<223> OTHER INFORMATION: light chain variable region

<400> SEQUENCE: 5

Glu Ile Val Met Thr Gln Ser Pro Ser Leu Leu Ser Ala Ser Leu Gly
1               5                   10                  15

Asp Arg Val Thr Ile Thr Cys Arg Ala Ser Gln Gly Ile Lys Asn Tyr
            20                  25                  30

Phe Ala Trp Tyr Gln Gln Arg Pro Gly Lys Ala Pro Lys Leu Leu Ile
        35                  40                  45

Tyr Ala Thr Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Gly Ala Tyr Pro Leu
                85                  90                  95

Thr Phe Gly Gly Gly Thr Lys Leu Glu Leu Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: light chain variable region

<400> SEQUENCE: 6

```
Glu Val Val Met Thr Gln Ser Pro Ser Phe Leu Ser Ala Ser Ile Gly
1               5                   10                  15

Asp Arg Val Ser Ile Thr Cys Arg Thr Ser Gln Gly Ile Ser Asn His
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Val Asn Ser Tyr Pro Tyr
                85                  90                  95

Thr Phe Gly Gln Gly Thr Arg Leu Glu Leu Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: light chain variable region

<400> SEQUENCE: 7

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Val Pro Lys Leu Leu Ile
            35                  40                  45

Tyr Ala Thr Ser Thr Leu Gln Ser Gly Val Pro Ser Arg Phe Ser Gly
    50                  55                  60

Ser Arg Ser Gly Thr Glu Phe Thr Leu Thr Ile Ser Ser Leu His Pro
65                  70                  75                  80

Glu Asp Phe Ala Thr Tyr Tyr Cys Gln Gln Val Asp Arg Phe Pro Tyr
                85                  90                  95

Thr Phe Gly Gln Gly Thr Lys Val Glu Leu Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: light chain variable region

<400> SEQUENCE: 8

Glu Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Lys Leu Ser Ser Tyr Pro Tyr
```

```
                    85                  90                  95

Thr Phe Gly Gly Gly Thr Lys Val Glu Leu Lys
                100                 105

<210> SEQ ID NO 9
<211> LENGTH: 107
<212> TYPE: PRT
<213> ORGANISM: Artificial Sequence
<220> FEATURE:
<223> OTHER INFORMATION: light chain variable region

<400> SEQUENCE: 9

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Val Ala Thr Tyr Tyr Cys Gln Lys Cys Asn Ser Ala Pro Tyr
                85                  90                  95

Thr Phe Gly Gln Gly Thr Lys Val Glu Leu Lys
                100                 105

<210> SEQ ID NO 10
<211> LENGTH: 107
<212> TYPE: PRT
<213> ORGANISM: Artificial Sequence
<220> FEATURE:
<223> OTHER INFORMATION: consensus sequence
<220> FEATURE:
<221> NAME/KEY: X
<222> LOCATION: (2)..(2)
<223> OTHER INFORMATION: I or V
<220> FEATURE:
<221> NAME/KEY: X
<222> LOCATION: (3)..(3)
<223> OTHER INFORMATION: V or Q
<220> FEATURE:
<221> NAME/KEY: X
<222> LOCATION: (4)..(4)
<223> OTHER INFORMATION: M or L
<220> FEATURE:
<221> NAME/KEY: X
<222> LOCATION: (10)..(10)
<223> OTHER INFORMATION: L or F or S
<220> FEATURE:
<221> NAME/KEY: X
<222> LOCATION: (15)..(15)
<223> OTHER INFORMATION: L or I or V
<220> FEATURE:
<221> NAME/KEY: X
<222> LOCATION: (20)..(20)
<223> OTHER INFORMATION: T or S
<220> FEATURE:
<221> NAME/KEY: X
<222> LOCATION: (25)..(25)
<223> OTHER INFORMATION: A or T
<220> FEATURE:
<221> NAME/KEY: X
<222> LOCATION: (30)..(30)
<223> OTHER INFORMATION: K or S or R
<220> FEATURE:
<221> NAME/KEY: X
<222> LOCATION: (31)..(31)
<223> OTHER INFORMATION: N or S
```

```
<220> FEATURE:
<221> NAME/KEY: X
<222> LOCATION: (32)..(32)
<223> OTHER INFORMATION: Y or H or W
<220> FEATURE:
<221> NAME/KEY: X
<222> LOCATION: (33)..(33)
<223> OTHER INFORMATION: F or L
<220> FEATURE:
<221> NAME/KEY: X
<222> LOCATION: (39)..(39)
<223> OTHER INFORMATION: R or K
<220> FEATURE:
<221> NAME/KEY: X
<222> LOCATION: (43)..(43)
<223> OTHER INFORMATION: A or V
<220> FEATURE:
<221> NAME/KEY: X
<222> LOCATION: (51)..(51)
<223> OTHER INFORMATION: T or A
<220> FEATURE:
<221> NAME/KEY: X
<222> LOCATION: (53)..(53)
<223> OTHER INFORMATION: N or S or T
<220> FEATURE:
<221> NAME/KEY: X
<222> LOCATION: (66)..(66)
<223> OTHER INFORMATION: G or R
<220> FEATURE:
<221> NAME/KEY: X
<222> LOCATION: (70)..(70)
<223> OTHER INFORMATION: E or D or H
<220> FEATURE:
<221> NAME/KEY: X
<222> LOCATION: (79)..(79)
<223> OTHER INFORMATION: Q or H
<220> FEATURE:
<221> NAME/KEY: X
<222> LOCATION: (81)..(81)
<223> OTHER INFORMATION: E or D
<220> FEATURE:
<221> NAME/KEY: X
<222> LOCATION: (83)..(83)
<223> OTHER INFORMATION: F or I or V
<220> FEATURE:
<221> NAME/KEY: X
<222> LOCATION: (90)..(90)
<223> OTHER INFORMATION: Q or K
<220> FEATURE:
<221> NAME/KEY: X
<222> LOCATION: (91)..(91)
<223> OTHER INFORMATION: L or V or C
<220> FEATURE:
<221> NAME/KEY: X
<222> LOCATION: (92)..(92)
<223> OTHER INFORMATION: G or N or D or S
<220> FEATURE:
<221> NAME/KEY: X
<222> LOCATION: (93)..(93)
<223> OTHER INFORMATION: A or S or R
<220> FEATURE:
<221> NAME/KEY: X
<222> LOCATION: (94)..(94)
<223> OTHER INFORMATION: Y or F or A
<220> FEATURE:
<221> NAME/KEY: X
<222> LOCATION: (96)..(96)
<223> OTHER INFORMATION: L or Y
<220> FEATURE:
<221> NAME/KEY: X
<222> LOCATION: (100)..(100)
<223> OTHER INFORMATION: G or Q
<220> FEATURE:
<221> NAME/KEY: X
<222> LOCATION: (103)..(103)
<223> OTHER INFORMATION: K or R
<220> FEATURE:
<221> NAME/KEY: X
<222> LOCATION: (104)..(104)
```

<223> OTHER INFORMATION: L or V

<400> SEQUENCE: 10

Glu Xaa Xaa Xaa Thr Gln Ser Pro Ser Xaa Leu Ser Ala Ser Xaa Gly
1               5                   10                  15

Asp Arg Val Xaa Ile Thr Cys Arg Xaa Ser Gln Gly Ile Xaa Xaa Xaa
            20                  25                  30

Xaa Ala Trp Tyr Gln Gln Xaa Pro Gly Lys Xaa Pro Lys Leu Leu Ile
        35                  40                  45

Tyr Ala Xaa Ser Xaa Leu Gln Ser Gly Val Pro Ser Arg Phe Ser Gly
    50                  55                  60

Ser Xaa Ser Gly Thr Xaa Phe Thr Leu Thr Ile Ser Ser Leu Xaa Pro
65                  70                  75                  80

Xaa Asp Xaa Ala Thr Tyr Tyr Cys Gln Xaa Xaa Xaa Xaa Pro Xaa
            85                  90                  95

Thr Phe Gly Xaa Gly Thr Xaa Xaa Glu Leu Lys
            100                 105

<210> SEQ ID NO 11
<211> LENGTH: 11
<212> TYPE: PRT
<213> ORGANISM: Artificial Sequence
<220> FEATURE:
<223> OTHER INFORMATION: CDR sequence

<400> SEQUENCE: 11

Arg Ala Ser Gln Gly Ile Lys Asn Tyr Phe Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: CDR sequence

<400> SEQUENCE: 12

Ala Thr Ser Asn Leu Gln Ser
1               5

<210> SEQ ID NO 13
<211> LENGTH: 9
<212> TYPE: PRT
<213> ORGANISM: Artificial Sequence
<220> FEATURE:
<223> OTHER INFORMATION: CDR sequence

<400> SEQUENCE: 13

Gln Gln Leu Gly Ala Tyr Pro Leu Thr
1               5

<210> SEQ ID NO 14
<211> LENGTH: 11
<212> TYPE: PRT
<213> ORGANISM: Artificial Sequence
<220> FEATURE:
<223> OTHER INFORMATION: CDR sequence

<400> SEQUENCE: 14

Arg Thr Ser Gln Gly Ile Ser Asn His Leu Ala
1               5                   10

<210> SEQ ID NO 15

```
<211> LENGTH: 7
<212> TYPE: PRT
<213> ORGANISM: Artificial Sequence
<220> FEATURE:
<223> OTHER INFORMATION: CDR sequence

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial Sequence
<220> FEATURE:
<223> OTHER INFORMATION: CDR sequence

<400> SEQUENCE: 16

Gln Gln Val Asn Ser Tyr Pro Tyr Thr
1               5

<210> SEQ ID NO 17
<211> LENGTH: 11
<212> TYPE: PRT
<213> ORGANISM: Artificial Sequence
<220> FEATURE:
<223> OTHER INFORMATION: CDR sequence

<400> SEQUENCE: 17

Arg Ala Ser Gln Gly Ile Arg Asn Tyr Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: CDR sequence

<400> SEQUENCE: 18

Ala Thr Ser Thr Leu Gln Ser
1               5

<210> SEQ ID NO 19
<211> LENGTH: 9
<212> TYPE: PRT
<213> ORGANISM: Artificial Sequence
<220> FEATURE:
<223> OTHER INFORMATION: CDR sequence

<400> SEQUENCE: 19

Gln Gln Val Asp Arg Phe Pro Tyr Thr
1               5

<210> SEQ ID NO 20
<211> LENGTH: 11
<212> TYPE: PRT
<213> ORGANISM: Artificial Sequence
<220> FEATURE:
<223> OTHER INFORMATION: CDR sequence

<400> SEQUENCE: 20

Arg Ala Ser Gln Gly Ile Ser Ser Trp Leu Ala
1               5                   10

<210> SEQ ID NO 21
<211> LENGTH: 7
```

```
<212> TYPE: PRT
<213> ORGANISM: Artificial Sequence
<220> FEATURE:
<223> OTHER INFORMATION: CDR sequence

<400> SEQUENCE: 21

Ala Ala Ser Ser Leu Gln Ser
1               5

<210> SEQ ID NO 22
<211> LENGTH: 9
<212> TYPE: PRT
<213> ORGANISM: Artificial Sequence
<220> FEATURE:
<223> OTHER INFORMATION: CDR sequence

<400> SEQUENCE: 22

Gln Lys Leu Ser Ser Tyr Pro Tyr Thr
1               5

<210> SEQ ID NO 23
<211> LENGTH: 11
<212> TYPE: PRT
<213> ORGANISM: Artificial Sequence
<220> FEATURE:
<223> OTHER INFORMATION: CDR sequence

<400> SEQUENCE: 23

Arg Ala Ser Gln Gly Ile Ser Asn Tyr Leu Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: CDR sequence

<400> SEQUENCE: 24

Ala Ala Ser Thr Leu Gln Ser
1               5

<210> SEQ ID NO 25
<211> LENGTH: 9
<212> TYPE: PRT
<213> ORGANISM: Artificial Sequence
<220> FEATURE:
<223> OTHER INFORMATION: CDR sequence

<400> SEQUENCE: 25

Gln Lys Cys Asn Ser Ala Pro Tyr Thr
1               5

<210> SEQ ID NO 26
<211> LENGTH: 11
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(2)
<223> OTHER INFORMATION: A or T
<220> FEATURE:
<221> NAME/KEY: misc_feature
<222> LOCATION: (7)..(7)
<223> OTHER INFORMATION: K or S or R
<220> FEATURE:
<221> NAME/KEY: misc_feature
```

<222> LOCATION: (8)..(8)
<223> OTHER INFORMATION: N or S
<220> FEATURE:
<221> NAME/KEY: misc_feature
<222> LOCATION: (9)..(9)
<223> OTHER INFORMATION: Y or H or W
<220> FEATURE:
<221> NAME/KEY: misc_feature
<222> LOCATION: (10)..(10)
<223> OTHER INFORMATION: F or L

<400> SEQUENCE: 26

Arg Xaa Ser Gln Gly Ile Xaa Xaa Xaa Xaa Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(2)
<223> OTHER INFORMATION: T or A
<220> FEATURE:
<221> NAME/KEY: misc_feature
<222> LOCATION: (4)..(4)
<223> OTHER INFORMATION: N or S or T

<400> SEQUENCE: 27

Ala Xaa Ser Xaa Leu Gln Ser
1               5

<210> SEQ ID NO 28
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (2)..(2)
<223> OTHER INFORMATION: Q or K
<220> FEATURE:
<221> NAME/KEY: misc_feature
<222> LOCATION: (3)..(3)
<223> OTHER INFORMATION: L or V or C
<220> FEATURE:
<221> NAME/KEY: misc_feature
<222> LOCATION: (4)..(4)
<223> OTHER INFORMATION: G or N or D or S
<220> FEATURE:
<221> NAME/KEY: misc_feature
<222> LOCATION: (5)..(5)
<223> OTHER INFORMATION: A or S or R
<220> FEATURE:
<221> NAME/KEY: misc_feature
<222> LOCATION: (6)..(6)
<223> OTHER INFORMATION: Y or F or A
<220> FEATURE:
<221> NAME/KEY: misc_feature
<222> LOCATION: (8)..(8)
<223> OTHER INFORMATION: Y or L

<400> SEQUENCE: 28

Gln Xaa Xaa Xaa Xaa Xaa Pro Xaa Thr
1               5

<210> SEQ ID NO 29
<211> LENGTH: 447
<212> TYPE: PRT
<213> ORGANISM: Artificial Sequence
<220> FEATURE:
<223> OTHER INFORMATION: heavy chain

<400> SEQUENCE: 29

```
Glu Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Tyr Tyr Tyr Gly Met Asp Val Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 30
<211> LENGTH: 214
<212> TYPE: PRT
<213> ORGANISM: Artificial Sequence
<220> FEATURE:
<223> OTHER INFORMATION: light chain

<400> SEQUENCE: 30

Glu Ile Val Met Thr Gln Ser Pro Ser Leu Leu Ser Ala Ser Leu Gly
1               5                   10                  15

Asp Arg Val Thr Ile Thr Cys Arg Ala Ser Gln Gly Ile Lys Asn Tyr
            20                  25                  30

Phe Ala Trp Tyr Gln Gln Arg Pro Gly Lys Ala Pro Lys Leu Leu Ile
        35                  40                  45

Tyr Ala Thr Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Gly Ala Tyr Pro Leu
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 214
<212> TYPE: PRT
<213> ORGANISM: Artificial Sequence
<220> FEATURE:
<223> OTHER INFORMATION: light chain

<400> SEQUENCE: 31

Glu Val Val Met Thr Gln Ser Pro Ser Phe Leu Ser Ala Ser Ile Gly
1               5                   10                  15

Asp Arg Val Ser Ile Thr Cys Arg Thr Ser Gln Gly Ile Ser Asn His
            20                  25                  30

Leu Ala Trp Tyr Gln Gln Lys Pro Gly Lys Ala Pro Lys Leu Leu Ile

```
                35                  40                  45
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Val Asn Ser Tyr Pro Tyr
                 85                  90                  95

Thr Phe Gly Gln Gly Thr Arg Leu Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 32
<211> LENGTH: 214
<212> TYPE: PRT
<213> ORGANISM: Artificial Sequence
<220> FEATURE:
<223> OTHER INFORMATION: ligth chain

<400> SEQUENCE: 32

Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
                 20                  25                  30

Leu Ala Trp Tyr Gln Gln Lys Pro Gly Lys Val Pro Lys Leu Leu Ile
             35                  40                  45

Tyr Ala Thr Ser Thr Leu Gln Ser Gly Val Pro Ser Arg Phe Ser Gly
 50                  55                  60

Ser Arg Ser Gly Thr Glu Phe Thr Leu Thr Ile Ser Ser Leu His Pro
 65                  70                  75                  80

Glu Asp Phe Ala Thr Tyr Tyr Cys Gln Gln Val Asp Arg Phe Pro Tyr
                 85                  90                  95

Thr Phe Gly Gln Gly Thr Lys Val Glu Leu Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                180                 185                 190
Ala Cys Glu Val Thr His Gln Gly Leu Ser Ser Pro Val Thr Lys Ser
            195                 200                 205

Phe Asn Arg Gly Glu Cys
    210

<210> SEQ ID NO 33
<211> LENGTH: 214
<212> TYPE: PRT
<213> ORGANISM: Artificial Sequence
<220> FEATURE:
<223> OTHER INFORMATION: light chain

<400> SEQUENCE: 33

Glu Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Lys Leu Ser Ser Tyr Pro Tyr
                85                  90                  95

Thr Phe Gly Gly Gly Thr Lys Val Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 214
<212> TYPE: PRT
<213> ORGANISM: Artificial Sequence
<220> FEATURE:
<223> OTHER INFORMATION: light chain

<400> SEQUENCE: 34

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45
```

```
Tyr Ala Ala Ser Thr Leu Gln Ser Gly Val Pro Ser Arg Phe Ser Gly
 50                  55                  60

Ser Gly Ser Gly Thr His Phe Thr Leu Thr Ile Ser Ser Leu Gln Pro
 65                  70                  75                  80

Glu Asp Val Ala Thr Tyr Tyr Cys Gln Lys Cys Asn Ser Ala Pro Tyr
                 85                  90                  95

Thr Phe Gly Gln Gly Thr Lys Val Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 35
<211> LENGTH: 351
<212> TYPE: DNA
<213> ORGANISM: Artificial Sequence
<220> FEATURE:
<223> OTHER INFORMATION: heavy chain variable region

<400> SEQUENCE: 35
gaggtgcagc tgcaggagtc ggggggaggc gtggtccagc ctgggaggtc cctgagactc        60
tcctgtgcag cctctggatt caccttcagt agctatgcta tgcactgggt ccgccaggct       120
ccaggcaagg ggctggagtg ggtggcagtt atatcatatg atggaagcaa taaatactac       180
gcagactccg tgaagggccg attcaccatc tccagagaca attccaagaa cacgctgtat       240
ctgcaaatga acagcctgag agccgaggac acggctatgt attactgtgc gagacactac       300
tactacggta tggacgtctg gggccaaggg accacgctca ccgtgtcctc c                351

<210> SEQ ID NO 36
<211> LENGTH: 321
<212> TYPE: DNA
<213> ORGANISM: Artificial Sequence
<220> FEATURE:
<223> OTHER INFORMATION: light chain variable region

<400> SEQUENCE: 36
gagatcgtga tgacccagtc tccatccctc ctgtctgctt ctttaggaga cagagtcacc        60
atcacttgtc gggccagtca ggcattaag  aattattttg cctggtatca gcaaagacca       120
gggaaagccc ctaagctcct gatctatgct acatccaatt tgcaaagtgg ggtcccatca       180
cgattcagcg gcagtggatc tgggacagaa ttcactctga caatcagcag cctgcagcct       240
gaagattttg caacttacta ttgtcaacaa cttggcgctt acccactcac tttcggcggg       300
gggaccaagc tggaactcaa g                                                 321

<210> SEQ ID NO 37
```

<210> SEQ ID NO 37
<211> LENGTH: 321
<212> TYPE: DNA
<213> ORGANISM: Artificial Sequence
<220> FEATURE:
<223> OTHER INFORMATION: light chain variable region

<400> SEQUENCE: 37

```
gaggttgtga tgacccagtc ccccagcttc ctgtccgcct ctatcggcga ccgggtgtcc     60
atcacctgtc ggacctccca gggcatctcc aaccacctgg cctggtatca gcagaagccc    120
ggcaaggccc ccaagctgct gatctacgcc gcctccagcc tgcagtccgg cgtgccatcc    180
agattctccg gctccggcag cggcaccgac ttcaccctga ccatcagctc cctgcagccc    240
gaggatatcg ccacctacta ctgccagcag gtgaactcct acccctacac cttcggccag    300
gggacacgac tggagctcaa g                                              321
```

<210> SEQ ID NO 38
<211> LENGTH: 321
<212> TYPE: DNA
<213> ORGANISM: Artificial Sequence
<220> FEATURE:
<223> OTHER INFORMATION: light chain variable region

<400> SEQUENCE: 38

```
gagattgtgc tgactcagtc cccctccagc ctgtccgcct ccgtgggcga cagagtgacc     60
atcacctgtc gggcctccca gggcatccgg aactacctgg cctggtatca gcagaaaccc    120
ggcaaggtgc ccaagctgct gatctacgcc acctccaccc tgcagtccgg cgtgccctcc    180
cggttctctg gctccagatc cggcaccgag ttcaccctga ccatctccag cctgcacccc    240
gaggacttcg ccacctacta ctgccagcag gtggaccggt tcccctacac cttcggccag    300
gggaccaagg tggaactcaa g                                              321
```

<210> SEQ ID NO 39
<211> LENGTH: 321
<212> TYPE: DNA
<213> ORGANISM: Artificial Sequence
<220> FEATURE:
<223> OTHER INFORMATION: light chain variable region

<400> SEQUENCE: 39

```
gagatccaga tgacccagtc cccctccagc ctgtccgcct ctgtgggcga cagagtgacc     60
atcacctgtc gggcctccca gggcatctcc agctggctgg cctggtatca gcagaagccc    120
ggcaaggccc ccaagctgct gatctacgcc gccagctccc tgcagtccgg cgtgccatcc    180
agattctccg gctccggcag cggcaccgag ttcaccctga ccatctccag cctgcagccc    240
gacgacttcg ccacctacta ctgccagaag ctgtcctcct acccctacac cttcggcgga    300
gggaccaagg tggaactcaa g                                              321
```

<210> SEQ ID NO 40
<211> LENGTH: 321
<212> TYPE: DNA
<213> ORGANISM: Artificial Sequence
<220> FEATURE:
<223> OTHER INFORMATION: light chain variable region

<400> SEQUENCE: 40

```
gagattgtgc tgactcagtc cccctccagc ctgtccgcct ccgtgggcga cagagtgacc     60
atcacctgtc gggcctccca gggcatctcc aactacctgg cctggtatca gcagaaaccc    120
ggcaaggtgc ccaagctgct gatctacgcc gcctccaccc tgcagtccgg cgtgccatcc    180
```
agattctccg gctccggcag cggcacccac ttcaccctga ccatctccag cctgcagccc    240
gaggacgtgg ccacctacta ctgccagaag tgcaactccg cccctacac cttcggccag     300 gggaccaagg tggaactcaa g                                              321

<210> SEQ ID NO 41
<211> LENGTH: 1401
<212> TYPE: DNA
<213> ORGANISM: Artificial Sequence
<220> FEATURE:
<223> OTHER INFORMATION: heavy chain

<400> SEQUENCE: 41
atgggatgga gctgtatcat cctcttcttg gtagcaacag ctacaggtgt ccactccgag     60
gtgcagctgc aggagtcggg gggaggcgtg gtccagcctg ggaggtccct gagactctcc    120
tgtgcagcct ctggattcac cttcagtagc tatgctatgc actgggtccg ccaggctcca    180
ggcaaggggc tggagtgggt ggcagttata tcatatgatg aagcaataa atactacgca     240 gactccgtga agggccgatt caccatctcc agagacaatt ccaagaacac gctgtatctg    300
caaatgaaca gcctgagagc cgaggacacg gctatgtatt actgtgcgag acactactac    360
tacggtatgg acgtctgggg ccaagggacc acgctcaccg tgtcctccgc ctccaccaag    420
ggcccttccg tgttccctct ggccccttcc tccaagtcca cctccggcgg caccgccgct    480
ctgggctgcc tggtgaagga ctacttccct gagcctgtga ccgtgtcctg gaactctggc    540
gccctgacct ctggcgtgca cacctttcct gctgtcctgc agtcctccgg cctgtactcc    600
ctgtcctccg tggtgaccgt gccttcctcc tccctgggca cccagaccta catctgcaac    660
gtgaaccaca gccttccaa caccaaggtg gacaagaagg tggagcctaa gtcctgcgac    720
aagacccaca cctgccctcc ctgccctgcc ctgagctgc tgggcggacc ctccgtgttc    780
ctgttccctc ctaagcctaa ggacaccctg atgatctccc ggaccctga ggtgacctgc    840 gtggtggtgg acgtgtccca cgaggatcct gaggtgaagt tcaattggta cgtggacggc    900
gtggaggtgc acaacgccaa gaccaagcct cgggaagagc agtacaactc cacctaccgg    960
gtggtgtctg tgctgaccgt gctgcaccag gactggctga acggcaagga atacaagtgc   1020
aaggtgtcca acaaggccct gcctgctccc atcgagaaga ccatctccaa ggccaagggc   1080
cagcctcgcg agcctcaggt gtatacctg cctcctccc gggacgagct gaccaagaac    1140
caggtgtccc tgacctgtct ggtgaagggc ttctaccctt ccgatatcgc cgtggagtgg   1200
gagtccaacg gccagcctga gaacaactac aagaccaccc ctcctgtgct ggactccgac   1260
ggctccttct cctgtactc caagctgacc gtggacaagt cccggtggca gcagggcaac   1320
gtgttctcct gctccgtgat gcacgaggcc ctgcacaacc actacaccca gaagtccctg   1380
tccctgtctc ctggcaagtg a                                            1401

<210> SEQ ID NO 42
<211> LENGTH: 702
<212> TYPE: DNA
<213> ORGANISM: Artificial Sequence
<220> FEATURE:
<223> OTHER INFORMATION: light chain

<400> SEQUENCE: 42
atgggctggt cctgcatcat cctgtttctg gtggccaccg ccaccggcgt gcactccgag     60
atcgtgatga cccagtctcc atccctcctg tctgcttctt taggagacag agtcaccatc    120

| | |
|---|---|
| acttgtcggg ccagtcaggg cattaagaat tattttgcct ggtatcagca aagaccaggg | 180 |
| aaagccccta agctcctgat ctatgctaca tccaatttgc aaagtggggt cccatcacga | 240 |
| ttcagcggca gtggatctgg gacagaattc actctgacaa tcagcagcct gcagcctgaa | 300 |
| gattttgcaa cttactattg tcaacaactt ggcgcttacc cactcacttt cggcggggg | 360 |
| accaagctgg aactcaagcg gaccgtggcc gctccttccg tgttcatctt ccctcccctcc | 420 |
| gacgagcagc tgaagtccgg caccgcctcc gtggtgtgcc tgctgaacaa cttctaccct | 480 |
| cgggaggcca aggtgcagtg gaaggtggac aacgccctgc agtccggcaa ctcccaggaa | 540 |
| tccgtcaccg agcaggactc caaggactct acctactccc tgtcctccac cctgaccctg | 600 |
| tccaaggccg actacgagaa gcacaaggtg tacgcctgcg aagtgaccca ccagggcctg | 660 |
| tcctctcccg tgaccaagtc cttcaaccgg ggcgagtgct ga | 702 |

<210> SEQ ID NO 43
<211> LENGTH: 702
<212> TYPE: DNA
<213> ORGANISM: Artificial Sequence
<220> FEATURE:
<223> OTHER INFORMATION: light chain

<400> SEQUENCE: 43

| | |
|---|---|
| atgggctggt cctgcatcat cctgtttctg gtggccaccg ccaccggcgt gcactccgag | 60 |
| gttgtgatga cccagtcccc cagcttcctg tccgcctcta tcggcgaccg ggtgtccatc | 120 |
| acctgtcgga cctcccaggg catctccaac acctggcct ggtatcagca gaagcccggc | 180 |
| aaggccccca agctgctgat ctacgccgcc tccagcctgc agtccggcgt gccatcaga | 240 |
| ttctccggct ccggcagcgg caccgacttc accctgacca tcagctccct gcagcccgag | 300 |
| gatatcgcca cctactactg ccagcaggtg aactcctacc cctacacctt cggccagggg | 360 |
| acacgactgg agctcaagcg gaccgtggcc gctccttccg tgttcatctt ccctcccctcc | 420 |
| gacgagcagc tgaagtccgg caccgcctcc gtggtgtgcc tgctgaacaa cttctaccct | 480 |
| cgggaggcca aggtgcagtg gaaggtggac aacgccctgc agtccggcaa ctcccaggaa | 540 |
| tccgtcaccg agcaggactc caaggactct acctactccc tgtcctccac cctgaccctg | 600 |
| tccaaggccg actacgagaa gcacaaggtg tacgcctgcg aagtgaccca ccagggcctg | 660 |
| tcctctcccg tgaccaagtc cttcaaccgg ggcgagtgct ga | 702 |

<210> SEQ ID NO 44
<211> LENGTH: 702
<212> TYPE: DNA
<213> ORGANISM: Artificial Sequence
<220> FEATURE:
<223> OTHER INFORMATION: light chain

<400> SEQUENCE: 44

| | |
|---|---|
| atgggctggt cctgcatcat cctgtttctg gtggccaccg ccaccggcgt gcactccgag | 60 |
| attgtgctga ctcagtcccc ctccagcctg tccgcctccg tgggcgacag agtgaccatc | 120 |
| acctgtcggg cctcccaggg catccggaac tacctggcct ggtatcagca gaaacccggc | 180 |
| aaggtgccca agctgctgat ctacgccacc tccaccctgc agtccggcgt gccctcccgg | 240 |
| ttctctggct ccagatccgg caccgagttc accctgacca tctccagcct gcaccccgag | 300 |
| gacttcgcca cctactactg ccagcaggtg accggttcc cctacacctt cggccagggg | 360 |
| accaaggtgg aactcaagcg gaccgtggcc gctccttccg tgttcatctt ccctcccctcc | 420 |
| gacgagcagc tgaagtccgg caccgcctcc gtggtgtgcc tgctgaacaa cttctaccct | 480 |

```
cgggaggcca aggtgcagtg aaggtggac aacgccctgc agtccggcaa ctcccaggaa      540
tccgtcaccg agcaggactc caaggactct acctactccc tgtcctccac cctgaccctg     600
tccaaggccg actacgagaa gcacaaggtg tacgcctgcg aagtgaccca ccagggcctg     660
tcctctcccg tgaccaagtc cttcaaccgg ggcgagtgct ga                        702
```

<210> SEQ ID NO 45
<211> LENGTH: 702
<212> TYPE: DNA
<213> ORGANISM: Artificial Sequence
<220> FEATURE:
<223> OTHER INFORMATION: light chain

<400> SEQUENCE: 45

```
atgggctggt cctgcatcat cctgtttctg gtggccaccg ccaccggcgt gcactccgag      60
atccagatga cccagtcccc ctccagcctg tccgcctctg tgggcgacag agtgaccatc     120
acctgtcggg cctcccaggg catctccagc tggctggcct ggtatcagca gaagcccggc    180
aaggccccca gctgctgat ctacgccgcc agctccctgc agtccggcgt gccatccaga     240
ttctccggct ccggcagcgg caccgagttc accctgacca tctccagcct gcagcccgac    300
gacttcgcca cctactactg ccagaagctg tcctcctacc ctacaccttt cggcggaggg    360
accaaggtgg aactcaagcg gaccgtggcc gctccttccg tgttcatctt ccctccctcc    420
gacgagcagc tgaagtccgg caccgcctcc gtggtgtgcc tgctgaacaa cttctaccct   480
cgggaggcca aggtgcagtg aaggtggac aacgccctgc agtccggcaa ctcccaggaa      540
tccgtcaccg agcaggactc caaggactct acctactccc tgtcctccac cctgaccctg     600
tccaaggccg actacgagaa gcacaaggtg tacgcctgcg aagtgaccca ccagggcctg     660
tcctctcccg tgaccaagtc cttcaaccgg ggcgagtgct ga                        702
```

<210> SEQ ID NO 46
<211> LENGTH: 702
<212> TYPE: DNA
<213> ORGANISM: Artificial Sequence
<220> FEATURE:
<223> OTHER INFORMATION: light chain

<400> SEQUENCE: 46

```
atgggctggt cctgcatcat cctgtttctg gtggccaccg ccaccggcgt gcactccgag      60
attgtgctga ctcagtcccc ctccagcctg tccgcctccg tgggcgacag agtgaccatc    120
acctgtcggg cctcccaggg catctccaac tacctggcct ggtatcagca gaaacccggc   180
aaggtgccca gctgctgat ctacgccgcc tccaccctgc agtccggcgt gccatccaga      240
ttctccggct ccggcagcgg cacccacttc accctgacca tctccagcct gcagcccgag    300
gacgtggcca cctactactg ccagaagtgc aactccgccc ctacaccttt cggccagggg    360
accaaggtgg aactcaagcg gaccgtggcc gctccttccg tgttcatctt ccctccctcc    420
gacgagcagc tgaagtccgg caccgcctcc gtggtgtgcc tgctgaacaa cttctaccct   480
cgggaggcca aggtgcagtg aaggtggac aacgccctgc agtccggcaa ctcccaggaa      540
tccgtcaccg agcaggactc caaggactct acctactccc tgtcctccac cctgaccctg     600
tccaaggccg actacgagaa gcacaaggtg tacgcctgcg aagtgaccca ccagggcctg     660
tcctctcccg tgaccaagtc cttcaaccgg ggcgagtgct ga                        702
```

<210> SEQ ID NO 47

```
<211> LENGTH: 205
<212> TYPE: PRT
<213> ORGANISM: Homo sapiens

<400> SEQUENCE: 47

Met Ser Arg Gly Leu Gln Leu Leu Leu Ser Cys Ala Tyr Ser Leu
1               5                   10                  15

Ala Pro Ala Thr Pro Glu Val Lys Val Ala Cys Ser Glu Asp Val Asp
                20                  25                  30

Leu Pro Cys Thr Ala Pro Trp Asp Pro Gln Val Pro Tyr Thr Val Ser
            35                  40                  45

Trp Val Lys Leu Leu Glu Gly Gly Glu Arg Met Glu Thr Pro Gln
        50                  55                  60

Glu Asp His Leu Arg Gly Gln His Tyr His Gln Lys Gly Gln Asn Gly
65              70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
            100                 105                 110

Asp Gly Gln Arg Asn Leu Ser Gly Lys Val Ile Leu Arg Val Thr Gly
        115                 120                 125

Cys Pro Ala Gln Arg Lys Glu Glu Thr Phe Lys Lys Tyr Arg Ala Glu
130                 135                 140

Ile Val Leu Leu Leu Ala Leu Val Ile Phe Tyr Leu Thr Leu Ile Ile
145                 150                 155                 160

Phe Thr Cys Lys Phe Ala Arg Leu Gln Ser Ile Phe Pro Asp Phe Ser
                165                 170                 175

Lys Ala Gly Met Glu Arg Ala Phe Leu Pro Val Thr Ser Pro Asn Lys
            180                 185                 190

His Leu Gly Leu Val Thr Pro His Lys Thr Glu Leu Val
        195                 200                 205

<210> SEQ ID NO 48
<211> LENGTH: 204
<212> TYPE: PRT
<213> ORGANISM: Homo sapiens

<400> SEQUENCE: 48

Met Ser Arg Gly Leu Gln Leu Leu Leu Ser Cys Ala Tyr Ser Leu
1               5                   10                  15

Ala Pro Ala Thr Pro Glu Val Lys Val Ala Cys Ser Glu Asp Val Asp
                20                  25                  30

Leu Pro Cys Thr Ala Pro Trp Asp Pro Gln Val Pro Tyr Thr Val Ser
            35                  40                  45

Trp Val Lys Leu Leu Glu Gly Gly Glu Arg Met Glu Thr Pro Gln
        50                  55                  60

Glu Asp His Leu Arg Gly Gln His Tyr His Gln Lys Gly Gln Asn Gly
65              70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
            100                 105                 110

Asp Gly Gln Arg Asn Leu Ser Gly Lys Val Ile Leu Arg Val Thr Gly
        115                 120                 125

Cys Pro Ala Gln Arg Lys Glu Glu Thr Phe Lys Lys Tyr Arg Ala Glu
130                 135                 140
```

Ile Val Leu Leu Leu Ala Leu Val Ile Phe Tyr Leu Thr Leu Ile Ile
145                 150                 155                 160

Phe Thr Cys Phe Ala Arg Leu Gln Ser Ile Phe Pro Asp Phe Ser Lys
                165                 170                 175

Ala Gly Met Glu Arg Ala Phe Leu Pro Val Thr Ser Pro Asn Lys His
            180                 185                 190

Leu Gly Leu Val Thr Pro His Lys Thr Glu Leu Val
            195                 200

<210> SEQ ID NO 49
<211> LENGTH: 146
<212> TYPE: PRT
<213> ORGANISM: Homo sapiens

<400> SEQUENCE: 49

Met Glu Thr Pro Gln Glu Asp His Leu Arg Gly Gln His Tyr His Gln
1               5                   10                  15

Lys Gly Gln Asn Gly Ser Phe Asp Ala Pro Asn Glu Arg Pro Tyr Ser
            20                  25                  30

Leu Lys Ile Arg Asn Thr Thr Ser Cys Asn Ser Gly Thr Tyr Arg Cys
        35                  40                  45

Thr Leu Gln Asp Pro Asp Gly Gln Arg Asn Leu Ser Gly Lys Val Ile
    50                  55                  60

Leu Arg Val Thr Gly Cys Pro Ala Gln Arg Lys Glu Glu Thr Phe Lys
65                  70                  75                  80

Lys Tyr Arg Ala Glu Ile Val Leu Leu Leu Ala Leu Val Ile Phe Tyr
                85                  90                  95

Leu Thr Leu Ile Ile Phe Thr Cys Lys Phe Ala Arg Leu Gln Ser Ile
            100                 105                 110

Phe Pro Asp Phe Ser Lys Ala Gly Met Glu Arg Ala Phe Leu Pro Val
        115                 120                 125

Thr Ser Pro Asn Lys His Leu Gly Leu Val Thr Pro His Lys Thr Glu
    130                 135                 140

Leu Val
145

<210> SEQ ID NO 50
<211> LENGTH: 32
<212> TYPE: DNA
<213> ORGANISM: Artificial Sequence
<220> FEATURE:
<223> OTHER INFORMATION: primer

<400> SEQUENCE: 50
caggtgtcca ctccgaggtg cagctgcagg ag          32

<210> SEQ ID NO 51
<211> LENGTH: 33
<212> TYPE: DNA
<213> ORGANISM: Artificial Sequence
<220> FEATURE:
<223> OTHER INFORMATION: primer

<400> SEQUENCE: 51
gcggaggaca cggtgagcgt ggtcccttgg ccc          33

<210> SEQ ID NO 52
<211> LENGTH: 32
<212> TYPE: DNA

```
<213> ORGANISM: Artificial Sequence
<220> FEATURE:
<223> OTHER INFORMATION: primer

<400> SEQUENCE: 52
ccggcgtgca ctccgagatc gtgatgaccc ag                                  32

<210> SEQ ID NO 53
<211> LENGTH: 32
<212> TYPE: DNA
<213> ORGANISM: Artificial Sequence
<220> FEATURE:
<223> OTHER INFORMATION: primer

<400> SEQUENCE: 53
gccacggtcc gcttgagttc cagcttggtc cc                                  32

<210> SEQ ID NO 54
<211> LENGTH: 50
<212> TYPE: DNA
<213> ORGANISM: Artificial Sequence
<220> FEATURE:
<223> OTHER INFORMATION: primer

<400> SEQUENCE: 54
gactatgcag ctagcggtgc catggcagag gtgcagctgc aggagtcggg               50

<210> SEQ ID NO 55
<211> LENGTH: 49
<212> TYPE: DNA
<213> ORGANISM: Artificial Sequence
<220> FEATURE:
<223> OTHER INFORMATION: primer

<400> SEQUENCE: 55
gttgagcctc cggacttaag gtcgactgag gacacggtga gcgtggtcc                49
```